US010308946B2

(12) United States Patent
Rasochova et al.

(10) Patent No.: US 10,308,946 B2
(45) Date of Patent: Jun. 4, 2019

(54) EXPRESSION CASSETTE FOR TRANSFORMATION COMPRISING A MODIFIED VIRAL SEQUENCE DRIVEN BY A SUITABLE PROMOTER

(75) Inventors: Lada Rasochova, Madison, WI (US); Thomas German, Hollandale, WI (US); Paul Ahlquist, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 2291 days.

(21) Appl. No.: 11/621,850

(22) Filed: Jan. 10, 2007

(65) Prior Publication Data

US 2009/0106855 A1 Apr. 23, 2009

Related U.S. Application Data

(63) Continuation of application No. 10/609,207, filed on Jun. 26, 2003, now abandoned, which is a continuation of application No. 09/316,622, filed on May 21, 1999, now abandoned.

(60) Provisional application No. 60/086,526, filed on May 22, 1998.

(51) Int. Cl.
*C12N 15/82* (2006.01)

(52) U.S. Cl.
CPC ..... *C12N 15/8203* (2013.01); *C12N 15/8205* (2013.01); *C12N 15/8216* (2013.01)

(58) Field of Classification Search
CPC .................................................. C12N 15/8203
USPC .......................................................... 800/278
See application file for complete search history.

(56) References Cited

U.S. PATENT DOCUMENTS

| | | | | |
|---|---|---|---|---|
| 5,418,153 | A | 5/1995 | Mod et al. | |
| 5,500,360 | A | 3/1996 | Ahlquist et al. | |
| 5,817,512 | A | 10/1998 | Morrow et al. | |
| 5,824,856 | A | 10/1998 | Mori et al. | |
| 5,851,757 | A | 12/1998 | Olivo et al. | |
| 5,853,716 | A | 12/1998 | Tattersall et al. | |
| 5,877,403 | A | 3/1999 | McMaster et al. | |
| 6,093,554 | A * | 7/2000 | Haute et al. | 435/69.1 |
| 2002/0104123 | A1* | 8/2002 | Turpen | 800/280 |

FOREIGN PATENT DOCUMENTS

| | | | |
|---|---|---|---|
| AU | 7195191 | A | 3/1992 |
| WO | WO-90/12107 | A1 | 10/1990 |
| WO | WO-95/07994 | A2 | 3/1995 |

OTHER PUBLICATIONS

Office Action dated Mar. 25, 2013 in Brazilian Application No. PI9911065-2, filed May 21, 1999.

Palu et al., "In pursuit of new developments for gene therapy of human diseases," *J. of Biotech.*, 1999, pp. 1-13, vol. 68.

Noueiry, et al., "Brome Mosaic Virus RNA Replication: Revealing the Role of the Host in RNA Virus Replication," *Annual Review of Phytopathology*, 2003, pp. 77-98, vol. 41.

Verchot et al., *J. of Virology*, 1995, pp. 3668-3674, vol. 69, No. 6.

Allison et al., *J. of Virology*, 1988, pp. 3581-3588, vol. 62, No. 10.

Fontes et al., *The Plant Cell*, 1994, pp. 405-416, vol. 6.

Berglund et al., "Enhancing immune responses using suicidal DNA vaccines," *Nature Biotech.*, 1998, pp. 562-565, vol. 16.

De Jong and Ahlquist, "A hybrid plant RNA virus made by transferring the noncapsid movement protein from a rod-shaped to an icosahedral virus is competent for systemic infection," *Proc. Natl. Acad. USA*, 1992, pp. 6808-6812, vol. 89.

Dinant et al., "Bromovirus RNA replication and transcription requires compatibility between the polymerase- and helicase-like viral RNA synthesis proteins," *J. Virol.*, 1993, pp. 7181-7189, vol. 67.

Dzianott and Bujarski, "Derivation of an infectious viral RNA by autolytic cleavage of in vitro transcribed viral cDNAs," *Proc. Natl. Acad. Sci. USA*, 1989, pp. 4823-4827, vol. 86.

Edwards, "Mapping of the seed transmission determinants of barley stripe mosaic virus," MPMI, 1995, pp. 906-915, vol. 8.

French and Ahlquist, "Characterization and engineering of sequences controlling in vivo synthesis of brome mosaic virus RNA3," *J. Virol.*, 1988, pp. 2411-2421, vol. 62, No. 7.

Hemenway et al., "Characterization of infectious transcripts from a potato virus X cDNA clone," *Virology*, 1990, pp. 365-371, vol. 175.

Ishikawa et al., "In Vivo DNA expression of functional brome mosaic virus RNA Replicons in *Saccharomyces cetevisiae," J. of Virology*, 1997, pp. 7781-7790, vol. 71, No. 10.

Jackson and Hunter, "Hordeivirus relationship and genome organization," *Annu. Rev. Phytopathol.*, 1989, pp. 95-121, vol. 27.

Janda et al., "High efficiency T7 polymerase synthesis of infectious RNA from cloned brome mosaic virus cDNA and effect of 5' extensions on transcript infectivity," *Virology*, 1987, pp. 259-262, vol. 158.

Kaido et al., "Inhibition of brome mosaic virus (BMV) amplification in protoplasts from transgenic tobacco plants expressing replicable BMV RNAs," *J. of Gener. Virology*, 1995, pp. 2827-2833, vol. 76.

Ishikawa et al., "Yeast mutations in multiple complementation groups inhibit brome mosaic virus RNA replication and transcription and perturb regulated expression of viral polymerase-like gene," PNAS, 1997, pp. 13810-13815, vol. 94.

Lewandowski and Dawson, "Deletion of internal sequences results in tobacco mosaic virus defective RNAs that accumulate to high levels without interfering with replication of the helper virus," *Virology*, 1998, pp. 427-437, vol. 251, No. 2.

(Continued)

*Primary Examiner* — Li Zheng

(74) *Attorney, Agent, or Firm* — Saliwanchik, Lloyd & Eisenschenk

(57) ABSTRACT

Disclosed herein are novel methods and materials directed to transforming a host cell and expressing exogenous RNA therein. Specifically disclosed are DNA-launching platforms used to introduce a replicating viral segment attached to an exogenous polynucleotide into a cell, whereby the exogenous polynucleotide is expressed in said cell and confers a detectable trait.

21 Claims, 20 Drawing Sheets

Specification includes a Sequence Listing.

(56) References Cited

OTHER PUBLICATIONS

Rasochova and Miller, "Satellite RNA of barley yellow dwarf-RPV virus reduces accumulation of RPV helper virus RNA and attenuates RPV symptoms on oats," *Molecular Plant-Microbe Interact*, 1996, pp. 646-650, vol. 9.
Selling et al., "Genomic RNA of an insect virus directs synthesis of infectious virions in plants," PNAS, 1990, pp. 434-438, vol. 87.
Timpe and Kuhne, "In Vitro transcript of a full-length cDNA of a naturally deleted RNA2 of barley mild mosaic virus (BaMMV) replicate in BaMMV-infected plants," *J. of General Virology*, 1995, pp. 2619-2623, vol. 76.
Töpper etal., "A set of plant expression vectors for transcriptional and translational fusions," *Nucleic Acids Res.*, 1987, p. 5890, vol. 15.
Van Der Vossen et al., "The 5' terminal sequence of Alfalfa mosaic virus RNA 3 is dispensable for replication and contains a determinant for symptom formation," *Virology*, 1996, pp. 271-280, vol. 221.
Zhou and Jackson, "Analysis of cis-acting elements for replication of barley stripe mosaic virus RNA," *Virology*, 1996, pp. 150-160, vol. 219.
Polo and Dubensky, "DNA vaccines with a kick," *Nature Biotech.*, 1998, pp. 517-518, vol. 16.
Price et al., "Complete replication of an animal virus and maintenance of expression vectors derived from it in *Saccharomyces cerevisiae," PNAS*, 1996, pp. 9465-9470, vol. 93.
Rasochova et al., "The Satellite RNA of barley yellow dwarf virus-RPV is supported by beet western yellows virus in Dicotyledonous Protoplasts and Plants," *Virology*, 1997, pp. 182-191, vol. 231.
Sacher et al., "Hybrid brome mosaic virus RNAs express and are packaged in tobacco mosaic virus coat protein in vivo," *Virology*, 1988, pp. 15-24, vol. 167.
Kashiwazaki et al., "Nucleotide sequence of barley yellow mosaic virus RNA1: a close evolutionary relationship with potyviruses," *J. of General Virology*, 1990, pp. 2781-2790, vol. 71.
Kashiwazaki et at. "Nucleotide sequence of barley yellow mosaic virus RNA2," *J. of General Virology*, 1991, pp. 995-999, vol. 72.
Kikkert, "The biolistic PDS 1000/He device," *Plant Cell Tiss. and Org. Cult.*, 1993, pp. 221-226, vol. 33.
Mori et al., Infectivity of plasmids containing brome mosaic virus cDNA linked to the cauliflower mosaic virus 35S RNA promoter, *J. of Gen. Virology*, 1991, pp. 243-246, vol. 72.
Mori et al., "Expression of brome mosaic virus-encoded replicase genes in transgenic tobacco plants," *J. of Gen. Virology*, 1992, pp. 169-172, vol. 73.
Neeleman et al., "Infection of tobacco with alfalfa mosaic virus cDNAs sheds light on the early function of the coat protein," *Virology*, 1993, pp. 883-887, vol. 196.
Pacha and Ahlquist, "Use of bromovirus RNA3 hybrids to study template specificity in viral RNA amplification," *J. of Virology*, 1991, pp. 3693-3703, vol. 65.
Petty and Jackson, "Mutational analysis of barley stripe mosaic virus Rna beta," *Virology*, 1990, pp. 712-718, vol. 179.
Crooke, "Antisense Research and Application," *Basic Principles of Antisense Therapeutics*, 1998, chapter 1.
Branch, "A good antisense molecule is hard to find," *TIBS*, 1998, pp. 45-50.

* cited by examiner

SEQUENCE LISTING

<160> NUMBER OF SEQ ID NOS: 8

<210> SEQ ID NO 1
<211> LENGTH: 7074
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (6318)..(6324)
<223> OTHER INFORMATION: 7 nucleotides which are unknown.
<220> FEATURE:
<221> NAME/KEY: unsure
<222> LOCATION: (6477)..(7074)
<223> OTHER INFORMATION: 598 nucleotides which are unknown.

<400> SEQUENCE: 1
aaacactgat agtttaaact gaaggcggga aacgacaatc tgatcatgag cggagaatta 60
agggagtcac gttatgaccc ccgccgatga cgcgggacaa gccgttttac gtttggaact 120
gacagaaccg caacgattga aggagccact cagccgcggg tttctggagt ttaatgagct 180
aagcacatac gtcagaaacc attattgcgc gttcaaaagt cgcctaaggt cactatcagc 240
tagcaaatat ttcttgtcaa aaatgctcca ctgacgttcc ataaattccc ctcggtatcc 300
aattagnnnn nnnnnnnnnn nnnnnnnnnn gatcgtttcg catgattgaa caagatggat 360
tgcacgcagg ttctccggcc gcttgggtgg agaggctatt cggctatgac tgggcacaac 420
agacaatcgg ctgctctgat gccgccgtgt tccggctgtc agcgcagggg cgcccggttc 480
tttttgtcaa gaccgacctg tccggtgccc tgaatgaact gcaggacgag gcagcgcggc 540
tatcgtggct ggccacgacg ggcgttcctt gcgcagctgt gctcgacgtt gtcactgaag 600
cgggaaggga ctggctgcta ttgggcgaag tgccggggca ggatctcctg tcatctcacc 660
ttgctcctgc cgagaaagta tccatcatgg ctgatgcaat gcggcggctg catacgcttg 720
atccggctac ctgcccattc gaccaccaag cgaaacatcg catcgagcga gcacgtactc 780
ggatggaagc cggtcttgtc gatcaggatg atctggacga agagcatcag gggctcgcgc 840
cagccgaact gttcgccagg ctcaaggcgc gcatgcccga cggcgatgat ctcgtcgtga 900
cccatggcga tgcctgcttg ccgaatatca tggtggaaaa tggccgcttt tctggattca 960
tcgactgtgg ccggctgggt gtggcggacc gctatcagga catagcgttg gctacccgtg 1020
atattgctga agagcttggc ggcgaatggg ctgaccgctt cctcgtgctt tacggtatcg 1080
ccgctcccga ttcgcagcgc atcgccttct atcgccttct tgacgagttc ttctgannnn 1140
nnnnnnnnnn nnnnnnnnnn gatcgttcaa acatttggca ataaagtttc ttaagattga 1200
atcctgttgc cggtcttgcg atgattatca tataatttct gttgaattac gttaagcatg 1260
taataattaa catgtaatgc atgacgttat ttatgagatg ggtttttatg attagagtcc 1320
cgcaattata catttaatac gcgatagaaa acaaaatata gcgcgcaaac taggataaat 1380
tatcgcgcgc ggtgtcatct atgttactag atcgggcctc ctgtcaatgc tggcggcggc 1440

-continued

```
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgcatgc   2100
ctgcaggtcg actctagagg atccccggtc actggatttt ggttttagga attagaaatt   2160
ttattgatag aagtatttta caaatacaaa tacatactaa gggtttctta tatgctcaac   2220
acatgagcga aaccctataa gaaccctaat tcccttatct gggaactact cacacattat   2280
tctggagaaa atagagagag atagatttgt agagagagac tggtgatttg cggactctag   2340
aggatccccg ggtaccgagc tcgaattctc gagcagaggt ctcacacaga gacaagcgca   2400
tcacttaaca caattaaaga tcaaatcacc agcgagctcg ccgttaaagc aatactcaaa   2460
ggacttcttg tgtcgtgtta aggcaaccaa acagtactcc tcatgtttaa acaaatcaca   2520
tttggtcgac ttaagccgaa ccaaagtgac gttgtcaaca gagatccctt gcgcttcgtg   2580
tactgttttt atgtgtccat caatccagtc cttgctcacg ggaaaatcct tagccctcgt   2640
ttgaagggcc gctttatcag cttgagtcat cgtaagatac gttctgttcg gatcaatagt   2700
gacctgcaaa ccagaagtaa tacgacgctt cgtgagactt ctagaaactt tggactcaga   2760
tgtccaggat tgatacttcg tgtccctatt accgcattta cgcttcagca gattaacagc   2820
agcgataaca tcttgcggac accggtaagt cttgtgaaca acgtcacggc gatcatattg   2880
cagattaccg tggagcaatt taaaacccgc gtcacgagac ttgaacgaaa tctgctctgt   2940
gtccccaaag gcaagaactt gtgaacattt agacagagca gccaccacca ggagttgacc   3000
ataatgtagt aaaccagcct catcaacaag cagcctatga caggacggta caccgtgcat   3060
gatcgcagaa tccgcggtgc gcacaacgtc caaagctacc ttggaattat aagtgtcagg   3120
gaataaagcc atcctgacgt cctcggccga tttacgattc gccgtcacaa ttaggtcctc   3180
tcccatacgg aatgcatctt ttatggcagt ggttttaccg catcccgcaa ctccatcaac   3240
catggaaata tcgcatgtag ggacagaaac tttggcgcta gcttctgcaa tgtccctcaa   3300
gttagagcat gcacatgttt tatcaacaat gtacgtttca tctgcgtgct tcggacctaa   3360
accatgctca ttatatccaa cagtgtaatc gtattttta ggatacaacc agttaccgtt   3420
ggccaaatgg acattcacca tatcgtctat gcgatggtag gtctcaaaga tgctcttatt   3480
tgcgatctca cttccgcgac cgccggaaat gtcccatagg tgacgaagat tagactcgga   3540
gttgttatgt aatctcttac aataacgcac aaattccttc atggctccgt gtctagatat   3600
gccacgaggg tccgttggta cctcaacaga cacctcggca tccgggacca catcagtcac   3660
cggtttaacg tcatcactga cggactcagg gctcgaactc tcaggggcat catgaaactc   3720
ctcctgaggt atctcagcag ctggcgggac tttcgccttc ttcttcgagc gcttggtctt   3780
ggctgtctgc acttcatgct ccagccggtc gaataagtcc tcttcagtcc aaaacgttct   3840
```

-continued

```
caaacgtgat atcggtacag aatcttgctc aaattcttca acgtttgaga gacgagtcag   3900
aaacttaaaa ctgtccgcat aagaatccag acgtagtagg ggaaatctgc tagccaatgt   3960
tctcagccat cctactttcg ccctggatga atctccaccc caccaaaacc tagttttgaa   4020
gtgatggcac caacctttcc attccatccc atcgcggagg gccgtaagct tttcgtactt   4080
ttgatacaga ttcaaagtca aagcaaaggc cactagatga taatcttcaa tgtctaagcg   4140
ctcaccagcc atgatagcct gaccgttaat aataacagtc gacgacttgg cggataagat   4200
agatgcgaca gctttcatgt tctcagtcca ttctttactt tccttgaaac atctgaaagc   4260
tatctcctct acctctctca ctgtggtttt ggcgacgcgc acacatttcc agcgattgag   4320
actccagtct tcaggtattg agacccctac gtacttagat atgtcttcaa accatacaca   4380
gtgacgtagt gtctcccggg ggcagcgtaa atttgtagcg atgatcttat aggtcatgat   4440
gttacatttc agcatttcgc gctccaacag ataggtggtt ccatcgatgc aatgcaccga   4500
ctcggtgaaa aatgagccca aatcttgcca tccgtggatg taagataatg tgctttcatt   4560
ttcaaaatcg aatttgatca cctcatccgc gcctgacccg tcacgttgcc agtgacattt   4620
aagcaaggga agaaaaccct cgcggtcaaa caacatggcg ccgtcgaaca taacggtacc   4680
acgtagtacg cgtactccat gcgaatgcat ggcgtcacac agaccttgga agcccatatc   4740
ataaccgccg tggatacaga tagcccaatc agcttggaca tcacaatctt gagctcggtt   4800
aagacaaaag ttcgggactt catcgaaatc atcgctttct tgcaaaattt ttcgcatgcg   4860
gcacatcctc tcctcatgtc gggcagcgtc tctaacaccc aacacaggac aacaactgtg   4920
cacccttta tcccttcttg aaaagtgatg ccaccaagac cctccgaaat ctataacggg   4980
gtcttcaggg ggaaaactgt cgagacagtc ataatgctcc gctacacgca gagcaccagc   5040
caggctatgg ggcgcatgat actgctgagt caaatttaag tcaaaggcac caccataacg   5100
gtcacggaag gcgtcagcct cctcaataga gagcttattg cgaacgttga ttttcttaga   5160
ccttttcgcg tattcaatct gcgcagataa ctgttgcgca acctgattgt ctacgatgtc   5220
ttgggcactc tggctgtcag caccttctc agcaatcaac ttcagcaaat cgatagaact   5280
tgacattttg ttggtgaaaa acaaagaaca agtagcagaa ccgtggtcga ggtcctctcc   5340
aaatgaaatg aacttcctta tatagaggaa gggtcttgcg aaggatagtg ggattgtgcg   5400
tcatccctta cgtcagtgga gatatcacat caatccactt gctttgaaga cgtggttgga   5460
acgtcttctt tttccacgat gttcctcgtg ggtgggggtc catctttggg accactgtcg   5520
gtagaggcat tcttgaacga tagcctttcc tttatcgcaa tgatggcatt tgtagaagcc   5580
atcttccttt tctactgtcc tttcgatgaa gtgacagata gctgggcaat ggaatccgag   5640
gaggtttccc gatattaccc tttgttgaaa agtctcaata gccctctggt cttctgagac   5700
tgtatctttg atattcttgg agtagacgag agtgtcgtgc tccaccatgt tgaccgggtg   5760
gtcagtccct tatgttacgt cctgtagaaa ccccaacccg tgaaatcaaa aaactcgacg   5820
gcctgtgggc attcagtctg gatcgcgaaa actgtggaat tgatcagcgt tggtgggaaa   5880
gcgcgttaca agaaagccgg gcaattgctg tgccaggcag ttttaacgat cagttcgccg   5940
atgcagatat tcgtaattat gcgggcaacg tctggtatca gcgcgaagtc tttataccga   6000
aaggttgggc aggccagcgt atcgtgctgc gtttcgatgc ggtcactcat tacggcaaag   6060
tgtgggtcaa taatcaggaa gtgatggagc atcagggcgg ctatacgcca tttgaagccg   6120
atgtcacgcc gtatgttatt gccgggaaaa gtgtacaatt cactggccgt cgttttacaa   6180
```

```
cgtcgtgact gggaaaaccc tggcgttacc caacttaatc gccttgcagc acatccccct   6240
ttcgccagct ggcgtaatag cgaagaggcc cgcaccgatc gcccttccca acagttgcgc   6300
agcctgaatg gcgaatgnnn nnnnaattca gtacattaaa aacgtccgca atgtgttatt   6360
aagttgtcta agcgtcaatt tgtttacacc acaatatatc ctgccaccag ccagccaaca   6420
gctccccgac cggcagctcg gcacaaaatc accactcgat acaggcagcc catcagnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnnnnnnnnn   6660
nnnnnnnnnn nnnnnnnnnn nnnnnnnnnn nnnnnnnnnn nnnnnnnnnn nnnnnnnnnn   6720
nnnnnnnnnn nnnnnnnnnn nnnnnnnnnn nnnnnnnnnn nnnnnnnnnn nnnnnnnnnn   6780
nnnnnnnnnn nnnnnnnnnn nnnnnnnnnn nnnnnnnnnn nnnnnnnnnn nnnnnnnnnn   6840
nnnnnnnnnn nnnnnnnnnn nnnnnnnnnn nnnnnnnnnn nnnnnnnnnn nnnnnnnnnn   6900
nnnnnnnnnn nnnnnnnnnn nnnnnnnnnn nnnnnnnnnn nnnnnnnnnn nnnnnnnnnn   6960
nnnnnnnnnn nnnnnnnnnn nnnnnnnnnn nnnnnnnnnn nnnnnnnnnn nnnnnnnnnn   7020
nnnnnnnnnn nnnnnnnnnn nnnnnnnnnn nnnnnnnnnn nnnnnnnnnn nnnn         7074
```

<210> SEQ ID NO 2
<211> LENGTH: 6750
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (6318)..(6324)
<223> OTHER INFORMATION: 7 nucleotides which are unknown.
<220> FEATURE:
<221> NAME/KEY: unsure
<222> LOCATION: (6477)..(6750)
<223> OTHER INFORMATION: 274 nucleotides which are unknown.

<400> SEQUENCE: 2

```
aaacactgat agtttaaact gaaggcggga aacgacaatc tgatcatgag cggagaatta     60
agggagtcac gttatgaccc ccgccgatga cgcgggacaa gccgttttac gtttggaact    120
gacagaaccg caacgattga aggagccact cagccgcggg tttctggagt ttaatgagct    180
aagcacatac gtcagaaacc attattgcgc gttcaaaagt cgcctaaggt cactatcagc    240
tagcaaatat ttcttgtcaa aaatgctcca ctgacgttcc ataaattccc ctcggtatcc    300
aattagnnnn nnnnnnnnnn nnnnnnnnnn gatcgtttcg catgattgaa caagatggat    360
tgcacgcagg ttctccggcc gcttgggtgg agaggctatt cggctatgac tgggcacaac    420
agacaatcgg ctgctctgat gccgccgtgt tccggctgtc agcgcagggg cgcccggttc    480
tttttgtcaa gaccgacctg tccggtgccc tgaatgaact gcaggacgag gcagcgcggc    540
tatcgtggct ggccacgacg ggcgttcctt gcgcagctgt gctcgacgtt gtcactgaag    600
cgggaaggga ctggctgcta ttgggcgaag tgccggggca ggatctcctg tcatctcacc    660
ttgctcctgc cgagaaagta tccatcatgg ctgatgcaat gcggcggctg catacgcttg    720
atccggctac ctgcccattc gaccaccaag cgaaacatcg catcgagcga gcacgtactc    780
```

-continued

```
ggatggaagc cggtcttgtc gatcaggatg atctggacga agagcatcag gggctcgcgc    840
cagccgaact gttcgccagg ctcaaggcgc gcatgcccga cggcgatgat ctcgtcgtga    900
cccatggcga tgcctgcttg ccgaatatca tggtggaaaa tggccgcttt tctggattca    960
tcgactgtgg ccggctgggt gtggcggacc gctatcagga catagcgttg gctacccgtg   1020
atattgctga agagcttggc ggcgaatggg ctgaccgctt cctcgtgctt tacggtatcg   1080
ccgctcccga ttcgcagcgc atcgccttct atcgccttct tgacgagttc ttctgannnn   1140
nnnnnnnnnn nnnnnnnnnn gatcgttcaa acatttggca ataaagtttc ttaagattga   1200
atcctgttgc cggtcttgcg atgattatca tataatttct gttgaattac gttaagcatg   1260
taataattaa catgtaatgc atgacgttat ttatgagatg ggtttttatg attagagtcc   1320
cgcaattata catttaatac gcgatagaaa acaaaatata gcgcgcaaac taggataaat   1380
tatcgcgcgc ggtgtcatct atgttactag atcgggcctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgcatgc   2100
ctgcaggtcg actctagagg atccccggtc aacatggtgg agcacgacac tctcgtctac   2160
tccaagaata tcaaagatac agtctcagaa gaccagaggg ctattgagac ttttcaacaa   2220
agggtaatat cgggaaacct cctcggattc cattgcccag ctatctgtca cttcatcgaa   2280
aggacagtag aaaaggaaga tggcttctac aaatgccatc attgcgataa aggaaaggct   2340
atcgttcaag aatgcctcta ccgacagtgg tcccaaagat ggacccccac ccacgaggaa   2400
catcgtggaa aaagaagacg ttccaaccac gtcttcaaag caagtggatt gatgtgatat   2460
ctccactgac gtaagggatg acgcacaatc ccactatcct tcgcaagacc cttcctctat   2520
ataaggaagt tcatttcatt tggagaggac ctcgaccacg gttctgctac ttgttctttg   2580
tttttcacca acaaaatgtc aagttctatc gatttgctga agttgattgc tgagaagggt   2640
gctgacagcc agagtgccca agacatcgta gacaatcagg ttgcgcaaca gttatctgcg   2700
cagattgaat acgcgaaaag gtctaagaaa atcaacgttc gcaataagct ctctattgag   2760
gaggctgacg ccttccgtga ccgttatggt ggtgcctttg acttaaattt gactcagcag   2820
tatcatgcgc cccatagcct ggctggtgct ctgcgtgtag cggagcatta tgactgtctc   2880
gacagttttc cccctgaaga ccccgttata gatttcggag ggtcttggtg gcatcacttt   2940
tcaagaaggg ataaaagggt gcacagttgt tgtcctgtgt tgggtgttag agacgctgcc   3000
cgacatgagg agaggatgtg ccgcatgcga aaaattttgc aagaaagcga tgatttcgat   3060
gaagtcccga acttttgtct taaccgagct caagattgtg atgtccaagc tgattgggct   3120
```

-continued

```
atctgtatcc acggcggtta tgatatgggc ttccaaggtc tgtgtgacgc catgcattcg   3180
catggagtac gcgtactacg tggtaccgtt atgttcgacg gcgccatgtt gtttgaccgc   3240
gagggttttc ttcccttgct taaatgtcac tggcaacgtg acgggtcagg cgcggatgag   3300
gtgatcaaat tcgattttga aaatgaaagc acattatctt acatccacgg atggcaagat   3360
ttgggctcat ttttcaccga gtcggtgcat tgcatcgatg gaaccaccta tctgttggag   3420
cgcgaaatgc tgaaatgtaa catcatgacc tataagatca tcgctacaaa tttacgctgc   3480
ccccgggaga cactacgtca ctgtgtatgg tttgaagaca tatctaagta cgtaggggtc   3540
tcaatacctg aagactggag tctcaatcgc tggaaatgtg tgcgcgtcgc caaaaccaca   3600
gtgagagagg tagaggagat agctttcaga tgtttcaagg aaagtaaaga atggactgag   3660
aacatgaaag ctgtcgcatc tatcttatcc gccaagtcgt cgactgttat tattaacggt   3720
caggctatca tggctggtga gcgcttagac attgaagatt atcatctagt ggcctttgct   3780
ttgactttga atctgtatca aaagtacgaa aagcttacgg ccctccgcga tgggatggaa   3840
tggaaaggtt ggtgccatca cttcaaaact aggttttggt ggggtggaga ttcatccagg   3900
gcgaaagtag gatggctgag aacattggct agcagatttc ccctactacg tctggattct   3960
tatgcggaca gttttaagtt tctgactcgt ctctcaaacg ttgaagaatt tgagcaagat   4020
tctgtaccga tatcacgttt gagaacgttt tggactgaag aggacttatt cgaccggctg   4080
gagcatgaag tgcagacagc caagaccaag cgctcgaaga agaaggcgaa agtcccgcca   4140
gctgctgaga tacctcagga ggagtttcat gatgcccctg agagttcgag ccctgagtcc   4200
gtcagtgatg acgttaaacc ggtgactgat gtggtcccgg atgccgaggt gtctgttgag   4260
gtaccaacgg accctcgtgg catatctaga cacggagcca tgaaggaatt tgtgcgttat   4320
tgtaagagat tacataacaa ctccgagtct aatcttcgtc acctatggga catttccggc   4380
ggtcgcggaa gtgagatcgc aaataagagc atctttgaga cctaccatcg catagacgat   4440
atggtgaatg tccatttggc caacggtaac tggttgtatc ctaaaaaata cgattacact   4500
gttggatata atgagcatgg tttaggtccg aagcacgcag atgaaacgta cattgttgat   4560
aaaacatgtg catgctctaa cttgagggac attgcagaag ctagcgccaa agtttctgtc   4620
cctacatgcg atatttccat ggttgatgga gttgcgggat gcggtaaaac cactgccata   4680
aaagatgcat tccgtatggg agaggaccta attgtgacgg cgaatcgtaa atcggccgag   4740
gacgtcagga tggctttatt ccctgacact tataattcca aggtagcttt ggacgttgtg   4800
cgcaccgcgg attctgcgat catgcacggt gtaccgtcct gtcataggct gcttgttgat   4860
gaggctggtt tactacatta tggtcaactc ctggtggtgg ctgctctgtc taaatgttca   4920
caagttcttg cctttgggga cacagagcag atttcgttca agtctcgtga cgcgggtttt   4980
aaattgctcc acggtaatct gcaatatgat cgccgtgacg ttgttcacaa gacttaccgg   5040
tgtccgcaag atgttatcgc tgctgttaat ctgctgaagc gtaaatgcgg taatagggac   5100
acgaagtatc aatcctggac atctgagtcc aaagtttcta gaagtctcac gaagcgtcgt   5160
attacttctg gtttgcaggt cactattgat ccgaacagaa cgtatcttac gatgactcaa   5220
gctgataaag cggcccttca aacgagggct aaggattttc ccgtgagcaa ggactggatt   5280
gatggacaca taaaaacagt acacgaagcg caagggatct ctgttgacaa cgtcactttg   5340
gttcggctta agtcgaccaa atgtgatttg tttaaacatg aggagtactg tttggttgcc   5400
ttaacacgac acaagaagtc ctttgagtat tgctttaacg gcgagctcgc tggtgatttg   5460
atctttaatt gtgttaagtg atgcgcttgt ctctgtgtga gacctctgct cgagaattcg   5520
```

agctcggtac ccggggatcc tctagagtcc gcaaatcacc agtctctctc tacaaatcta 5580
tctctctcta ttttctccag aataatgtgt gagtagttcc cagataaggg aattagggtt 5640
cttatagggt ttcgctcatg tgttgagcat ataagaaacc cttagtatgt atttgtattt 5700
gtaaaatact tctatcaata aaatttctaa ttcctaaaac caaaatccag tgaccgggtg 5760
gtcagtccct tatgttacgt cctgtagaaa ccccaacccg tgaaatcaaa aaactcgacg 5820
gcctgtgggc attcagtctg gatcgcgaaa actgtggaat tgatcagcgt tggtgggaaa 5880
gcgcgttaca agaaagccgg gcaattgctg tgccaggcag ttttaacgat cagttcgccg 5940
atgcagatat tcgtaattat gcgggcaacg tctggtatca gcgcgaagtc tttataccga 6000
aaggttgggc aggccagcgt atcgtgctgc gtttcgatgc ggtcactcat tacggcaaag 6060
tgtgggtcaa taatcaggaa gtgatggagc atcagggcgg ctatacgcca tttgaagccg 6120
atgtcacgcc gtatgttatt gccgggaaaa gtgtacaatt cactggccgt cgttttacaa 6180
cgtcgtgact gggaaaaccc tggcgttacc caacttaatc gccttgcagc acatccccct 6240
ttcgccagct ggcgtaatag cgaagaggcc cgcaccgatc gcccttccca acagttgcgc 6300
agcctgaatg gcgaatgnnn nnnnaattca gtacattaaa aacgtccgca atgtgttatt 6360
aagttgtcta agcgtcaatt tgtttacacc acaatatatc ctgccaccag ccagccaaca 6420
gctccccgac cggcagctcg gcacaaaatc accactcgat acaggcagcc catcagnnnn 6480
nnnnnnnnnn nnnnnnnnnn nnnnnnnnnn nnnnnnnnnn nnnnnnnnnn nnnnnnnnnn 6540
nnnnnnnnnn nnnnnnnnnn nnnnnnnnnn nnnnnnnnnn nnnnnnnnnn nnnnnnnnnn 6600
nnnnnnnnnn nnnnnnnnnn nnnnnnnnnn nnnnnnnnnn nnnnnnnnnn nnnnnnnnnn 6660
nnnnnnnnnn nnnnnnnnnn nnnnnnnnnn nnnnnnnnnn nnnnnnnnnn nnnnnnnnnn 6720
nnnnnnnnnn nnnnnnnnnn nnnnnnnnnn 6750

<210> SEQ ID NO 3
<211> LENGTH: 6426
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (6169)..(6426)
<223> OTHER INFORMATION: 258 nucleotides which are unknown.
[

<400> SEQUENCE: 3
aaacactgat agtttaaact gaaggcggga aacgacaatc tgatcatgag cggagaatta 60
agggagtcac gttatgaccc ccgccgatga cgcgggacaa gccgttttac gtttggaact 120
gacagaaccg caacgattga aggagccact cagccgcggg tttctggagt ttaatgagct 180
aagcacatac gtcagaaacc attattgcgc gttcaaaagt cgcctaaggt cactatcagc 240
tagcaaatat ttcttgtcaa aaatgctcca ctgacgttcc ataaattccc ctcggtatcc 300
aattagnnnn nnnnnnnnnn nnnnnnnnnn gatcgtttcg catgattgaa caagatggat 360
tgcacgcagg ttctccggcc gcttgggtgg agaggctatt cggctatgac tgggcacaac 420
agacaatcgg ctgctctgat gccgccgtgt tccggctgtc agcgcagggg cgcccggttc 480

```
tttttgtcaa gaccgacctg tccggtgccc tgaatgaact gcaggacgag gcagcgcggc    540
tatcgtggct ggccacgacg ggcgttcctt gcgcagctgt gctcgacgtt gtcactgaag    600
cgggaaggga ctggctgcta ttgggcgaag tgccggggca ggatctcctg tcatctcacc    660
ttgctcctgc cgagaaagta tccatcatgg ctgatgcaat gcggcggctg catacgcttg    720
atccggctac ctgcccattc gaccaccaag cgaaacatcg catcgagcga gcacgtactc    780
ggatggaagc cggtcttgtc gatcaggatg atctggacga agagcatcag gggctcgcgc    840
cagccgaact gttcgccagg ctcaaggcgc gcatgcccga cggcgatgat ctcgtcgtga    900
cccatggcga tgcctgcttg ccgaatatca tggtggaaaa tggccgcttt tctggattca    960
tcgactgtgg ccggctgggt gtggcggacc gctatcagga catagcgttg gctacccgtg   1020
atattgctga agagcttggc ggcgaatggg ctgaccgctt cctcgtgctt tacggtatcg   1080
ccgctcccga ttcgcagcgc atcgccttct atcgccttct tgacgagttc ttctgannnn   1140
nnnnnnnnnn nnnnnnnnnn gatcgttcaa acatttggca ataaagtttc ttaagattga   1200
atcctgttgc cggtcttgcg atgattatca tataatttct gttgaattac gttaagcatg   1260
taataattaa catgtaatgc atgacgttat ttatgagatg ggtttttatg attagagtcc   1320
cgcaattata catttaatac gcgatagaaa acaaaatata gcgcgcaaac taggataaat   1380
tatcgcgcgc ggtgtcatct atgttactag atcgggcctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgcatgc   2100
ctgcaggtca ctggattttg gttttaggaa ttagaaattt tattgataga agtattttac   2160
aaatacaaat acatactaag ggtttcttat atgctcaaca catgagcgaa accctataag   2220
aaccctaatt cccttatctg ggaactactc acacattatt ctggagaaaa tagagagaga   2280
tagatttgta gagagagact ggtgatttgc ggactctaga ggatccccag cttttaaact   2340
tagccaaagt ggtctgcctg accaggagtt tttaacctta accaaagggc tgttcacagc   2400
ttaggttcat atatcataga accgatcatc tcagatcaga gggcttaaaa gtctcacaat   2460
gggacttcac gagcaaagca tcaactgacg ttaggcctcc tctaccggta gcgtaatcgt   2520
cgaccttctt tttcaagcgt tgtgtggtcc tacgatcatt agctaatttg agtgactcac   2580
gctcaagggc ctcatgtaaa cgtccgatcc gtttgacagg gagctcctta gtactacagt   2640
ccgaggaata aattccaatg gttctgtaga ctttgtctaa cacaccagga aactttggat   2700
tcttccagtt gtgaaaccag tcaccatcag ttttacgctc ttccgtggtg cgtttgaact   2760
tacatacagg atcgctcatc tgataaactc tgatgccttc ggtacagtag caatcagaga   2820
```

-continued

```
acctcaggaa attctcggag tataaagaaa aagccgcaag agcagctcta acctcctcga   2880
aaatccaagg tttttctttc ccatatttca gataaacaaa atgacagagc gtcgtaatca   2940
tcttctcatc aagttgatta ataaacttca ttcgatcaca gaaggaaacg aaatgtgctc   3000
tgagcatctg ttcatcacgc agaatctttc gcttagctaa gcgctggatc tctctcagag   3060
gatctggtac agacaccaaa ttgcccattt cagtttcgac gagaaactta ctacaaacgt   3120
agggcacact agggtccatg acttttatct ccatattgaa gagagacgta aacatatcgg   3180
tatccaggac tggcttaact ttagagatga ttaaagaatc atctcctgaa aatattgcac   3240
agtcacagtc acttagatca gaggcatatg caatcatagc catagtgaca agagtattac   3300
cgaaatatgt aaacgcgtca ccagttctgc gttggaagga aacggacatt cccaccttgg   3360
catgagggtc tgataaataa gaatcgcgat gaaaatcaga ccaccaattc gtcagcggcg   3420
ctggaaagcc cagcgcaagg agtatctctc tctgaaactc taggtgcagc tcaccctgag   3480
atttatcaaa tttgcttagg tccgcttcaa gaaagtatct gttattcaag cggacattct   3540
taagctccag agaggatatc tttccgatag gcacaatgaa cctggatttc agggccagtg   3600
ataacttctc gaaacaagca gtgaaaaagg gtgaaaaatt actagtcaca cctttactat   3660
gaaatgttat agtagctgct actgctcgtt ccaagtgaag ggtgtcagtt acaacaggtt   3720
ttacgtcaga cttcagcata tgctggtacc gacataaatc agtctctgct gccacattca   3780
caccttgcaa gtccatgtgc ttaccccact tcttatggta ctcaagacat ttagtcatga   3840
catccataga agctctcaga cagtcttcac cgtcaacatt aaggaatgtg ctacgaaagc   3900
gctttgctat agctttcgca gtgtccttca tgttaatcgc gtctcccatt tctggaacgt   3960
ccgcgtttcg ctttttgagt gcggttaaga cttctttctg agtaccaact cttcgctgag   4020
cactcccgat attcattttt ggttgaaaat atttatcggg gtccctatac cagtctacat   4080
cactttgctt aagtctgatc ctatcaaagt ccatggaata atcaccattt tcaacaaggg   4140
cttgatggta cgaatcatcg aaataagcat gggttggcag tatggaatga ctggtcgctt   4200
ctgttctagc aaggctgact ctctccatat aaattggccc agtagagatg tcagggttat   4260
ctggatggca gtgtgtatca ataacacgcg aaaccctatg ttcaataggg ttcatgattt   4320
gaagagtgat gtcgtaatca gtattagtag tctgaaactc ttcatcaatg cccatgtacc   4380
tatctccaag ggtcagctcc ttgggggtat ctccagtaac acgaacttcc tcaatttcac   4440
agttcgagga atcactggcg agttttagat cgctcgcatg atcttcatcg gcggcaaacg   4500
atacaccgta accatcacta gtatcctcgg gataccagtc atcaatttca tcttcgagca   4560
cgaaagagcc cggaatgtca agatataaca tccgtgccat ttcagcttga ggaatcagcg   4620
gtctatcggt gaactgttga accatttgtt ggacggtgtc gcaaatagag ccccagcgca   4680
ctcggtcaaa agggggatcg aataccccctc ctatctccaa gggcgctata gctaatttaa   4740
aactcgcgag agatccgtca atggcaactc cgtctgccgg ctcctgcacc tgaaggctag   4800
cagcctccac ctcgtcttct aaggattgat ctatgatcca ttggaaagac gggacctggc   4860
gaacgaaatc atcatcccag gttttcgaag acatcttggt gatagtagaa agaacaagca   4920
cacaacaaca acaaggtcag atgtgtgttg cgggtaccga gctcgaattc tcgaggtcct   4980
ctccaaatga aatgaacttc cttatataga ggaagggtct tgcgaaggat agtgggattg   5040
tgcgtcatcc cttacgtcag tggagatatc acatcaatcc acttgctttg aagacgtggt   5100
tggaacgtct tctttttcca cgatgttcct cgtgggtggg ggtccatctt tgggaccact   5160
gtcggtagag gcattcttga acgatagcct ttcctttatc gcaatgatgg catttgtaga   5220
```

-continued

```
agccatcttc cttttctact gtcctttcga tgaagtgaca gatagctggg caatggaatc   5280

cgaggaggtt tcccgatatt accctttgtt gaaaagtctc aatagccctc tggtcttctg   5340

agactgtatc tttgatattc ttggagtaga cgagagtgtc gtgctccacc atgttgacct   5400

gcaggcagca agcttgcatg cctgcaggtc gactctagag gatccccggg tggtcagtcc   5460

cttatgttac gtcctgtaga aaccccaacc cgtgaaatca aaaaactcga cggcctgtgg   5520

gcattcagtc tggatcgcga aaactgtgga attgatcagc gttggtggga aagcgcgtta   5580

caagaaagcc gggcaattgc tgtgccaggc agttttaacg atcagttcgc cgatgcagat   5640

attcgtaatt atgcgggcaa cgtctggtat cagcgcgaag tctttatacc gaaaggttgg   5700

gcaggccagc gtatcgtgct gcgtttcgat gcggtcactc attacggcaa agtgtgggtc   5760

aataatcagg aagtgatgga gcatcagggc ggctatacgc catttgaagc cgatgtcacg   5820

ccgtatgtta ttgccgggaa aagtgtacaa ttcactggcc gtcgttttac aacgtcgtga   5880

ctgggaaaac cctggcgtta cccaacttaa tcgccttgca gcacatcccc ctttcgccag   5940

ctggcgtaat agcgaagagg cccgcaccga tcgcccttcc caacagttgc gcagcctgaa   6000

tggcgaatgn nnnnnnaatt cagtacatta aaaacgtccg caatgtgtta ttaagttgtc   6060

taagcgtcaa tttgtttaca ccacaatata tcctgccacc agccagccaa cagctccccg   6120

accggcagct cggcacaaaa tcaccactcg atacaggcag cccatcagnn nnnnnnnnnn   6180

nnnnnnnnnn nnnnnnnnnn nnnnnnnnnn nnnnnnnnnn nnnnnnnnnn nnnnnnnnnn   6240

nnnnnnnnnn nnnnnnnnnn nnnnnnnnnn nnnnnnnnnn nnnnnnnnnn nnnnnnnnnn   6300

nnnnnnnnnn nnnnnnnnnn nnnnnnnnnn nnnnnnnnnn nnnnnnnnnn nnnnnnnnnn   6360

nnnnnnnnnn nnnnnnnnnn nnnnnnnnnn nnnnnnnnnn nnnnnnnnnn nnnnnnnnnn   6420

nnnnnn                                                               6426


<210> SEQ ID NO 4
<211> LENGTH: 6500
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (6169)..(6500)
<223> OTHER INFORMATION: 332 nucleotides which are unknown.

<400> SEQUENCE: 4

aaacactgat agtttaaact gaaggcggga aacgacaatc tgatcatgag cggagaatta     60

agggagtcac gttatgaccc ccgccgatga cgcgggacaa gccgttttac gtttggaact    120

gacagaaccg caacgattga aggagccact cagccgcggg tttctggagt ttaatgagct    180

aagcacatac gtcagaaacc attattgcgc gttcaaaagt cgcctaaggt cactatcagc    240

tagcaaatat ttcttgtcaa aaatgctcca ctgacgttcc ataaattccc ctcggtatcc    300

aattagnnnn nnnnnnnnnn nnnnnnnnnn gatcgtttcg catgattgaa caagatggat    360

tgcacgcagg ttctccggcc gcttgggtgg agaggctatt cggctatgac tgggcacaac    420

agacaatcgg ctgctctgat gccgccgtgt tccggctgtc agcgcagggg cgcccggttc    480
```

```
tttttgtcaa gaccgacctg tccggtgccc tgaatgaact gcaggacgag gcagcgcggc    540
tatcgtggct ggccacgacg ggcgttcctt gcgcagctgt gctcgacgtt gtcactgaag    600
cgggaaggga ctggctgcta ttgggcgaag tgccggggca ggatctcctg tcatctcacc    660
ttgctcctgc cgagaaagta tccatcatgg ctgatgcaat gcggcggctg catacgcttg    720
atccggctac ctgcccattc gaccaccaag cgaaacatcg catcgagcga gcacgtactc    780
ggatggaagc cggtcttgtc gatcaggatg atctggacga agagcatcag gggctcgcgc    840
cagccgaact gttcgccagg ctcaaggcgc gcatgcccga cggcgatgat ctcgtcgtga    900
cccatggcga tgcctgcttg ccgaatatca tggtggaaaa tggccgcttt tctggattca    960
tcgactgtgg ccggctgggt gtggcggacc gctatcagga catagcgttg gctacccgtg   1020
atattgctga agagcttggc ggcgaatggg ctgaccgctt cctcgtgctt tacggtatcg   1080
ccgctcccga ttcgcagcgc atcgccttct atcgccttct tgacgagttc ttctgannnn   1140
nnnnnnnnnn nnnnnnnnnn gatcgttcaa acatttggca ataaagtttc ttaagattga   1200
atcctgttgc cggtcttgcg atgattatca tataatttct gttgaattac gttaagcatg   1260
taataattaa catgtaatgc atgacgttat ttatgagatg ggtttttatg attagagtcc   1320
cgcaattata catttaatac gcgatagaaa acaaaatata gcgcgcaaac taggataaat   1380
tatcgcgcgc ggtgtcatct atgttactag atcgggcctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgctgcc   2100
tgcaggtcaa catggtggag cacgacactc tcgtctactc caagaatatc aaagatacag   2160
tctcagaaga ccagagggct attgagactt ttcaacaaag ggtaatatcg ggaaacctcc   2220
tcggattcca ttgcccagct atctgtcact tcatcgaaag gacagtagaa aaggaagatg   2280
gcttctacaa atgccatcat tgcgataaag gaaaggctat cgttcaagaa tgcctctacc   2340
gacagtggtc ccaaagatgg acccccaccc acgaggaaca tcgtggaaaa agaagacgtt   2400
ccaaccacgt cttcaaagca agtggattga tgtgatatct ccactgacgt aagggatgac   2460
gcacaatccc actatccttc gcaagaccct tcctctatat aaggaagttc atttcatttg   2520
gagaggacct cgagaattcg agctcggtac ccgcaacaca catctgacct tgttgttgtt   2580
gtgtgcttgt tctttctact atcaccaaga tgtcttcgaa aacctgggat gatgatttcg   2640
ttcgccaggt cccgtctttc caatggatca tagatcaatc cttagaagac gaggtggagg   2700
ctgctagcct tcaggtgcag gagccggcag acggagttgc cattgacgga tctctcgcga   2760
gttttaaatt agctatagcg cccttggaga taggaggggt attcgatccc ccttttgacc   2820
gagtgcgctg ggctctattt tgcgacaccg tccaacaaat ggttcaacag ttcaccgata   2880
```

-continued

```
gaccgctgat tcctcaagct gaaatggcac ggatgttata tcttgacatt ccgggctctt   2940
tcgtgctcga agatgaaatt gatgactggt atcccgagga tactagtgat ggttacggtg   3000
tatcgtttgc cgccgatgaa gatcatgcga gcgatctaaa actcgccagt gattcctcga   3060
actgtgaaat tgaggaagtt cgtgttactg gagatacccc caaggagctg acccttggag   3120
ataggtacat gggcattgat gaagagtttc agactactaa tactgattac gacatcactc   3180
ttcaaatcat gaaccctatt gaacataggg tttcgcgtgt tattgataca cactgccatc   3240
cagataaccc tgacatctct actgggccaa tttatatgga gagagtcagc cttgctagaa   3300
cagaagcgac cagtcattcc atactgccaa cccatgctta tttcgatgat tcgtaccatc   3360
aagcccttgt tgaaaatggt gattattcca tggactttga taggatcaga cttaagcaaa   3420
gtgatgtaga ctggtatagg gaccccgata aatattttca accaaaaatg aatatcggga   3480
gtgctcagcg aagagttggt actcagaaag aagtcttaac cgcactcaaa aagcgaaacg   3540
cggacgttcc agaaatggga gacgcgatta acatgaagga cactgcgaaa gctatagcaa   3600
agcgctttcg tagcacattc cttaatgttg acggtgaaga ctgtctgaga gcttctatgg   3660
atgtcatgac taaatgtctt gagtaccata agaagtgggg taagcacatg gacttgcaag   3720
gtgtgaatgt ggcagcagag actgatttat gtcggtacca gcatatgctg aagtctgacg   3780
taaaacctgt tgtaactgac acccttcact tggaacgagc agtagcagct actataacat   3840
ttcatagtaa aggtgtgact agtaattttt cacccttttt cactgcttgt ttcgagaagt   3900
tatcactggc cctgaaatcc aggttcattg tgcctatcgg aaagatatcc tctctggagc   3960
ttaagaatgt ccgcttgaat aacagatact ttcttgaagc ggacctaagc aaatttgata   4020
aatctcaggg tgagctgcac ctagagtttc agagagagat actccttgcg ctgggctttc   4080
cagcgccgct gacgaattgg tggtctgatt ttcatcgcga ttcttattta tcagaccctc   4140
atgccaaggt gggaatgtcc gtttccttcc aacgcagaac tggtgacgcg tttacatatt   4200
tcggtaatac tcttgtcact atggctatga ttgcatatgc ctctgatcta agtgactgtg   4260
actgtgcaat attttcagga gatgattctt taatcatctc taaagttaag ccagtcctgg   4320
ataccgatat gtttacgtct ctcttcaata tggagataaa agtcatggac cctagtgtgc   4380
cctacgtttg tagtaagttt ctcgtcgaaa ctgaaatggg caatttggtg tctgtaccag   4440
atcctctgag agagatccag cgcttagcta agcgaaagat tctgcgtgat gaacagatgc   4500
tcagagcaca tttcgtttcc ttctgtgatc gaatgaagtt tattaatcaa cttgatgaga   4560
agatgattac gacgctctgt cattttgttt atctgaaata tgggaaagaa aaaccttgga   4620
ttttcgagga ggttagagct gctcttgcgg ctttttcttt atactccgag aatttcctga   4680
ggttctctga ttgctactgt accgaaggca tcagagttta tcagatgagc gatcctgtat   4740
gtaagttcaa acgcaccacg gaagagcgta aaactgatgg tgactggttt cacaactgga   4800
agaatccaaa gtttcctggt gtgttagaca aagtctacag aaccattgga atttattcct   4860
cggactgtag tactaaggag ctccctgtca aacggatcgg acgtttacat gaggcccttg   4920
agcgtgagtc actcaaatta gctaatgatc gtaggaccac acaacgcttg aaaaagaagg   4980
tcgacgatta cgctaccggt agaggaggcc taacgtcagt tgatgctttg ctcgtgaagt   5040
cccattgtga gacttttaag ccctctgatc tgagatgatc ggttctatga tatatgaacc   5100
taagctgtga acagcccttt ggttaaggtt aaaaactcct ggtcaggcag accactttgg   5160
ctaagtttaa aagctgggga tcctctagag tccgcaaatc accagtctct ctctacaaat   5220
```

```
ctatctctct ctattttctc cagaataatg tgtgagtagt tcccagataa gggaattagg   5280

gttcttatag ggtttcgctc atgtgttgag catataagaa acccttagta tgtatttgta   5340

tttgtaaaat acttctatca ataaaatttc taattcctaa aaccaaaatc cagtgacctg   5400

caggcatgca agcttgcatg cctgcaggtc gactctagag gatccccggg tggtcagtcc   5460

cttatgttac gtcctgtaga aaccccaacc cgtgaaatca aaaaactcga cggcctgtgg   5520

gcattcagtc tggatcgcga aaactgtgga attgatcagc gttggtggga aagcgcgtta   5580

caagaaagcc gggcaattgc tgtgccaggc agttttaacg atcagttcgc cgatgcagat   5640

attcgtaatt atgcgggcaa cgtctggtat cagcgcgaag tctttatacc gaaaggttgg   5700

gcaggccagc gtatcgtgct gcgtttcgat gcggtcactc attacggcaa agtgtgggtc   5760

aataatcagg aagtgatgga gcatcagggc ggctatacgc catttgaagc cgatgtcacg   5820

ccgtatgtta ttgccgggaa aagtgtacaa ttcactggcc gtcgttttac aacgtcgtga   5880

ctgggaaaac cctggcgtta cccaacttaa tcgccttgca gcacatcccc ctttcgccag   5940

ctggcgtaat agcgaagagg cccgcaccga tcgcccttcc caacagttgc gcagcctgaa   6000

tggcgaatgn nnnnnnaatt cagtacatta aaaacgtccg caatgtgtta ttaagttgtc   6060

taagcgtcaa tttgtttaca ccacaatata tcctgccacc agccagccaa cagctccccg   6120

accggcagct cggcacaaaa tcaccactcg atacaggcag cccatcagnn nnnnnnnnnn   6180

nnnnnnnnnn nnnnnnnnnn nnnnnnnnnn nnnnnnnnnn nnnnnnnnnn nnnnnnnnnn   6240

nnnnnnnnnn nnnnnnnnnn nnnnnnnnnn nnnnnnnnnn nnnnnnnnnn nnnnnnnnnn   6300

nnnnnnnnnn nnnnnnnnnn nnnnnnnnnn nnnnnnnnnn nnnnnnnnnn nnnnnnnnnn   6360

nnnnnnnnnn nnnnnnnnnn nnnnnnnnnn nnnnnnnnnn nnnnnnnnnn nnnnnnnnnn   6420

nnnnnnnnnn nnnnnnnnnn nnnnnnnnnn nnnnnnnnnn nnnnnnnnnn nnnnnnnnnn   6480

nnnnnnnnnn nnnnnnnnnn                                                 6500


<210> SEQ ID NO 5
<211> LENGTH: 10100
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (9639)..(9645)
<223> OTHER INFORMATION: 7 nucleotides which are unknown.
<220> FEATURE:
<221> NAME/KEY: unsure
<222> LOCATION: (9798)..(10100)
<223> OTHER INFORMATION: 303 nucleotides which are unknown.

<400> SEQUENCE: 5

aaacactgat agtttaaact gaaggcggga aacgacaatc tgatcatgag cggagaatta     60

agggagtcac gttatgaccc ccgccgatga cgcgggacaa gccgttttac gtttggaact    120

gacagaaccg caacgattga aggagccact cagccgcggg tttctggagt ttaatgagct    180

aagcacatac gtcagaaacc attattgcgc gttcaaaagt cgcctaaggt cactatcagc    240

tagcaaatat ttcttgtcaa aaatgctcca ctgacgttcc ataaattccc ctcggtatcc    300

aattagnnnn nnnnnnnnnn nnnnnnnnnn gatcgtttcg catgattgaa caagatggat    360
```

-continued

```
tgcacgcagg ttctccggcc gcttgggtgg agaggctatt cggctatgac tgggcacaac    420
agacaatcgg ctgctctgat gccgccgtgt tccggctgtc agcgcagggg cgcccggttc    480
tttttgtcaa gaccgacctg tccggtgccc tgaatgaact gcaggacgag gcagcgcggc    540
tatcgtggct ggccacgacg ggcgttcctt gcgcagctgt gctcgacgtt gtcactgaag    600
cgggaaggga ctggctgcta ttgggcgaag tgccggggca ggatctcctg tcatctcacc    660
ttgctcctgc cgagaaagta tccatcatgg ctgatgcaat gcggcggctg catacgcttg    720
atccggctac ctgcccattc gaccaccaag cgaaacatcg catcgagcga gcacgtactc    780
ggatggaagc cggtcttgtc gatcaggatg atctggacga agagcatcag gggctcgcgc    840
cagccgaact gttcgccagg ctcaaggcgc gcatgcccga cggcgatgat ctcgtcgtga    900
cccatggcga tgcctgcttg ccgaatatca tggtggaaaa tggccgcttt tctggattca    960
tcgactgtgg ccggctgggt gtggcggacc gctatcagga catagcgttg gctacccgtg   1020
atattgctga agagcttggc ggcgaatggg ctgaccgctt cctcgtgctt tacggtatcg   1080
ccgctcccga ttcgcagcgc atcgccttct atcgccttct tgacgagttc ttctgannnn   1140
nnnnnnnnnn nnnnnnnnnn gatcgttcaa acatttggca ataaagtttc ttaagattga   1200
atcctgttgc cggtcttgcg atgattatca tataatttct gttgaattac gttaagcatg   1260
taataattaa catgtaatgc atgacgttat ttatgagatg ggtttttatg attagagtcc   1320
cgcaattata catttaatac gcgatagaaa acaaaatata gcgcgcaaac taggataaat   1380
tatcgcgcgc ggtgtcatct atgttactag atcgggcctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgcatgc   2100
ctgcaggtca ctggattttg gttttaggaa ttagaaattt tattgataga agtattttac   2160
aaatacaaat acatactaag ggtttcttat atgctcaaca catgagcgaa accctataag   2220
aaccctaatt cccttatctg ggaactactc acacattatt ctggagaaaa tagagagaga   2280
tagatttgta gagagagact ggtgatttgc ggactctaga ggatccccag cttttaaact   2340
tagccaaagt ggtctgcctg accaggagtt tttaacctta accaaagggc tgttcacagc   2400
ttaggttcat atatcataga accgatcatc tcagatcaga gggcttaaaa gtctcacaat   2460
gggacttcac gagcaaagca tcaactgacg ttaggcctcc tctaccggta gcgtaatcgt   2520
cgaccttctt tttcaagcgt tgtgtggtcc tacgatcatt agctaatttg agtgactcac   2580
gctcaagggc ctcatgtaaa cgtccgatcc gtttgacagg gagctcctta gtactacagt   2640
ccgaggaata aattccaatg gttctgtaga ctttgtctaa cacaccagga aactttggat   2700
```

-continued

```
tcttccagtt gtgaaaccag tcaccatcag ttttacgctc ttccgtggtg cgtttgaact   2760
tacatacagg atcgctcatc tgataaactc tgatgccttc ggtacagtag caatcagaga   2820
acctcaggaa attctcggag tataaagaaa aagccgcaag agcagctcta acctcctcga   2880
aaatccaagg tttttctttc ccatatttca gataaacaaa atgacagagc gtcgtaatca   2940
tcttctcatc aagttgatta ataaacttca ttcgatcaca gaaggaaacg aaatgtgctc   3000
tgagcatctg ttcatcacgc agaatctttc gcttagctaa gcgctggatc tctctcagag   3060
gatctggtac agacaccaaa ttgcccattt cagtttcgac gagaaactta ctacaaacgt   3120
agggcacact agggtccatg acttttatct ccatattgaa gagagacgta aacatatcgg   3180
tatccaggac tggcttaact ttagagatga ttaaagaatc atctcctgaa aatattgcac   3240
agtcacagtc acttagatca gaggcatatg caatcatagc catagtgaca agagtattac   3300
cgaaatatgt aaacgcgtca ccagttctgc gttggaagga aacggacatt cccaccttgg   3360
catgagggtc tgataaataa gaatcgcgat gaaaatcaga ccaccaattc gtcagcggcg   3420
ctggaaagcc cagcgcaagg agtatctctc tctgaaactc taggtgcagc tcaccctgag   3480
atttatcaaa tttgcttagg tccgcttcaa gaaagtatct gttattcaag cggacattct   3540
taagctccag agaggatatc tttccgatag gcacaatgaa cctggatttc agggccagtg   3600
ataacttctc gaaacaagca gtgaaaaagg gtgaaaaatt actagtcaca cctttactat   3660
gaaatgttat agtagctgct actgctcgtt ccaagtgaag ggtgtcagtt acaacaggtt   3720
ttacgtcaga cttcagcata tgctggtacc gacataaatc agtctctgct gccacattca   3780
caccttgcaa gtccatgtgc ttaccccact tcttatggta ctcaagacat ttagtcatga   3840
catccataga agctctcaga cagtcttcac cgtcaacatt aaggaatgtg ctacgaaagc   3900
gctttgctat agctttcgca gtgtccttca tgttaatcgc gtctcccatt tctggaacgt   3960
ccgcgtttcg ctttttgagt gcggttaaga cttctttctg agtaccaact cttcgctgag   4020
cactcccgat attcattttt ggttgaaaat atttatcggg gtccctatac cagtctacat   4080
cactttgctt aagtctgatc ctatcaaagt ccatggaata atcaccattt tcaacaaggg   4140
cttgatggta cgaatcatcg aaataagcat gggttggcag tatggaatga ctggtcgctt   4200
ctgttctagc aaggctgact ctctccatat aaattggccc agtagagatg tcagggttat   4260
ctggatggca gtgtgtatca ataacacgcg aaaccctatg ttcaataggg ttcatgattt   4320
gaagagtgat gtcgtaatca gtattagtag tctgaaactc ttcatcaatg cccatgtacc   4380
tatctccaag ggtcagctcc ttgggggtat ctccagtaac acgaacttcc tcaatttcac   4440
agttcgagga atcactggcg agttttagat cgctcgcatg atcttcatcg gcggcaaacg   4500
atacaccgta accatcacta gtatcctcgg gataccagtc atcaatttca tcttcgagca   4560
cgaaagagcc cggaatgtca agatataaca tccgtgccat ttcagcttga ggaatcagcg   4620
gtctatcggt gaactgttga accatttgtt ggacggtgtc gcaaatagag ccccagcgca   4680
ctcggtcaaa agggggatcg aatacccctc ctatctccaa gggcgctata gctaatttaa   4740
aactcgcgag agatccgtca atggcaactc cgtctgccgg ctcctgcacc tgaaggctag   4800
cagcctccac ctcgtcttct aaggattgat ctatgatcca ttggaaagac gggacctggc   4860
gaacgaaatc atcatcccag gttttcgaag acatcttggt gatagtagaa agaacaagca   4920
cacaacaaca acaaggtcag atgtgtgttg cgggtaccga gctcgaattc tcgaggtcct   4980
ctccaaatga aatgaacttc cttatataga ggaagggtct tgcgaaggat agtgggattg   5040
tgcgtcatcc cttacgtcag tggagatatc acatcaatcc acttgctttg aagacgtggt   5100
```

-continued

```
tggaacgtct tctttttcca cgatgttcct cgtgggtggg ggtccatctt tgggaccact   5160
gtcggtagag gcattcttga acgatagcct ttcctttatc gcaatgatgg catttgtaga   5220
agccatcttc cttttctact gtcctttcga tgaagtgaca gatagctggg caatggaatc   5280
cgaggaggtt tcccgatatt accctttgtt gaaaagtctc aatagccctc tggtcttctg   5340
agactgtatc tttgatattc ttggagtaga cgagagtgtc gtgctccacc atgttgacct   5400
gcaggcagca agcttgcatg cctgcaggtc gactctagag gatccccggt caacatggtg   5460
gagcacgaca ctctcgtcta ctccaagaat atcaaagata cagtctcaga agaccagagg   5520
gctattgaga cttttcaaca aagggtaata tcgggaaacc tcctcggatt ccattgccca   5580
gctatctgtc acttcatcga aaggacagta gaaaaggaag atggcttcta caaatgccat   5640
cattgcgata aaggaaaggc tatcgttcaa gaatgcctct accgacagtg gtcccaaaga   5700
tggaccccca cccacgagga acatcgtgga aaaagaagac gttccaacca cgtcttcaaa   5760
gcaagtggat tgatgtgata tctccactga cgtaagggat gacgcacaat cccactatcc   5820
ttcgcaagac ccttcctcta tataaggaag ttcatttcat ttggagagga cctcgaccac   5880
ggttctgcta cttgttcttt gtttttcacc aacaaaatgt caagttctat cgatttgctg   5940
aagttgattg ctgagaaggg tgctgacagc cagagtgccc aagacatcgt agacaatcag   6000
gttgcgcaac agttatctgc gcagattgaa tacgcgaaaa ggtctaagaa aatcaacgtt   6060
cgcaataagc tctctattga ggaggctgac gccttccgtg accgttatgg tggtgccttt   6120
gacttaaatt tgactcagca gtatcatgcg ccccatagcc tggctggtgc tctgcgtgta   6180
gcggagcatt atgactgtct cgacagtttt ccccctgaag accccgttat agatttcgga   6240
gggtcttggt ggcatcactt ttcaagaagg gataaaaggg tgcacagttg ttgtcctgtg   6300
ttgggtgtta gagacgctgc ccgacatgag gagaggatgt gccgcatgcg aaaaattttg   6360
caagaaagcg atgatttcga tgaagtcccg aacttttgtc ttaaccgagc tcaagattgt   6420
gatgtccaag ctgattgggc tatctgtatc cacggcggtt atgatatggg cttccaaggt   6480
ctgtgtgacg ccatgcattc gcatggagta cgcgtactac gtggtaccgt tatgttcgac   6540
ggcgccatgt tgtttgaccg cgagggtttt cttcccttgc ttaaatgtca ctggcaacgt   6600
gacgggtcag gcgcggatga ggtgatcaaa ttcgattttg aaaatgaaag cacattatct   6660
tacatccacg gatggcaaga tttgggctca tttttcaccg agtcggtgca ttgcatcgat   6720
ggaaccacct atctgttgga gcgcgaaatg ctgaaatgta acatcatgac ctataagatc   6780
atcgctacaa atttacgctg cccccgggag acactacgtc actgtgtatg gtttgaagac   6840
atatctaagt acgtaggggt ctcaatacct gaagactgga gtctcaatcg ctggaaatgt   6900
gtgcgcgtcg ccaaaaccac agtgagagag gtagaggaga tagctttcag atgtttcaag   6960
gaaagtaaag aatggactga gaacatgaaa gctgtcgcat ctatcttatc cgccaagtcg   7020
tcgactgtta ttattaacgg tcaggctatc atggctggtg agcgcttaga cattgaagat   7080
tatcatctag tggcctttgc tttgactttg aatctgtatc aaaagtacga aaagcttacg   7140
gccctccgcg atgggatgga atggaaaggt tggtgccatc acttcaaaac taggttttgg   7200
tggggtggag attcatccag ggcgaaagta ggatggctga gaacattggc tagcagattt   7260
cccctactac gtctggattc ttatgcggac agttttaagt ttctgactcg tctctcaaac   7320
gttgaagaat ttgagcaaga ttctgtaccg atatcacgtt tgagaacgtt ttggactgaa   7380
gaggacttat tcgaccggct ggagcatgaa gtgcagacag ccaagaccaa gcgctcgaag   7440
```

-continued

```
aagaaggcga aagtcccgcc agctgctgag atacctcagg aggagtttca tgatgcccct   7500
gagagttcga gccctgagtc cgtcagtgat gacgttaaac cggtgactga tgtggtcccg   7560
gatgccgagg tgtctgttga ggtaccaacg gaccctcgtg gcatatctag acacggagcc   7620
atgaaggaat ttgtgcgtta ttgtaagaga ttacataaca actccgagtc taatcttcgt   7680
cacctatggg acatttccgg cggtcgcgga agtgagatcg caaataagag catctttgag   7740
acctaccatc gcatagacga tatggtgaat gtccatttgg ccaacggtaa ctggttgtat   7800
cctaaaaaat acgattacac tgttggatat aatgagcatg gtttaggtcc gaagcacgca   7860
gatgaaacgt acattgttga taaaacatgt gcatgctcta acttgaggga cattgcagaa   7920
gctagcgcca aagtttctgt ccctacatgc gatatttcca tggttgatgg agttgcggga   7980
tgcggtaaaa ccactgccat aaaagatgca ttccgtatgg gagaggacct aattgtgacg   8040
gcgaatcgta aatcggccga ggacgtcagg atggctttat tccctgacac ttataattcc   8100
aaggtagctt tggacgttgt gcgcaccgcg gattctgcga tcatgcacgg tgtaccgtcc   8160
tgtcataggc tgcttgttga tgaggctggt ttactacatt atggtcaact cctggtggtg   8220
gctgctctgt ctaaatgttc acaagttctt gcctttgggg acacagagca gatttcgttc   8280
aagtctcgtg acgcgggttt taaattgctc cacggtaatc tgcaatatga tcgccgtgac   8340
gttgttcaca agacttaccg gtgtccgcaa gatgttatcg ctgctgttaa tctgctgaag   8400
cgtaaatgcg gtaataggga cacgaagtat caatcctgga catctgagtc caaagtttct   8460
agaagtctca cgaagcgtcg tattacttct ggtttgcagg tcactattga tccgaacaga   8520
acgtatctta cgatgactca agctgataaa gcggcccttc aaacgagggc taaggatttt   8580
cccgtgagca aggactggat tgatggacac ataaaaacag tacacgaagc gcaagggatc   8640
tctgttgaca acgtcacttt ggttcggctt aagtcgacca aatgtgattt gtttaaacat   8700
gaggagtact gtttggttgc cttaacacga cacaagaagt cctttgagta ttgctttaac   8760
ggcgagctcg ctggtgattt gatctttaat tgtgttaagt gatgcgcttg tctctgtgtg   8820
agacctctgc tcgagaattc gagctcggta cccggggatc ctctagagtc cgcaaatcac   8880
cagtctctct ctacaaatct atctctctct attttctcca gaataatgtg tgagtagttc   8940
ccagataagg gaattagggt tcttataggg tttcgctcat gtgttgagca tataagaaac   9000
ccttagtatg tatttgtatt tgtaaaatac ttctatcaat aaaatttcta attcctaaaa   9060
ccaaaatcca gtgaccgggt ggtcagtccc ttatgttacg tcctgtagaa accccaaccc   9120
gtgaaatcaa aaaactcgac ggcctgtggg cattcagtct ggatcgcgaa aactgtggaa   9180
ttgatcagcg ttggtgggaa agcgcgttac aagaaagccg ggcaattgct gtgccaggca   9240
gttttaacga tcagttcgcc gatgcagata ttcgtaatta tgcgggcaac gtctggtatc   9300
agcgcgaagt ctttataccg aaaggttggg caggccagcg tatcgtgctg cgtttcgatg   9360
cggtcactca ttacggcaaa gtgtgggtca ataatcagga agtgatggag catcagggcg   9420
gctatacgcc atttgaagcc gatgtcacgc cgtatgttat tgccgggaaa agtgtacaat   9480
tcactggccg tcgttttaca acgtcgtgac tgggaaaacc ctggcgttac ccaacttaat   9540
cgccttgcag cacatccccc tttcgccagc tggcgtaata gcgaagaggc ccgcaccgat   9600
cgcccttccc aacagttgcg cagcctgaat ggcgaatgnn nnnnnaattc agtacattaa   9660
aaacgtccgc aatgtgttat taagttgtct aagcgtcaat ttgtttacac cacaatatat   9720
cctgccacca gccagccaac agctccccga ccggcagctc ggcacaaaat caccactcga   9780
tacaggcagc ccatcagnnn nnnnnnnnnn nnnnnnnnnn nnnnnnnnnn nnnnnnnnnn   9840
```

nnnnnnnnnn nnnnnnnnnn nnnnnnnnnn nnnnnnnnnn nnnnnnnnnn nnnnnnnnnn 9900
nnnnnnnnnn nnnnnnnnnn nnnnnnnnnn nnnnnnnnnn nnnnnnnnnn nnnnnnnnnn 9960
nnnnnnnnnn nnnnnnnnnn nnnnnnnnnn nnnnnnnnnn nnnnnnnnnn nnnnnnnnnn 10020
nnnnnnnnnn nnnnnnnnnn nnnnnnnnnn nnnnnnnnnn nnnnnnnnnn nnnnnnnnnn 10080
nnnnnnnnnn nnnnnnnnnn 10100

<210> SEQ ID NO 6
<211> LENGTH: 10240
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (9639)..(9645)
<223> OTHER INFORMATION: 7 nucleotides which are unknown.
<220> FEATURE:
<221> NAME/KEY: unsure
<222> LOCATION: (9798)..(10240)
<223> OTHER INFORMATION: 443 nucleotides which are unknown.

<400> SEQUENCE: 6
aaacactgat agtttaaact gaaggcggga aacgacaatc tgatcatgag cggagaatta 60
agggagtcac gttatgaccc ccgccgatga cgcgggacaa gccgttttac gtttggaact 120
gacagaaccg caacgattga aggagccact cagccgcggg tttctggagt ttaatgagct 180
aagcacatac gtcagaaacc attattgcgc gttcaaaagt cgcctaaggt cactatcagc 240
tagcaaatat ttcttgtcaa aaatgctcca ctgacgttcc ataaattccc ctcggtatcc 300
aattagnnnn nnnnnnnnnn nnnnnnnnnn gatcgtttcg catgattgaa caagatggat 360
tgcacgcagg ttctccggcc gcttgggtgg agaggctatt cggctatgac tgggcacaac 420
agacaatcgg ctgctctgat gccgccgtgt tccggctgtc agcgcagggg cgcccggttc 480
tttttgtcaa gaccgacctg tccggtgccc tgaatgaact gcaggacgag gcagcgcggc 540
tatcgtggct ggccacgacg ggcgttcctt gcgcagctgt gctcgacgtt gtcactgaag 600
cgggaaggga ctggctgcta ttgggcgaag tgccggggca ggatctcctg tcatctcacc 660
ttgctcctgc cgagaaagta tccatcatgg ctgatgcaat gcggcggctg catacgcttg 720
atccggctac ctgcccattc gaccaccaag cgaaacatcg catcgagcga gcacgtactc 780
ggatggaagc cggtcttgtc gatcaggatg atctggacga agagcatcag gggctcgcgc 840
cagccgaact gttcgccagg ctcaaggcgc gcatgcccga cggcgatgat ctcgtcgtga 900
cccatggcga tgcctgcttg ccgaatatca tggtggaaaa tggccgcttt tctggattca 960
tcgactgtgg ccggctgggt gtggcggacc gctatcagga catagcgttg gctacccgtg 1020
atattgctga agagcttggc ggcgaatggg ctgaccgctt cctcgtgctt tacggtatcg 1080
ccgctcccga ttcgcagcgc atcgccttct atcgccttct tgacgagttc ttctgannnn 1140
nnnnnnnnnn nnnnnnnnnn gatcgttcaa acatttggca ataaagtttc ttaagattga 1200
atcctgttgc cggtcttgcg atgattatca tataatttct gttgaattac gttaagcatg 1260
taataattaa catgtaatgc atgacgttat ttatgagatg ggtttttatg attagagtcc 1320

-continued

```
cgcaattata catttaatac gcgatagaaa acaaaatata gcgcgcaaac taggataaat   1380

tatcgcgcgc ggtgtcatct atgttactag atcgggcctc ctgtcaatgc tggcggcggc   1440

tctggtggtg gttctggtgg cggctctgag ggtggtggct ctgagggtgg cggttctgag   1500

ggtggcggct ctgagggagg cggttccggt ggtggctctg gttccggtga ttttgattat   1560

gaaaagatgg caaacgctaa taagggggct atgaccgaaa atgccgatga aaacgcgcta   1620

cagtctgacg ctaaaggcaa acttgattct gtcgctactg attacggtgc tgctatcgat   1680

ggtttcattg gtgacgtttc cggccttgct aatggtaatg gtgctactgg tgattttgct   1740

ggctctaatt cccaaatggc tcaagtcggt gacggtgata attcaccttt aatgaataat   1800

ttccgtcaat atttaccttc cctccctcaa tcggttgaat gtcgcccttt tgtctttggc   1860

ccaatacgca aaccgcctct ccccgcgcgt tggccgattc attaatgcag ctggcacgac   1920

aggtttcccg actggaaagc gggcagtgag cgcaacgcaa ttaatgtgag ttagctcact   1980

cattaggcac cccaggcttt acactttatg cttccggctc gtatgttgtg tggaattgtg   2040

agcggataac aatttcacac aggaaacagc tatgaccatg attacgccaa gcttgcatgc   2100

ctgcaggtca ctggattttg gttttaggaa ttagaaattt tattgataga agtattttac   2160

aaatacaaat acatactaag ggtttcttat atgctcaaca catgagcgaa accctataag   2220

aaccctaatt cccttatctg ggaactactc acacattatt ctggagaaaa tagagagaga   2280

tagatttgta gagagagact ggtgatttgc ggactctaga ggatccccag cttttaaact   2340

tagccaaagt ggtctgcctg accaggagtt tttaacctta accaaagggc tgttcacagc   2400

ttaggttcat atatcataga accgatcatc tcagatcaga gggcttaaaa gtctcacaat   2460

gggacttcac gagcaaagca tcaactgacg ttaggcctcc tctaccggta gcgtaatcgt   2520

cgaccttctt tttcaagcgt tgtgtggtcc tacgatcatt agctaatttg agtgactcac   2580

gctcaagggc ctcatgtaaa cgtccgatcc gtttgacagg gagctcctta gtactacagt   2640

ccgaggaata aattccaatg gttctgtaga ctttgtctaa cacaccagga aactttggat   2700

tcttccagtt gtgaaaccag tcaccatcag ttttacgctc ttccgtggtg cgtttgaact   2760

tacatacagg atcgctcatc tgataaactc tgatgccttc ggtacagtag caatcagaga   2820

acctcaggaa attctcggag tataaagaaa aagccgcaag agcagctcta acctcctcga   2880

aaatccaagg tttttctttc ccatatttca gataaacaaa atgacagagc gtcgtaatca   2940

tcttctcatc aagttgatta ataaacttca ttcgatcaca gaaggaaacg aaatgtgctc   3000

tgagcatctg ttcatcacgc agaatctttc gcttagctaa gcgctggatc tctctcagag   3060

gatctggtac agacaccaaa ttgcccattt cagtttcgac gagaaactta ctacaaacgt   3120

agggcacact agggtccatg acttttatct ccatattgaa gagagacgta aacatatcgg   3180

tatccaggac tggcttaact ttagagatga ttaaagaatc atctcctgaa aatattgcac   3240

agtcacagtc acttagatca gaggcatatg caatcatagc catagtgaca agagtattac   3300

cgaaatatgt aaacgcgtca ccagttctgc gttggaagga aacggacatt cccaccttgg   3360

catgagggtc tgataaataa gaatcgcgat gaaaatcaga ccaccaattc gtcagcggcg   3420

ctggaaagcc cagcgcaagg agtatctctc tctgaaactc taggtgcagc tcaccctgag   3480

atttatcaaa tttgcttagg tccgcttcaa gaaagtatct gttattcaag cggacattct   3540

taagctccag agaggatatc tttccgatag gcacaatgaa cctggatttc agggccagtg   3600

ataacttctc gaaacaagca gtgaaaaagg gtgaaaaatt actagtcaca cctttactat   3660

gaaatgttat agtagctgct actgctcgtt ccaagtgaag ggtgtcagtt acaacaggtt   3720
```

-continued

```
ttacgtcaga cttcagcata tgctggtacc gacataaatc agtctctgct gccacattca   3780

caccttgcaa gtccatgtgc ttaccccact tcttatggta ctcaagacat ttagtcatga   3840

catccataga agctctcaga cagtcttcac cgtcaacatt aaggaatgtg ctacgaaagc   3900

gctttgctat agctttcgca gtgtccttca tgttaatcgc gtctcccatt tctggaacgt   3960

ccgcgtttcg ctttttgagt gcggttaaga cttctttctg agtaccaact cttcgctgag   4020

cactcccgat attcattttt ggttgaaaat atttatcggg gtccctatac cagtctacat   4080

cactttgctt aagtctgatc ctatcaaagt ccatggaata atcaccattt tcaacaaggg   4140

cttgatggta cgaatcatcg aaataagcat gggttggcag tatggaatga ctggtcgctt   4200

ctgttctagc aaggctgact ctctccatat aaattggccc agtagagatg tcagggttat   4260

ctggatggca gtgtgtatca ataacacgcg aaaccctatg ttcaataggg ttcatgattt   4320

gaagagtgat gtcgtaatca gtattagtag tctgaaactc ttcatcaatg cccatgtacc   4380

tatctccaag ggtcagctcc ttgggggtat ctccagtaac acgaacttcc tcaatttcac   4440

agttcgagga atcactggcg agttttagat cgctcgcatg atcttcatcg gcggcaaacg   4500

atacaccgta accatcacta gtatcctcgg gataccagtc atcaatttca tcttcgagca   4560

cgaaagagcc cggaatgtca agatataaca tccgtgccat ttcagcttga ggaatcagcg   4620

gtctatcggt gaactgttga accatttgtt ggacggtgtc gcaaatagag ccccagcgca   4680

ctcggtcaaa agggggatcg aatacccctc ctatctccaa gggcgctata gctaatttaa   4740

aactcgcgag agatccgtca atggcaactc cgtctgccgg ctcctgcacc tgaaggctag   4800

cagcctccac ctcgtcttct aaggattgat ctatgatcca ttggaaagac gggacctggc   4860

gaacgaaatc atcatcccag gttttcgaag acatcttggt gatagtagaa agaacaagca   4920

cacaacaaca acaaggtcag atgtgtgttg cgggtaccga gctcgaattc tcgaggtcct   4980

ctccaaatga aatgaacttc cttatataga ggaagggtct tgcgaaggat agtgggattg   5040

tgcgtcatcc cttacgtcag tggagatatc acatcaatcc acttgctttg aagacgtggt   5100

tggaacgtct tctttttcca cgatgttcct cgtgggtggg ggtccatctt tgggaccact   5160

gtcggtagag gcattcttga acgatagcct ttcctttatc gcaatgatgg catttgtaga   5220

agccatcttc cttttctact gtcctttcga tgaagtgaca gatagctggg caatggaatc   5280

cgaggaggtt tcccgatatt accctttgtt gaaaagtctc aatagccctc tggtcttctg   5340

agactgtatc tttgatattc ttggagtaga cgagagtgtc gtgctccacc atgttgacct   5400

gcaggcagca agcttgcatg cctgcaggtc gactctagag gatccccggt cactggattt   5460

tggttttagg aattagaaat tttattgata gaagtatttt acaaatacaa atacatacta   5520

agggtttctt atatgctcaa cacatgagcg aaaccctata agaaccctaa ttcccttatc   5580

tgggaactac tcacacatta ttctggagaa aatagagaga gatagatttg tagagagaga   5640

ctggtgattt gcggactcta gaggatcccc gggtaccgag ctcgaattct cgagcagagg   5700

tctcacacag agacaagcgc atcacttaac acaattaaag atcaaatcac cagcgagctc   5760

gccgttaaag caatactcaa aggacttctt gtgtcgtgtt aaggcaacca aacagtactc   5820

ctcatgttta aacaaatcac atttggtcga cttaagccga accaaagtga cgttgtcaac   5880

agagatccct tgcgcttcgt gtactgtttt tatgtgtcca tcaatccagt ccttgctcac   5940

gggaaaatcc ttagccctcg tttgaagggc cgctttatca gcttgagtca tcgtaagata   6000

cgttctgttc ggatcaatag tgacctgcaa accagaagta atacgacgct tcgtgagact   6060
```

-continued

```
tctagaaact ttggactcag atgtccagga ttgatacttc gtgtccctat taccgcattt   6120
acgcttcagc agattaacag cagcgataac atcttgcgga caccggtaag tcttgtgaac   6180
aacgtcacgg cgatcatatt gcagattacc gtggagcaat ttaaaacccg cgtcacgaga   6240
cttgaacgaa atctgctctg tgtccccaaa ggcaagaact tgtgaacatt tagacagagc   6300
agccaccacc aggagttgac cataatgtag taaaccagcc tcatcaacaa gcagcctatg   6360
acaggacggt acaccgtgca tgatcgcaga atccgcggtg cgcacaacgt ccaaagctac   6420
cttggaatta taagtgtcag ggaataaagc catcctgacg tcctcggccg atttacgatt   6480
cgccgtcaca attaggtcct ctcccatacg gaatgcatct tttatggcag tggttttacc   6540
gcatcccgca actccatcaa ccatggaaat atcgcatgta gggacagaaa ctttggcgct   6600
agcttctgca atgtccctca agttagagca tgcacatgtt ttatcaacaa tgtacgtttc   6660
atctgcgtgc ttcggaccta aaccatgctc attatatcca acagtgtaat cgtatttttt   6720
aggatacaac cagttaccgt tggccaaatg gacattcacc atatcgtcta tgcgatggta   6780
ggtctcaaag atgctcttat ttgcgatctc acttccgcga ccgccggaaa tgtcccatag   6840
gtgacgaaga ttagactcgg agttgttatg taatctctta caataacgca caaattcctt   6900
catggctccg tgtctagata tgccacgagg gtccgttggt acctcaacag acacctcggc   6960
atccgggacc acatcagtca ccggtttaac gtcatcactg acggactcag ggctcgaact   7020
ctcaggggca tcatgaaact cctcctgagg tatctcagca gctggcggga ctttcgcctt   7080
cttcttcgag cgcttggtct tggctgtctg cacttcatgc tccagccggt cgaataagtc   7140
ctcttcagtc caaaacgttc tcaaacgtga tatcggtaca gaatcttgct caaattcttc   7200
aacgtttgag agacgagtca gaaacttaaa actgtccgca taagaatcca gacgtagtag   7260
gggaaatctg ctagccaatg ttctcagcca tcctactttc gccctggatg aatctccacc   7320
ccaccaaaac ctagttttga agtgatggca ccaacctttc cattccatcc catcgcggag   7380
ggccgtaagc ttttcgtact tttgatacag attcaaagtc aaagcaaagg ccactagatg   7440
ataatcttca atgtctaagc gctcaccagc catgatagcc tgaccgttaa taataacagt   7500
cgacgacttg gcggataaga tagatgcgac agctttcatg ttctcagtcc attctttact   7560
ttccttgaaa catctgaaag ctatctcctc tacctctctc actgtggttt tggcgacgcg   7620
cacacatttc cagcgattga gactccagtc ttcaggtatt gagaccccta cgtacttaga   7680
tatgtcttca aaccatacac agtgacgtag tgtctcccgg gggcagcgta aatttgtagc   7740
gatgatctta taggtcatga tgttacattt cagcatttcg cgctccaaca gataggtggt   7800
tccatcgatg caatgcaccg actcggtgaa aaatgagccc aaatcttgcc atccgtggat   7860
gtaagataat gtgctttcat tttcaaaatc gaatttgatc acctcatccg cgcctgaccc   7920
gtcacgttgc cagtgacatt taagcaaggg aagaaaaccc tcgcggtcaa acaacatggc   7980
gccgtcgaac ataacggtac cacgtagtac gcgtactcca tgcgaatgca tggcgtcaca   8040
cagaccttgg aagcccatat cataaccgcc gtggatacag atagcccaat cagcttggac   8100
atcacaatct tgagctcggt taagacaaaa gttcgggact tcatcgaaat catcgctttc   8160
ttgcaaaatt tttcgcatgc ggcacatcct ctcctcatgt cgggcagcgt ctctaacacc   8220
caacacagga caacaactgt gcaccctttt atcccttctt gaaaagtgat gccaccaaga   8280
ccctccgaaa tctataacgg ggtcttcagg gggaaaactg tcgagacagt cataatgctc   8340
cgctacacgc agagcaccag ccaggctatg gggcgcatga tactgctgag tcaaatttaa   8400
gtcaaaggca ccaccataac ggtcacggaa ggcgtcagcc tcctcaatag agagcttatt   8460
```

```
gcgaacgttg attttcttag accttttcgc gtattcaatc tgcgcagata actgttgcgc   8520
aacctgattg tctacgatgt cttgggcact ctggctgtca gcacccttct cagcaatcaa   8580
cttcagcaaa tcgatagaac ttgacatttt gttggtgaaa aacaaagaac aagtagcaga   8640
accgtggtcg aggtcctctc caaatgaaat gaacttcctt atatagagga agggtcttgc   8700
gaaggatagt gggattgtgc gtcatccctt acgtcagtgg agatatcaca tcaatccact   8760
tgctttgaag acgtggttgg aacgtcttct ttttccacga tgttcctcgt gggtgggggt   8820
ccatctttgg gaccactgtc ggtagaggca ttcttgaacg atagcctttc ctttatcgca   8880
atgatggcat ttgtagaagc catcttcctt ttctactgtc ctttcgatga agtgacagat   8940
agctgggcaa tggaatccga ggaggtttcc cgatattacc ctttgttgaa aagtctcaat   9000
agccctctgg tcttctgaga ctgtatcttt gatattcttg gagtagacga gagtgtcgtg   9060
ctccaccatg ttgaccgggt ggtcagtccc ttatgttacg tcctgtagaa accccaaccc   9120
gtgaaatcaa aaaactcgac ggcctgtggg cattcagtct ggatcgcgaa aactgtggaa   9180
ttgatcagcg ttggtgggaa agcgcgttac aagaaagccg ggcaattgct gtgccaggca   9240
gttttaacga tcagttcgcc gatgcagata ttcgtaatta tgcgggcaac gtctggtatc   9300
agcgcgaagt ctttataccg aaaggttggg caggccagcg tatcgtgctg cgtttcgatg   9360
cggtcactca ttacggcaaa gtgtgggtca ataatcagga agtgatggag catcagggcg   9420
gctatacgcc atttgaagcc gatgtcacgc cgtatgttat tgccgggaaa agtgtacaat   9480
tcactggccg tcgttttaca acgtcgtgac tgggaaaacc ctggcgttac ccaacttaat   9540
cgccttgcag cacatccccc tttcgccagc tggcgtaata gcgaagaggc ccgcaccgat   9600
cgcccttccc aacagttgcg cagcctgaat ggcgaatgnn nnnnnaattc agtacattaa   9660
aaacgtccgc aatgtgttat taagttgtct aagcgtcaat ttgtttacac cacaatatat   9720
cctgccacca gccagccaac agctccccga ccggcagctc ggcacaaaat caccactcga   9780
tacaggcagc ccatcagnnn nnnnnnnnnn nnnnnnnnnn nnnnnnnnnn nnnnnnnnnn   9840
nnnnnnnnnn nnnnnnnnnn nnnnnnnnnn nnnnnnnnnn nnnnnnnnnn nnnnnnnnnn   9900
nnnnnnnnnn nnnnnnnnnn nnnnnnnnnn nnnnnnnnnn nnnnnnnnnn nnnnnnnnnn   9960
nnnnnnnnnn nnnnnnnnnn nnnnnnnnnn nnnnnnnnnn nnnnnnnnnn nnnnnnnnnn  10020
nnnnnnnnnn nnnnnnnnnn nnnnnnnnnn nnnnnnnnnn nnnnnnnnnn nnnnnnnnnn  10080
nnnnnnnnnn nnnnnnnnnn nnnnnnnnnn nnnnnnnnnn nnnnnnnnnn nnnnnnnnnn  10140
nnnnnnnnnn nnnnnnnnnn nnnnnnnnnn nnnnnnnnnn nnnnnnnnnn nnnnnnnnnn  10200
nnnnnnnnnn nnnnnnnnnn nnnnnnnnnn nnnnnnnnnn                        10240
```

<210> SEQ ID NO 7
<211> LENGTH: 10272
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (9639)..(9645)
<223> OTHER INFORMATION: 7 nucleotides which are unknown.
<220> FEATURE:

-continued

<221> NAME/KEY: unsure
<222> LOCATION: (9798)..(10272)
<223> OTHER INFORMATION: 475 nucleotides which are unknown.

<400> SEQUENCE: 7
aaacactgat agtttaaact gaaggcggga aacgacaatc tgatcatgag cggagaatta 60
agggagtcac gttatgaccc ccgccgatga cgcgggacaa gccgttttac gtttggaact 120
gacagaaccg caacgattga aggagccact cagccgcggg tttctggagt ttaatgagct 180
aagcacatac gtcagaaacc attattgcgc gttcaaaagt cgcctaaggt cactatcagc 240
tagcaaatat ttcttgtcaa aaatgctcca ctgacgttcc ataaattccc ctcggtatcc 300
aattagnnnn nnnnnnnnnn nnnnnnnnnn gatcgtttcg catgattgaa caagatggat 360
tgcacgcagg ttctccggcc gcttgggtgg agaggctatt cggctatgac tgggcacaac 420
agacaatcgg ctgctctgat gccgccgtgt tccggctgtc agcgcagggg cgcccggttc 480
tttttgtcaa gaccgacctg tccggtgccc tgaatgaact gcaggacgag gcagcgcggc 540
tatcgtggct ggccacgacg ggcgttcctt gcgcagctgt gctcgacgtt gtcactgaag 600
cgggaaggga ctggctgcta ttgggcgaag tgccggggca ggatctcctg tcatctcacc 660
ttgctcctgc cgagaaagta tccatcatgg ctgatgcaat gcggcggctg catacgcttg 720
atccggctac ctgcccattc gaccaccaag cgaaacatcg catcgagcga gcacgtactc 780
ggatggaagc cggtcttgtc gatcaggatg atctggacga agagcatcag gggctcgcgc 840
cagccgaact gttcgccagg ctcaaggcgc gcatgcccga cggcgatgat ctcgtcgtga 900
cccatggcga tgcctgcttg ccgaatatca tggtggaaaa tggccgcttt tctggattca 960
tcgactgtgg ccggctgggt gtggcggacc gctatcagga catagcgttg gctacccgtg 1020
atattgctga agagcttggc ggcgaatggg ctgaccgctt cctcgtgctt tacggtatcg 1080
ccgctcccga ttcgcagcgc atcgccttct atcgccttct tgacgagttc ttctgannnn 1140
nnnnnnnnnn nnnnnnnnnn gatcgttcaa acatttggca ataaagtttc ttaagattga 1200
atcctgttgc cggtcttgcg atgattatca tataatttct gttgaattac gttaagcatg 1260
taataattaa catgtaatgc atgacgttat ttatgagatg ggtttttatg attagagtcc 1320
cgcaattata catttaatac gcgatagaaa acaaaatata gcgcgcaaac taggataaat 1380
tatcgcgcgc ggtgtcatct atgttactag atcgggcctc ctgtcaatgc tggcggcggc 1440
tctggtggtg gttctggtgg cggctctgag ggtggtggct ctgagggtgg cggttctgag 1500
ggtggcggct ctgagggagg cggttccggt ggtggctctg gttccggtga ttttgattat 1560
gaaaagatgg caaacgctaa taagggggct atgaccgaaa atgccgatga aaacgcgcta 1620
cagtctgacg ctaaaggcaa acttgattct gtcgctactg attacggtgc tgctatcgat 1680
ggtttcattg gtgacgtttc cggccttgct aatggtaatg gtgctactgg tgattttgct 1740
ggctctaatt cccaaatggc tcaagtcggt gacggtgata attcaccttt aatgaataat 1800
ttccgtcaat atttaccttc cctccctcaa tcggttgaat gtcgcccttt tgtctttggc 1860
ccaatacgca aaccgcctct ccccgcgcgt tggccgattc attaatgcag ctggcacgac 1920
aggtttcccg actggaaagc gggcagtgag cgcaacgcaa ttaatgtgag ttagctcact 1980
cattaggcac cccaggcttt acactttatg cttccggctc gtatgttgtg tggaattgtg 2040
agcggataac aatttcacac aggaaacagc tatgaccatg attacgccaa gcttgctgcc 2100
tgcaggtcaa catggtggag cacgacactc tcgtctactc caagaatatc aaagatacag 2160
tctcagaaga ccagagggct attgagactt ttcaacaaag ggtaatatcg ggaaacctcc 2220

-continued

```
tcggattcca ttgcccagct atctgtcact tcatcgaaag gacagtagaa aaggaagatg   2280
gcttctacaa atgccatcat tgcgataaag gaaaggctat cgttcaagaa tgcctctacc   2340
gacagtggtc ccaaagatgg acccccaccc acgaggaaca tcgtggaaaa agaagacgtt   2400
ccaaccacgt cttcaaagca agtggattga tgtgatatct ccactgacgt aagggatgac   2460
gcacaatccc actatccttc gcaagaccct tcctctatat aaggaagttc atttcatttg   2520
gagaggacct cgagaattcg agctcggtac ccgcaacaca catctgacct tgttgttgtt   2580
gtgtgcttgt tctttctact atcaccaaga tgtcttcgaa aacctgggat gatgatttcg   2640
ttcgccaggt cccgtctttc caatggatca tagatcaatc cttagaagac gaggtggagg   2700
ctgctagcct tcaggtgcag gagccggcag acggagttgc cattgacgga tctctcgcga   2760
gttttaaatt agctatagcg cccttggaga taggaggggt attcgatccc ccttttgacc   2820
gagtgcgctg gggctctatt tgcgacaccg tccaacaaat ggttcaacag ttcaccgata   2880
gaccgctgat tcctcaagct gaaatggcac ggatgttata tcttgacatt ccgggctctt   2940
tcgtgctcga agatgaaatt gatgactggt atcccgagga tactagtgat ggttacggtg   3000
tatcgtttgc cgccgatgaa gatcatgcga gcgatctaaa actcgccagt gattcctcga   3060
actgtgaaat tgaggaagtt cgtgttactg gagatacccc caaggagctg acccttggag   3120
ataggtacat gggcattgat gaagagtttc agactactaa tactgattac gacatcactc   3180
ttcaaatcat gaaccctatt gaacataggg tttcgcgtgt tattgataca cactgccatc   3240
cagataaccc tgacatctct actgggccaa tttatatgga gagagtcagc cttgctagaa   3300
cagaagcgac cagtcattcc atactgccaa cccatgctta tttcgatgat tcgtaccatc   3360
aagcccttgt tgaaaatggt gattattcca tggactttga taggatcaga cttaagcaaa   3420
gtgatgtaga ctggtatagg gaccccgata aatattttca accaaaaatg aatatcggga   3480
gtgctcagcg aagagttggt actcagaaag aagtcttaac cgcactcaaa aagcgaaacg   3540
cggacgttcc agaaatggga gacgcgatta acatgaagga cactgcgaaa gctatagcaa   3600
agcgctttcg tagcacattc cttaatgttg acggtgaaga ctgtctgaga gcttctatgg   3660
atgtcatgac taaatgtctt gagtaccata agaagtgggg taagcacatg gacttgcaag   3720
gtgtgaatgt ggcagcagag actgatttat gtcggtacca gcatatgctg aagtctgacg   3780
taaaacctgt tgtaactgac acccttcact tggaacgagc agtagcagct actataacat   3840
ttcatagtaa aggtgtgact agtaattttt caccctttttt cactgcttgt ttcgagaagt   3900
tatcactggc cctgaaatcc aggttcattg tgcctatcgg aaagatatcc tctctggagc   3960
ttaagaatgt ccgcttgaat aacagatact ttcttgaagc ggacctaagc aaatttgata   4020
aatctcaggg tgagctgcac ctagagtttc agagagagat actccttgcg ctgggctttc   4080
cagcgccgct gacgaattgg tggtctgatt ttcatcgcga ttcttattta tcagaccctc   4140
atgccaaggt gggaatgtcc gtttccttcc aacgcagaac tggtgacgcg tttacatatt   4200
tcggtaatac tcttgtcact atggctatga ttgcatatgc ctctgatcta agtgactgtg   4260
actgtgcaat attttcagga gatgattctt taatcatctc taaagttaag ccagtcctgg   4320
ataccgatat gtttacgtct ctcttcaata tggagataaa agtcatggac cctagtgtgc   4380
cctacgtttg tagtaagttt ctcgtcgaaa ctgaaatggg caatttggtg tctgtaccag   4440
atcctctgag agagatccag cgcttagcta agcgaaagat tctgcgtgat gaacagatgc   4500
tcagagcaca tttcgtttcc ttctgtgatc gaatgaagtt tattaatcaa cttgatgaga   4560
```

-continued agatgattac gacgctctgt cattttgttt atctgaaata tgggaaagaa aaaccttgga 4620
ttttcgagga ggttagagct gctcttgcgg ctttttcttt atactccgag aatttcctga 4680
ggttctctga ttgctactgt accgaaggca tcagagttta tcagatgagc gatcctgtat 4740
gtaagttcaa acgcaccacg gaagagcgta aaactgatgg tgactggttt cacaactgga 4800
agaatccaaa gtttcctggt gtgttagaca aagtctacag aaccattgga atttattcct 4860
cggactgtag tactaaggag ctccctgtca aacggatcgg acgtttacat gaggcccttg 4920
agcgtgagtc actcaaatta gctaatgatc gtaggaccac acaacgcttg aaaaagaagg 4980
tcgacgatta cgctaccggt agaggaggcc taacgtcagt tgatgctttg ctcgtgaagt 5040
cccattgtga gacttttaag ccctctgatc tgagatgatc ggttctatga tatatgaacc 5100
taagctgtga acagcccttt ggttaaggtt aaaaactcct ggtcaggcag accactttgg 5160
ctaagtttaa aagctgggga tcctctagag tccgcaaatc accagtctct ctctacaaat 5220
ctatctctct ctattttctc cagaataatg tgtgagtagt tcccagataa gggaattagg 5280
gttcttatag ggtttcgctc atgtgttgag catataagaa acccttagta tgtatttgta 5340
tttgtaaaat acttctatca ataaaatttc taattcctaa aaccaaaatc cagtgacctg 5400
caggcatgca agcttgcatg cctgcaggtc gactctagag gatccccggt caacatggtg 5460
gagcacgaca ctctcgtcta ctccaagaat atcaaagata cagtctcaga agaccagagg 5520
gctattgaga cttttcaaca aagggtaata tcgggaaacc tcctcggatt ccattgccca 5580
gctatctgtc acttcatcga aaggacagta gaaaaggaag atggcttcta caaatgccat 5640
cattgcgata aaggaaaggc tatcgttcaa gaatgcctct accgacagtg gtcccaaaga 5700
tggaccccca cccacgagga acatcgtgga aaaagaagac gttccaacca cgtcttcaaa 5760
gcaagtggat tgatgtgata tctccactga cgtaagggat gacgcacaat cccactatcc 5820
ttcgcaagac ccttcctcta tataaggaag ttcatttcat ttggagagga cctcgaccac 5880
ggttctgcta cttgttcttt gtttttcacc aacaaaatgt caagttctat cgatttgctg 5940
aagttgattg ctgagaaggg tgctgacagc cagagtgccc aagacatcgt agacaatcag 6000
gttgcgcaac agttatctgc gcagattgaa tacgcgaaaa ggtctaagaa aatcaacgtt 6060
cgcaataagc tctctattga ggaggctgac gccttccgtg accgttatgg tggtgccttt 6120
gacttaaatt tgactcagca gtatcatgcg ccccatagcc tggctggtgc tctgcgtgta 6180
gcggagcatt atgactgtct cgacagtttt ccccctgaag accccgttat agatttcgga 6240
gggtcttggt ggcatcactt ttcaagaagg gataaaaggg tgcacagttg ttgtcctgtg 6300
ttgggtgtta gagacgctgc ccgacatgag gagaggatgt gccgcatgcg aaaaattttg 6360
caagaaagcg atgatttcga tgaagtcccg aacttttgtc ttaaccgagc tcaagattgt 6420
gatgtccaag ctgattgggc tatctgtatc cacggcggtt atgatatggg cttccaaggt 6480
ctgtgtgacg ccatgcattc gcatggagta cgcgtactac gtggtaccgt tatgttcgac 6540
ggcgccatgt tgtttgaccg cgagggtttt cttcccttgc ttaaatgtca ctggcaacgt 6600
gacgggtcag gcgcggatga ggtgatcaaa ttcgattttg aaaatgaaag cacattatct 6660
tacatccacg gatggcaaga tttgggctca tttttcaccg agtcggtgca ttgcatcgat 6720
ggaaccacct atctgttgga gcgcgaaatg ctgaaatgta acatcatgac ctataagatc 6780
atcgctacaa atttacgctg cccccgggag acactacgtc actgtgtatg gtttgaagac 6840
atatctaagt acgtaggggt ctcaatacct gaagactgga gtctcaatcg ctggaaatgt 6900
gtgcgcgtcg ccaaaaccac agtgagagag gtagaggaga tagctttcag atgtttcaag 6960
gaaagtaaag aatggactga gaacatgaaa gctgtcgcat ctatcttatc cgccaagtcg 7020
tcgactgtta ttattaacgg tcaggctatc atggctggtg agcgcttaga cattgaagat 7080
tatcatctag tggcctttgc tttgactttg aatctgtatc aaaagtacga aaagcttacg 7140
gccctccgcg atgggatgga atggaaaggt tggtgccatc acttcaaaac taggttttgg 7200
tggggtggag attcatccag ggcgaaagta ggatggctga gaacattggc tagcagattt 7260
cccctactac gtctggattc ttatgcggac agttttaagt ttctgactcg tctctcaaac 7320
gttgaagaat ttgagcaaga ttctgtaccg atatcacgtt tgagaacgtt ttggactgaa 7380
gaggacttat tcgaccggct ggagcatgaa gtgcagacag ccaagaccaa gcgctcgaag 7440
aagaaggcga aagtcccgcc agctgctgag atacctcagg aggagtttca tgatgcccct 7500
gagagttcga gccctgagtc cgtcagtgat gacgttaaac cggtgactga tgtggtcccg 7560
gatgccgagg tgtctgttga ggtaccaacg gaccctcgtg gcatatctag acacggagcc 7620
atgaaggaat ttgtgcgtta ttgtaagaga ttacataaca actccgagtc taatcttcgt 7680
cacctatggg acatttccgg cggtcgcgga agtgagatcg caaataagag catctttgag 7740
acctaccatc gcatagacga tatggtgaat gtccatttgg ccaacggtaa ctggttgtat 7800
cctaaaaaat acgattacac tgttggatat aatgagcatg gtttaggtcc gaagcacgca 7860
gatgaaacgt acattgttga taaaacatgt gcatgctcta acttgaggga cattgcagaa 7920
gctagcgcca aagtttctgt ccctacatgc gatatttcca tggttgatgg agttgcggga 7980
tgcggtaaaa ccactgccat aaaagatgca ttccgtatgg gagaggacct aattgtgacg 8040
gcgaatcgta aatcggccga ggacgtcagg atggctttat tccctgacac ttataattcc 8100
aaggtagctt tggacgttgt gcgcaccgcg gattctgcga tcatgcacgg tgtaccgtcc 8160
tgtcataggc tgcttgttga tgaggctggt ttactacatt atggtcaact cctggtggtg 8220
gctgctctgt ctaaatgttc acaagttctt gcctttgggg acacagagca gatttcgttc 8280
aagtctcgtg acgcgggttt taaattgctc cacggtaatc tgcaatatga tcgccgtgac 8340
gttgttcaca agacttaccg gtgtccgcaa gatgttatcg ctgctgttaa tctgctgaag 8400
cgtaaatgcg gtaataggga cacgaagtat caatcctgga catctgagtc caaagtttct 8460
agaagtctca cgaagcgtcg tattacttct ggtttgcagg tcactattga tccgaacaga 8520
acgtatctta cgatgactca agctgataaa gcggcccttc aaacgagggc taaggatttt 8580
cccgtgagca aggactggat tgatggacac ataaaaacag tacacgaagc gcaagggatc 8640
tctgttgaca acgtcacttt ggttcggctt aagtcgacca aatgtgattt gtttaaacat 8700
gaggagtact gtttggttgc cttaacacga cacaagaagt cctttgagta ttgctttaac 8760
ggcgagctcg ctggtgattt gatctttaat tgtgttaagt gatgcgcttg tctctgtgtg 8820
agacctctgc tcgagaattc gagctcggta cccggggatc ctctagagtc cgcaaatcac 8880
cagtctctct ctacaaatct atctctctct attttctcca gaataatgtg tgagtagttc 8940
ccagataagg gaattagggt tcttataggg tttcgctcat gtgttgagca tataagaaac 9000
ccttagtatg tatttgtatt tgtaaaatac ttctatcaat aaaatttcta attcctaaaa 9060
ccaaaatcca gtgaccgggt ggtcagtccc ttatgttacg tcctgtagaa accccaaccc 9120
gtgaaatcaa aaaactcgac ggcctgtggg cattcagtct ggatcgcgaa aactgtggaa 9180
ttgatcagcg ttggtgggaa agcgcgttac aagaaagccg ggcaattgct gtgccaggca 9240
gttttaacga tcagttcgcc gatgcagata ttcgtaatta tgcgggcaac gtctggtatc 9300
agcgcgaagt ctttataccg aaaggttggg caggccagcg tatcgtgctg cgtttcgatg 9360
cggtcactca ttacggcaaa gtgtgggtca ataatcagga agtgatggag catcagggcg 9420
gctatacgcc atttgaagcc gatgtcacgc cgtatgttat tgccgggaaa agtgtacaat 9480
tcactggccg tcgttttaca acgtcgtgac tgggaaaacc ctggcgttac ccaacttaat 9540
cgccttgcag cacatccccc tttcgccagc tggcgtaata gcgaagaggc ccgcaccgat 9600
cgcccttccc aacagttgcg cagcctgaat ggcgaatgnn nnnnnaattc agtacattaa 9660
aaacgtccgc aatgtgttat taagttgtct aagcgtcaat ttgtttacac cacaatatat 9720
cctgccacca gccagccaac agctccccga ccggcagctc ggcacaaaat caccactcga 9780
tacaggcagc ccatcagnnn nnnnnnnnnn nnnnnnnnnn nnnnnnnnnn nnnnnnnnnn 9840
nnnnnnnnnn nnnnnnnnnn nnnnnnnnnn nnnnnnnnnn nnnnnnnnnn nnnnnnnnnn 9900
nnnnnnnnnn nnnnnnnnnn nnnnnnnnnn nnnnnnnnnn nnnnnnnnnn nnnnnnnnnn 9960
nnnnnnnnnn nnnnnnnnnn nnnnnnnnnn nnnnnnnnnn nnnnnnnnnn nnnnnnnnnn 10020
nnnnnnnnnn nnnnnnnnnn nnnnnnnnnn nnnnnnnnnn nnnnnnnnnn nnnnnnnnnn 10080
nnnnnnnnnn nnnnnnnnnn nnnnnnnnnn nnnnnnnnnn nnnnnnnnnn nnnnnnnnnn 10140
nnnnnnnnnn nnnnnnnnnn nnnnnnnnnn nnnnnnnnnn nnnnnnnnnn nnnnnnnnnn 10200
nnnnnnnnnn nnnnnnnnnn nnnnnnnnnn nnnnnnnnnn nnnnnnnnnn nnnnnnnnnn 10260
nnnnnnnnnn nn 10272

<210> SEQ ID NO 8
<211> LENGTH: 10166
<212> TYPE: DNA
<213> ORGANISM: Brome mosaic virus
<220> FEATURE:
<221> NAME/KEY: unsure
<222> LOCATION: (307)..(330)
<223> OTHER INFORMATION: 24 nucleotides which are unknown.
<220> FEATURE:
<221> NAME/KEY: unsure
<222> LOCATION: (1137)..(1160)
<223> OTHER INFORMATION: 24 nucleotides which are unknown.
<220> FEATURE:
<221> NAME/KEY: unsure
<222> LOCATION: (9639)..(9645)
<223> OTHER INFORMATION: 7 nucleotides which are unknown.
<220> FEATURE:
<221> NAME/KEY: unsure
<222> LOCATION: (9798)..(10166)
<223> OTHER INFORMATION: 369 nucleotides which are unknown.

<400> SEQUENCE: 8
aaacactgat agtttaaact gaaggcggga aacgacaatc tgatcatgag cggagaatta 60
agggagtcac gttatgaccc ccgccgatga cgcgggacaa gccgttttac gtttggaact 120
gacagaaccg caacgattga aggagccact cagccgcggg tttctggagt ttaatgagct 180
aagcacatac gtcagaaacc attattgcgc gttcaaaagt cgcctaaggt cactatcagc 240
tagcaaatat ttcttgtcaa aaatgctcca ctgacgttcc ataaattccc ctcggtatcc 300
aattagnnnn nnnnnnnnnn nnnnnnnnnn gatcgtttcg catgattgaa caagatggat 360
tgcacgcagg ttctccggcc gcttgggtgg agaggctatt cggctatgac tgggcacaac 420
agacaatcgg ctgctctgat gccgccgtgt tccggctgtc agcgcagggg cgcccggttc 480
tttttgtcaa gaccgacctg tccggtgccc tgaatgaact gcaggacgag gcagcgcggc 540
tatcgtggct ggccacgacg ggcgttcctt gcgcagctgt gctcgacgtt gtcactgaag 600
cgggaaggga ctggctgcta ttgggcgaag tgccggggca ggatctcctg tcatctcacc 660

-continued

```
ttgctcctgc cgagaaagta tccatcatgg ctgatgcaat gcggcggctg catacgcttg    720
atccggctac ctgcccattc gaccaccaag cgaaacatcg catcgagcga gcacgtactc    780
ggatggaagc cggtcttgtc gatcaggatg atctggacga agagcatcag gggctcgcgc    840
cagccgaact gttcgccagg ctcaaggcgc gcatgcccga cggcgatgat ctcgtcgtga    900
cccatggcga tgcctgcttg ccgaatatca tggtggaaaa tggccgcttt tctggattca    960
tcgactgtgg ccggctgggt gtggcggacc gctatcagga catagcgttg gctacccgtg   1020
atattgctga agagcttggc ggcgaatggg ctgaccgctt cctcgtgctt tacggtatcg   1080
ccgctcccga ttcgcagcgc atcgccttct atcgccttct tgacgagttc ttctgannnn   1140
nnnnnnnnnn nnnnnnnnnn gatcgttcaa acatttggca ataaagtttc ttaagattga   1200
atcctgttgc cggtcttgcg atgattatca tataatttct gttgaattac gttaagcatg   1260
taataattaa catgtaatgc atgacgttat ttatgagatg ggtttttatg attagagtcc   1320
cgcaattata catttaatac gcgatagaaa acaaaatata gcgcgcaaac taggataaat   1380
tatcgcgcgc ggtgtcatct atgttactag atcgggcctc ctgtcaatgc tggcggcggc   1440
tctggtggtg gttctggtgg cggctctgag ggtggtggct ctgagggtgg cggttctgag   1500
ggtggcggct ctgagggagg cggttccggt ggtggctctg gttccggtga ttttgattat   1560
gaaaagatgg caaacgctaa taagggggct atgaccgaaa atgccgatga aaacgcgcta   1620
cagtctgacg ctaaaggcaa acttgattct gtcgctactg attacggtgc tgctatcgat   1680
ggtttcattg gtgacgtttc cggccttgct aatggtaatg gtgctactgg tgattttgct   1740
ggctctaatt cccaaatggc tcaagtcggt gacggtgata attcaccttt aatgaataat   1800
ttccgtcaat atttaccttc cctccctcaa tcggttgaat gtcgcccttt tgtctttggc   1860
ccaatacgca aaccgcctct ccccgcgcgt tggccgattc attaatgcag ctggcacgac   1920
aggtttcccg actggaaagc gggcagtgag cgcaacgcaa ttaatgtgag ttagctcact   1980
cattaggcac cccaggcttt acactttatg cttccggctc gtatgttgtg tggaattgtg   2040
agcggataac aatttcacac aggaaacagc tatgaccatg attacgccaa gcttgctgcc   2100
tgcaggtcaa catggtggag cacgacactc tcgtctactc caagaatatc aaagatacag   2160
tctcagaaga ccagagggct attgagactt ttcaacaaag ggtaatatcg ggaaacctcc   2220
tcggattcca ttgcccagct atctgtcact tcatcgaaag gacagtagaa aaggaagatg   2280
gcttctacaa atgccatcat tgcgataaag gaaaggctat cgttcaagaa tgcctctacc   2340
gacagtggtc ccaaagatgg acccccaccc acgaggaaca tcgtggaaaa agaagacgtt   2400
ccaaccacgt cttcaaagca agtggattga tgtgatatct ccactgacgt aagggatgac   2460
gcacaatccc actatccttc gcaagaccct tcctctatat aaggaagttc atttcatttg   2520
gagaggacct cgagaattcg agctcggtac ccgcaacaca catctgacct tgttgttgtt   2580
gtgtgcttgt tctttctact atcaccaaga tgtcttcgaa aacctgggat gatgatttcg   2640
ttcgccaggt cccgtctttc caatggatca tagatcaatc cttagaagac gaggtggagg   2700
ctgctagcct tcaggtgcag gagccggcag acggagttgc cattgacgga tctctcgcga   2760
gttttaaatt agctatagcg cccttggaga taggaggggt attcgatccc ccttttgacc   2820
gagtgcgctg gggctctatt tgcgacaccg tccaacaaat ggttcaacag ttcaccgata   2880
gaccgctgat tcctcaagct gaaatggcac ggatgttata tcttgacatt ccgggctctt   2940
tcgtgctcga agatgaaatt gatgactggt atcccgagga tactagtgat ggttacggtg   3000
```

tatcgtttgc cgccgatgaa gatcatgcga gcgatctaaa actcgccagt gattcctcga 3060
actgtgaaat tgaggaagtt cgtgttactg gagataccccc caaggagctg acccttggag 3120
ataggtacat gggcattgat gaagagtttc agactactaa tactgattac gacatcactc 3180
ttcaaatcat gaaccctatt gaacataggg tttcgcgtgt tattgataca cactgccatc 3240
cagataaccc tgacatctct actgggccaa tttatatgga gagagtcagc cttgctagaa 3300
cagaagcgac cagtcattcc atactgccaa cccatgctta tttcgatgat tcgtaccatc 3360
aagcccttgt tgaaaatggt gattattcca tggactttga taggatcaga cttaagcaaa 3420
gtgatgtaga ctggtatagg gaccccgata aatattttca accaaaaatg aatatcggga 3480
gtgctcagcg aagagttggt actcagaaag aagtcttaac cgcactcaaa aagcgaaacg 3540
cggacgttcc agaaatggga gacgcgatta acatgaagga cactgcgaaa gctatagcaa 3600
agcgctttcg tagcacattc cttaatgttg acggtgaaga ctgtctgaga gcttctatgg 3660
atgtcatgac taaatgtctt gagtaccata agaagtgggg taagcacatg gacttgcaag 3720
gtgtgaatgt ggcagcagag actgatttat gtcggtacca gcatatgctg aagtctgacg 3780
taaaacctgt tgtaactgac acccttcact tggaacgagc agtagcagct actataacat 3840
ttcatagtaa aggtgtgact agtaattttt caccctttt cactgcttgt ttcgagaagt 3900
tatcactggc cctgaaatcc aggttcattg tgcctatcgg aaagatatcc tctctggagc 3960
ttaagaatgt ccgcttgaat aacagatact ttcttgaagc ggacctaagc aaatttgata 4020
aatctcaggg tgagctgcac ctagagtttc agagagagat actccttgcg ctgggctttc 4080
cagcgccgct gacgaattgg tggtctgatt ttcatcgcga ttcttattta tcagaccctc 4140
atgccaaggt gggaatgtcc gtttccttcc aacgcagaac tggtgacgcg tttacatatt 4200
tcggtaatac tcttgtcact atggctatga ttgcatatgc ctctgatcta agtgactgtg 4260
actgtgcaat attttcagga gatgattctt taatcatctc taaagttaag ccagtcctgg 4320
ataccgatat gtttacgtct ctcttcaata tggagataaa agtcatggac cctagtgtgc 4380
cctacgtttg tagtaagttt ctcgtcgaaa ctgaaatggg caatttggtg tctgtaccag 4440
atcctctgag agagatccag cgcttagcta agcgaaagat tctgcgtgat gaacagatgc 4500
tcagagcaca tttcgtttcc ttctgtgatc gaatgaagtt tattaatcaa cttgatgaga 4560
agatgattac gacgctctgt cattttgttt atctgaaata tgggaaagaa aaaccttgga 4620
ttttcgagga ggttagagct gctcttgcgg ctttttcttt atactccgag aatttcctga 4680
ggttctctga ttgctactgt accgaaggca tcagagttta tcagatgagc gatcctgtat 4740
gtaagttcaa acgcaccacg gaagagcgta aaactgatgg tgactggttt cacaactgga 4800
agaatccaaa gtttcctggt gtgttagaca aagtctacag aaccattgga atttattcct 4860
cggactgtag tactaaggag ctccctgtca aacggatcgg acgtttacat gaggcccttg 4920
agcgtgagtc actcaaatta gctaatgatc gtaggaccac acaacgcttg aaaaagaagg 4980
tcgacgatta cgctaccggt agaggaggcc taacgtcagt tgatgctttg ctcgtgaagt 5040
cccattgtga gacttttaag ccctctgatc tgagatgatc ggttctatga tatatgaacc 5100
taagctgtga acagcccttt ggttaaggtt aaaaactcct ggtcaggcag accactttgg 5160
ctaagtttaa aagctgggga tcctctagag tccgcaaatc accagtctct ctctacaaat 5220
ctatctctct ctattttctc cagaataatg tgtgagtagt tcccagataa gggaattagg 5280
gttcttatag ggtttcgctc atgtgttgag catataagaa acccttagta tgtatttgta 5340
tttgtaaaat acttctatca ataaaatttc taattcctaa aaccaaaatc cagtgacctg 5400

-continued

```
caggcatgca agcttgcatg cctgcaggtc gactctagag gatccccggt cactggattt   5460
tggttttagg aattagaaat tttattgata gaagtatttt acaaatacaa atacatacta   5520
agggtttctt atatgctcaa cacatgagcg aaaccctata agaaccctaa ttcccttatc   5580
tgggaactac tcacacatta ttctggagaa aatagagaga gatagatttg tagagagaga   5640
ctggtgattt gcggactcta gaggatcccc gggtaccgag ctcgaattct cgagcagagg   5700
tctcacacag agacaagcgc atcacttaac acaattaaag atcaaatcac cagcgagctc   5760
gccgttaaag caatactcaa aggacttctt gtgtcgtgtt aaggcaacca aacagtactc   5820
ctcatgttta aacaaatcac atttggtcga cttaagccga accaaagtga cgttgtcaac   5880
agagatccct tgcgcttcgt gtactgtttt tatgtgtcca tcaatccagt ccttgctcac   5940
gggaaaatcc ttagccctcg tttgaagggc cgctttatca gcttgagtca tcgtaagata   6000
cgttctgttc ggatcaatag tgacctgcaa accagaagta atacgacgct tcgtgagact   6060
tctagaaact ttggactcag atgtccagga ttgatacttc gtgtccctat taccgcattt   6120
acgcttcagc agattaacag cagcgataac atcttgcgga caccggtaag tcttgtgaac   6180
aacgtcacgg cgatcatatt gcagattacc gtggagcaat ttaaaacccg cgtcacgaga   6240
cttgaacgaa atctgctctg tgtccccaaa ggcaagaact tgtgaacatt tagacagagc   6300
agccaccacc aggagttgac cataatgtag taaaccagcc tcatcaacaa gcagcctatg   6360
acaggacggt acaccgtgca tgatcgcaga atccgcggtg cgcacaacgt ccaaagctac   6420
cttggaatta taagtgtcag ggaataaagc catcctgacg tcctcggccg atttacgatt   6480
cgccgtcaca attaggtcct ctcccatacg gaatgcatct tttatggcag tggttttacc   6540
gcatcccgca actccatcaa ccatggaaat atcgcatgta gggacagaaa ctttggcgct   6600
agcttctgca atgtccctca agttagagca tgcacatgtt ttatcaacaa tgtacgtttc   6660
atctgcgtgc ttcggaccta aaccatgctc attatatcca acagtgtaat cgtatttttt   6720
aggatacaac cagttaccgt tggccaaatg gacattcacc atatcgtcta tgcgatggta   6780
ggtctcaaag atgctcttat ttgcgatctc acttccgcga ccgccggaaa tgtcccatag   6840
gtgacgaaga ttagactcgg agttgttatg taatctctta caataacgca caaattcctt   6900
catggctccg tgtctagata tgccacgagg gtccgttggt acctcaacag acacctcggc   6960
atccgggacc acatcagtca ccggtttaac gtcatcactg acggactcag ggctcgaact   7020
ctcaggggca tcatgaaact cctcctgagg tatctcagca gctggcggga ctttcgcctt   7080
cttcttcgag cgcttggtct tggctgtctg cacttcatgc tccagccggt cgaataagtc   7140
ctcttcagtc caaaacgttc tcaaacgtga tatcggtaca gaatcttgct caaattcttc   7200
aacgtttgag agacgagtca gaaacttaaa actgtccgca taagaatcca gacgtagtag   7260
gggaaatctg ctagccaatg ttctcagcca tcctactttc gccctggatg aatctccacc   7320
ccaccaaaac ctagttttga agtgatggca ccaacctttc cattccatcc catcgcggag   7380
ggccgtaagc ttttcgtact tttgatacag attcaaagtc aaagcaaagg ccactagatg   7440
ataatcttca atgtctaagc gctcaccagc catgatagcc tgaccgttaa taataacagt   7500
cgacgacttg gcggataaga tagatgcgac agctttcatg ttctcagtcc attctttact   7560
ttccttgaaa catctgaaag ctatctcctc tacctctctc actgtggttt tggcgacgcg   7620
cacacatttc cagcgattga gactccagtc ttcaggtatt gagaccccta cgtacttaga   7680
tatgtcttca aaccatacac agtgacgtag tgtctcccgg gggcagcgta aatttgtagc   7740
```

-continued

```
gatgatctta taggtcatga tgttacattt cagcatttcg cgctccaaca gataggtggt   7800
tccatcgatg caatgcaccg actcggtgaa aaatgagccc aaatcttgcc atccgtggat   7860
gtaagataat gtgctttcat tttcaaaatc gaatttgatc acctcatccg cgcctgaccc   7920
gtcacgttgc cagtgacatt taagcaaggg aagaaaaccc tcgcggtcaa acaacatggc   7980
gccgtcgaac ataacggtac cacgtagtac gcgtactcca tgcgaatgca tggcgtcaca   8040
cagaccttgg aagcccatat cataaccgcc gtggatacag atagcccaat cagcttggac   8100
atcacaatct tgagctcggt taagacaaaa gttcgggact tcatcgaaat catcgctttc   8160
ttgcaaaatt tttcgcatgc ggcacatcct ctcctcatgt cgggcagcgt ctctaacacc   8220
caacacagga caacaactgt gcaccctttt atcccttctt gaaaagtgat gccaccaaga   8280
ccctccgaaa tctataacgg ggtcttcagg gggaaaactg tcgagacagt cataatgctc   8340
cgctacacgc agagcaccag ccaggctatg ggcgcatga tactgctgag tcaaatttaa   8400
gtcaaaggca ccaccataac ggtcacggaa ggcgtcagcc tcctcaatag agagcttatt   8460
gcgaacgttg attttcttag accttttcgc gtattcaatc tgcgcagata actgttgcgc   8520
aacctgattg tctacgatgt cttgggcact ctggctgtca gcacccttct cagcaatcaa   8580
cttcagcaaa tcgatagaac ttgacatttt gttggtgaaa aacaaagaac aagtagcaga   8640
accgtggtcg aggtcctctc caaatgaaat gaacttcctt atatagagga agggtcttgc   8700
gaaggatagt gggattgtgc gtcatccctt acgtcagtgg agatatcaca tcaatccact   8760
tgctttgaag acgtggttgg aacgtcttct ttttccacga tgttcctcgt gggtgggggt   8820
ccatctttgg gaccactgtc ggtagaggca ttcttgaacg atagcctttc ctttatcgca   8880
atgatggcat ttgtagaagc catcttcctt ttctactgtc ctttcgatga agtgacagat   8940
agctgggcaa tggaatccga ggaggtttcc cgatattacc ctttgttgaa aagtctcaat   9000
agccctctgg tcttctgaga ctgtatcttt gatattcttg gagtagacga gagtgtcgtg   9060
ctccaccatg ttgaccgggt ggtcagtccc ttatgttacg tcctgtagaa accccaaccc   9120
gtgaaatcaa aaaactcgac ggcctgtggg cattcagtct ggatcgcgaa aactgtggaa   9180
ttgatcagcg ttggtgggaa agcgcgttac aagaaagccg ggcaattgct gtgccaggca   9240
gttttaacga tcagttcgcc gatgcagata ttcgtaatta tgcgggcaac gtctggtatc   9300
agcgcgaagt ctttataccg aaaggttggg caggccagcg tatcgtgctg cgtttcgatg   9360
cggtcactca ttacggcaaa gtgtgggtca ataatcagga agtgatggag catcagggcg   9420
gctatacgcc atttgaagcc gatgtcacgc cgtatgttat tgccgggaaa agtgtacaat   9480
tcactggccg tcgttttaca acgtcgtgac tgggaaaacc ctggcgttac ccaacttaat   9540
cgccttgcag cacatccccc tttcgccagc tggcgtaata gcgaagaggc ccgcaccgat   9600
cgcccttccc aacagttgcg cagcctgaat ggcgaatgnn nnnnnaattc agtacattaa   9660
aaacgtccgc aatgtgttat taagttgtct aagcgtcaat ttgtttacac cacaatatat   9720
cctgccacca gccagccaac agctccccga ccggcagctc ggcacaaaat caccactcga   9780
tacaggcagc ccatcagnnn nnnnnnnnnn nnnnnnnnnn nnnnnnnnnn nnnnnnnnnn   9840
nnnnnnnnnn nnnnnnnnnn nnnnnnnnnn nnnnnnnnnn nnnnnnnnnn nnnnnnnnnn   9900
nnnnnnnnnn nnnnnnnnnn nnnnnnnnnn nnnnnnnnnn nnnnnnnnnn nnnnnnnnnn   9960
nnnnnnnnnn nnnnnnnnnn nnnnnnnnnn nnnnnnnnnn nnnnnnnnnn nnnnnnnnnn  10020
```

-continued

```
nnnnnnnnnn nnnnnnnnnn nnnnnnnnnn nnnnnnnnnn nnnnnnnnnn nnnnnnnnnn  10080

nnnnnnnnnn nnnnnnnnnn nnnnnnnnnn nnnnnnnnnn nnnnnnnnnn nnnnnnnnnn  10140

nnnnnnnnnn nnnnnnnnnn nnnnnn                                       10166
```

EXPRESSION CASSETTE FOR TRANSFORMATION COMPRISING A MODIFIED VIRAL SEQUENCE DRIVEN BY A SUITABLE PROMOTER

CROSS-REFERENCE TO RELATED APPLICATIONS

This application is a continuation of patent application U.S. Ser. No. 10/609,207, filed Jun. 26, 2003, which is a continuation of U.S. Ser. No. 09/316,622, filed May 21, 1999; which claims priority from provisional patent application U.S. Ser. No. 60/086,526, filed May 22, 1998.

This invention was made with United States government support awarded by the following agency:

NIH Grant No: GM35072

The United States government has certain rights in this invention.

BACKGROUND OF THE INVENTION

RNA viruses have been found to be valuable tools in the phenotypic and genotypic transformation of targeted cells and tissues. See, e.g., U.S. Pat. No. 5,500,360, which teaches novel viral RNA expression vectors. It has been shown that the RNA of the genome of an RNA virus can be modified to include an exogenous RNA segment and that the modified RNA can be introduced into a host cell, replicated therein, and thereby express the exogenous RNA segment.

Current methods of inoculating a host cell with modified RNA viruses involve the in vitro transcription of a particular strand followed by the introduction of the resulting RNA transcripts into the host cell. One problem with the current inoculation method is that the RNA rapidly degrades which causes a low efficiency of infection. In addition, the preparation of the in vitro RNA transcripts is expensive and time consuming.

Further, with the advent of transformation and the genetic engineering of plants, much concern has arisen concerning the potential hazard of the dispersal of dangerous traits into the environment. For example, genes increasing the stress tolerance and/or herbicide resistance of an agriculturally important crop could theoretically "leak" to surrounding less desirable and damaging plants, e.g., through pollen, mechanical or insect dispersal. This phenomenon could create a novel species of "super-weed" which could wreak havoc on the agricultural industry. Existing RNA virus-based vectors can spread to non-target plants by mechanical means and/or by insects. Such spread can be prevented by using vectors that can replicate and/or move only in target plants expressing the appropriate trans-acting factors. Accordingly, there remains a need for less expensive and more efficient methods of transformation of target cells and tissues. Moreover, there is a need for a novel method of transformation which alleviates the potential dangers associated with the unwanted spread of engineered traits into the environment.

BRIEF SUMMARY OF THE INVENTION

The subject invention pertains to improved materials and methods for transforming host cells which involve transfecting said cells with a DNA-launching platform. One aspect of the subject invention pertains to a DNA-launching platform which encodes a modified viral RNA molecule downstream of DNA-dependent RNA polymerase (pol) promoter, whereby the DNA-launching platform is capable of being introduced into a host cell and effectively "launching" said modified viral RNA molecule into the host cell such that it is replicated and expressed therein. The term "modified viral RNA molecule" as used herein refers to a viral RNA which has been changed from its natural state. Examples of changes of viral RNA include, but are not limited to, removal of a part of viral RNA genome, insertion or substitution of an exogenous RNA, etc. The exogenous RNA segment can be located in a region of the viral RNA molecule such that it does not disrupt the RNA replication. Techniques for such manipulations have been well known to those of ordinary skill in the art for many years. Preferably, the modified viral RNA molecule further comprises a ribozyme which is located in the proximity of the 3' end of the modified viral RNA molecule. The viral segment may have the ability to be replicated with or, alternatively, without the presence of trans-acting viral replicating elements.

Another aspect of the subject invention pertains to a method of genotypically or phenotypically modifying a host cell, comprising introducing a DNA-launching platform which encodes a viral RNA molecule and an exogenous RNA segment in a location which does not disrupt the replication of said viral RNA segment or said exogenous RNA segment, whereby the exogenous RNA segment confers a detectable trait in the host cell. The subject invention applies to a wide array of plant cells.

Still a further aspect of the subject invention pertains to cells in which the DNA-launching platform of the subject invention has been introduced.

Yet another aspect of the subject invention pertains to a plant comprising cells transfected with the DNA-launching platform.

The novel methods and materials of the subject invention provide a greater inoculation efficiency of RNA viruses because use of DNA-launching platforms of the subject invention are more resistant to degradation than RNA inocula, and because each DNA platform produces multiple RNA transcripts over an extended period of time. As the DNA-launching platform provides a genetically stable in planta archive copy of a desired vector construct, the continuing transcription of said DNA platform will repeatedly reinoculate the host cell with the desired construct. This serves to counteract genetic instability problems that have inhibited the expression of some genes from vectors based on plant and animal RNA viruses. Further, the inoculation methods of the subject invention provide a much simpler means of producing inocula in bulk for large scale use, which is cheaper and more efficient than inoculating with in vitro RNA transcripts.

Legend for FIGS. 5-10

35S=CaMV35S promoter t=termination/polyA+sequences

Rz=ribozyme

NOS=NOS promoter

OOA=origin of assembly

FG=foreign gene

Figure 11A:
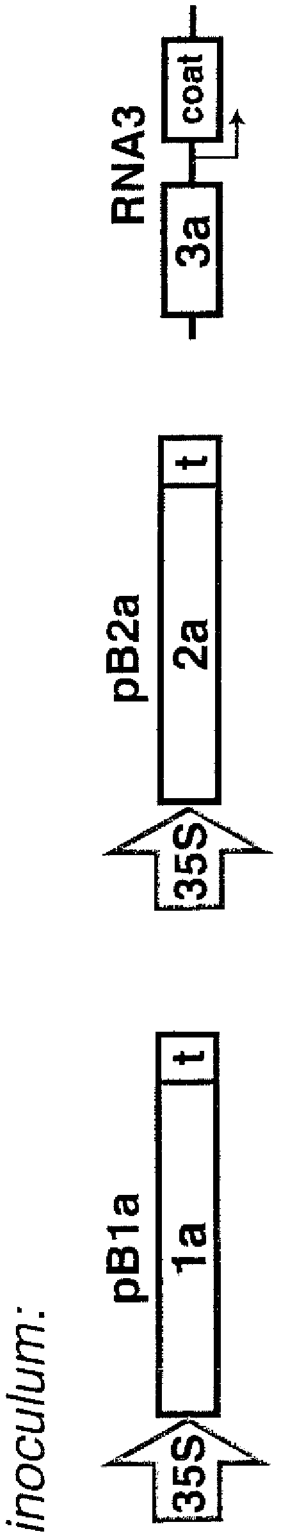
Figure 11B:
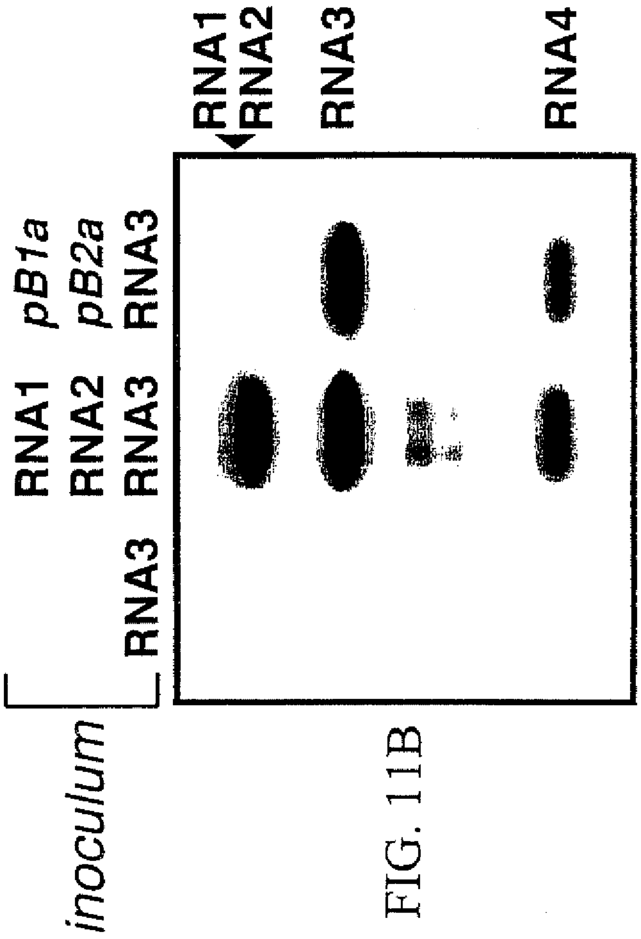

FIG. 11 shows that BMV replication factors support efficient RNA3 replication in protoplasts.

Figure 12A:
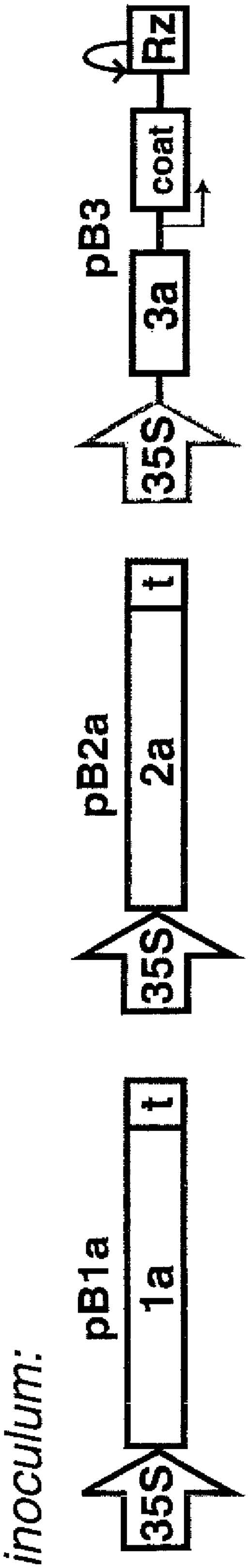
Figure 12B:
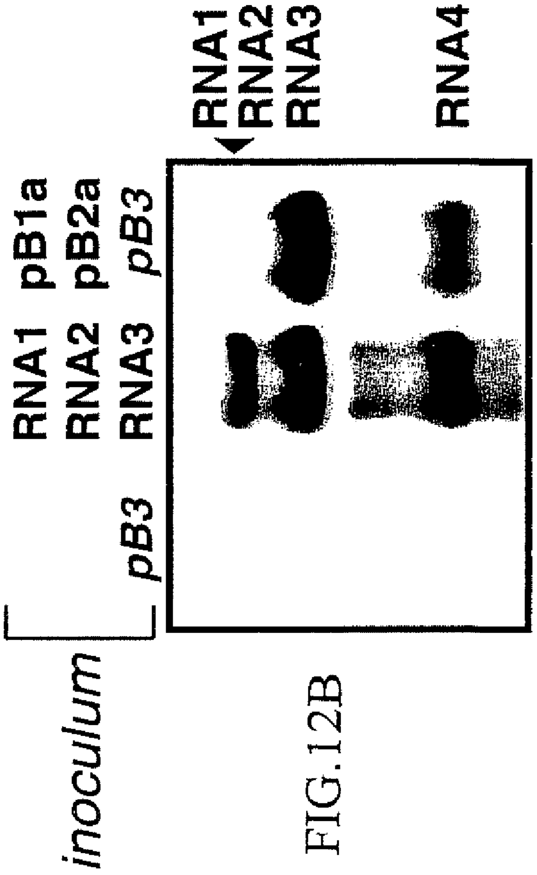

FIG. 12 shows the efficient replication of launched BMV RNA3 in protoplasts.

FIG. 13 shows transgenic expression of BMV 1a and 2a mRNAs in *N. tabacum* and *N. benthamiana.*

Figure 14A:
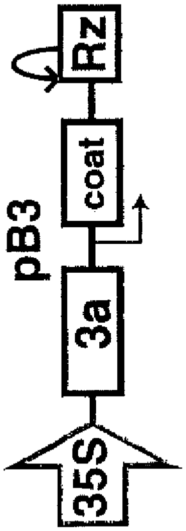
Figure 14B:
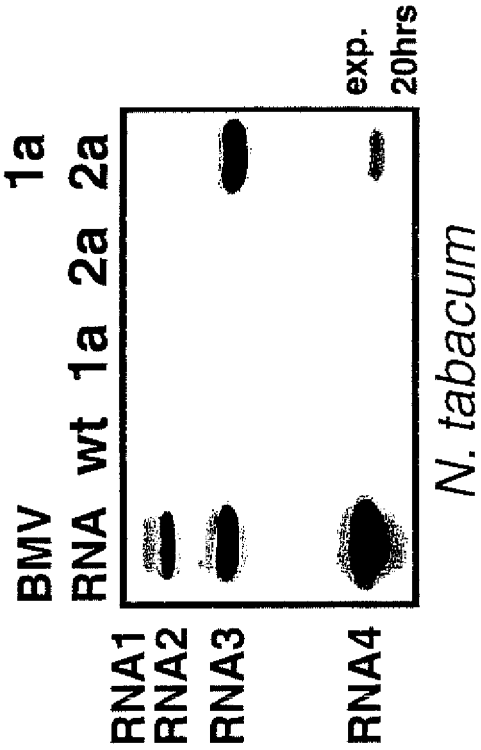
Figure 14C:
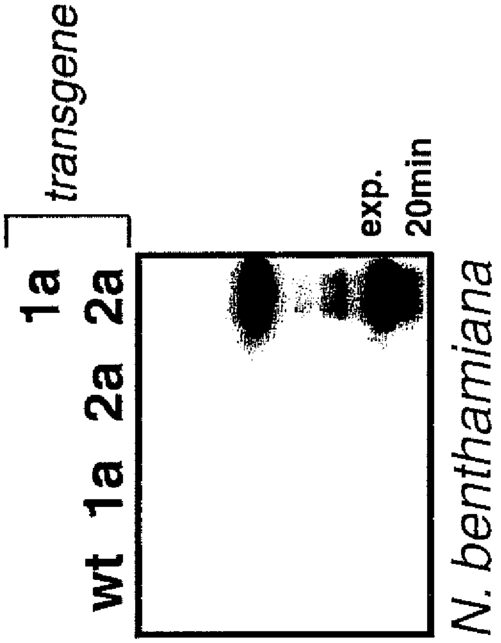

FIG. 14 shows the efficient replication of launched BMV RNA3 in (1a+2a)-transgenic plants.

Figures 15A, 15B, 15C:
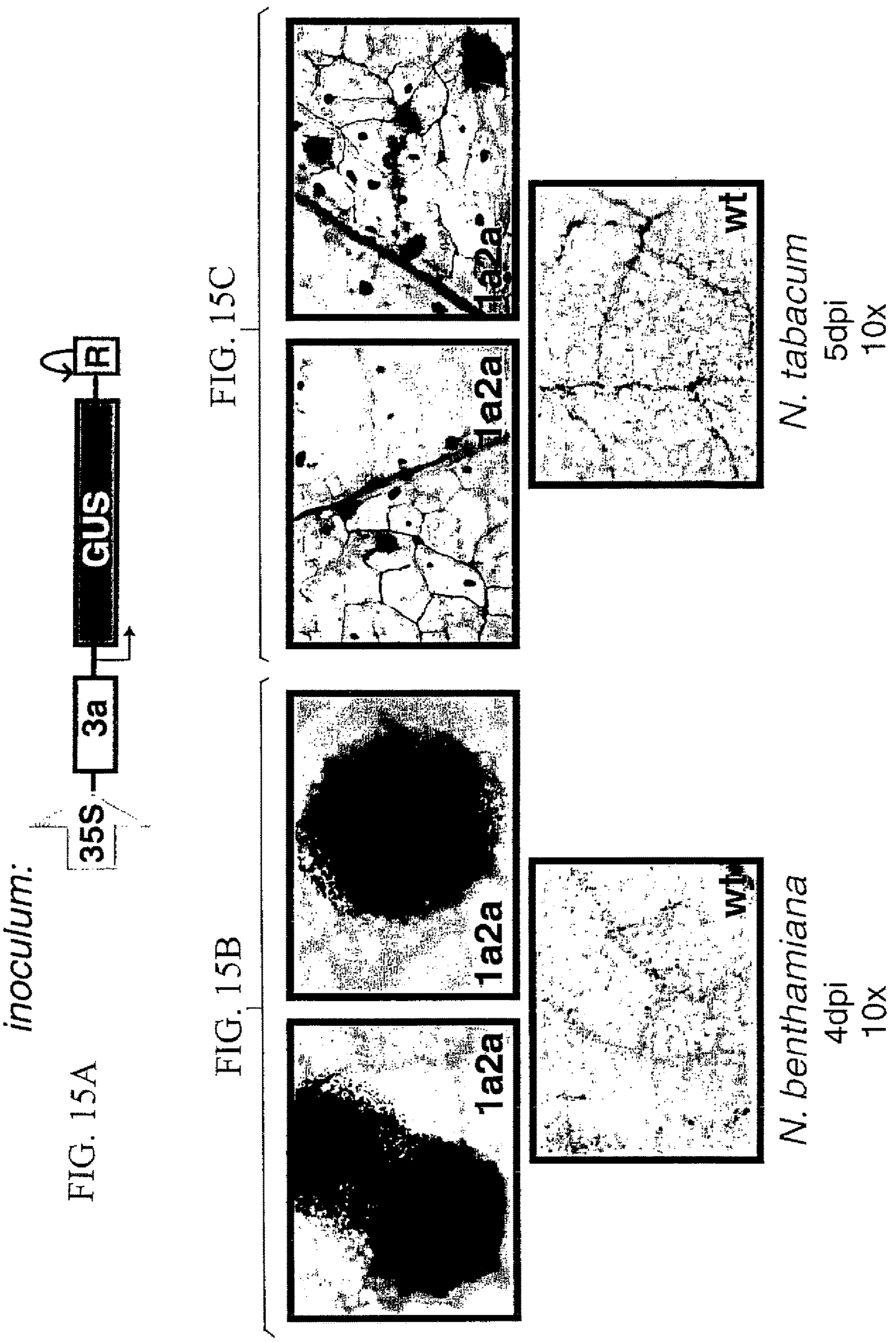

FIG. 15 shows the successful GUS expression from the launched BMV RNA3 in (1a+2a)-transgenic plants.

FIG. 16 shows the successful GUS expression from the launched BMV RNA3 in protoplasts.

Figure 17A:
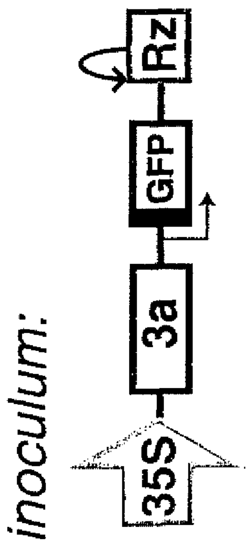
Figure 17B:
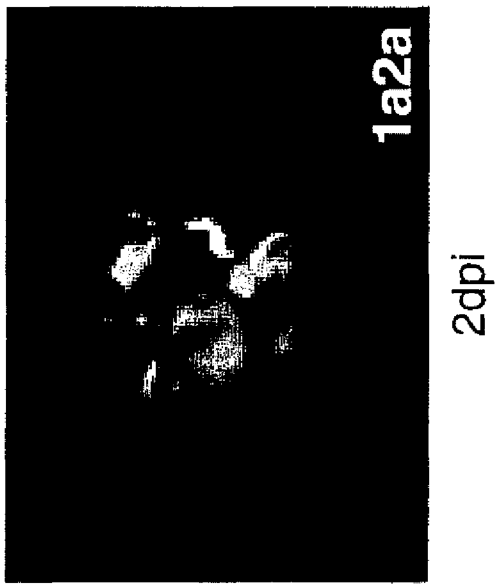

FIG. 17 shows the successful GFP expression from the launched BMV RNA3 in (1a+2a)-transgenic plants.

Figure 18B:
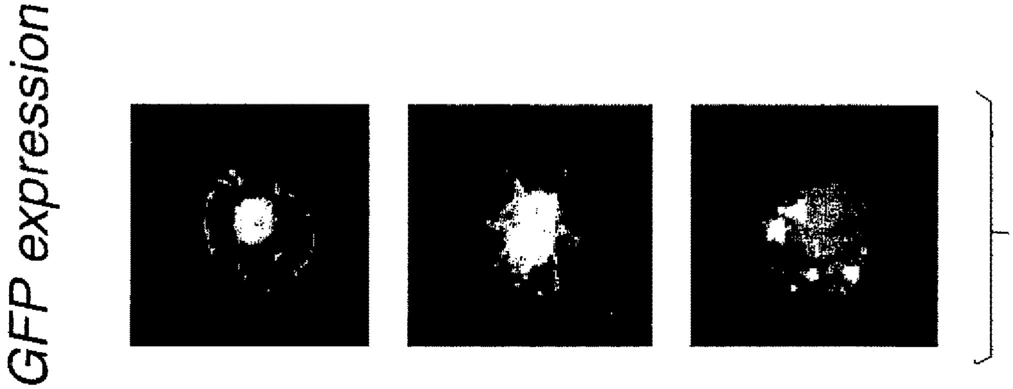
Figure 18A:
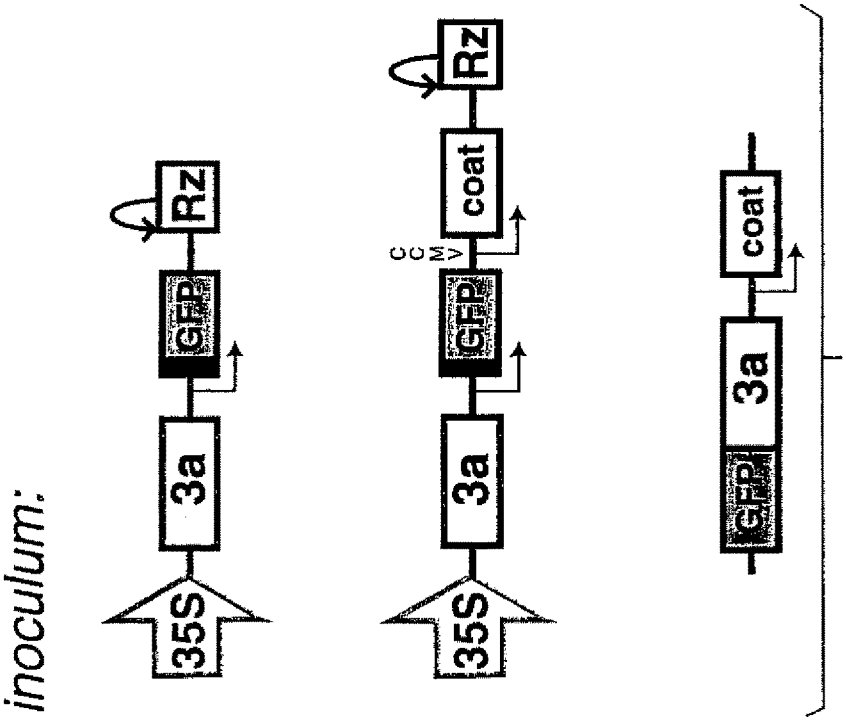

FIG. 18 shows the successful GFP expression from the launched BMV RNA3 in protoplasts.

Figure 19B:
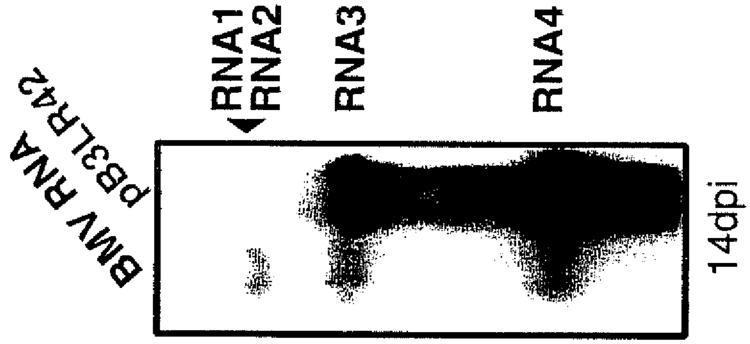
Figure 19A:
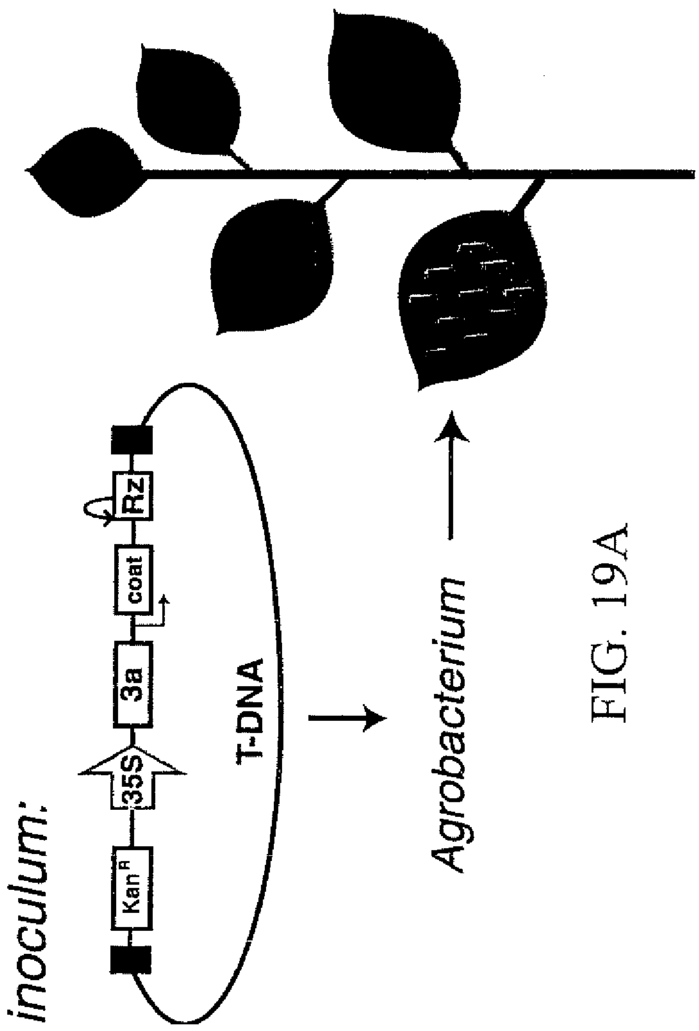

FIG. 19 shows the efficient replication of the launched BMV RNA3 in (1a+2a)-transgenic *N. benthamiana* using *Agrobacterium* inoculation.

Figure 20:
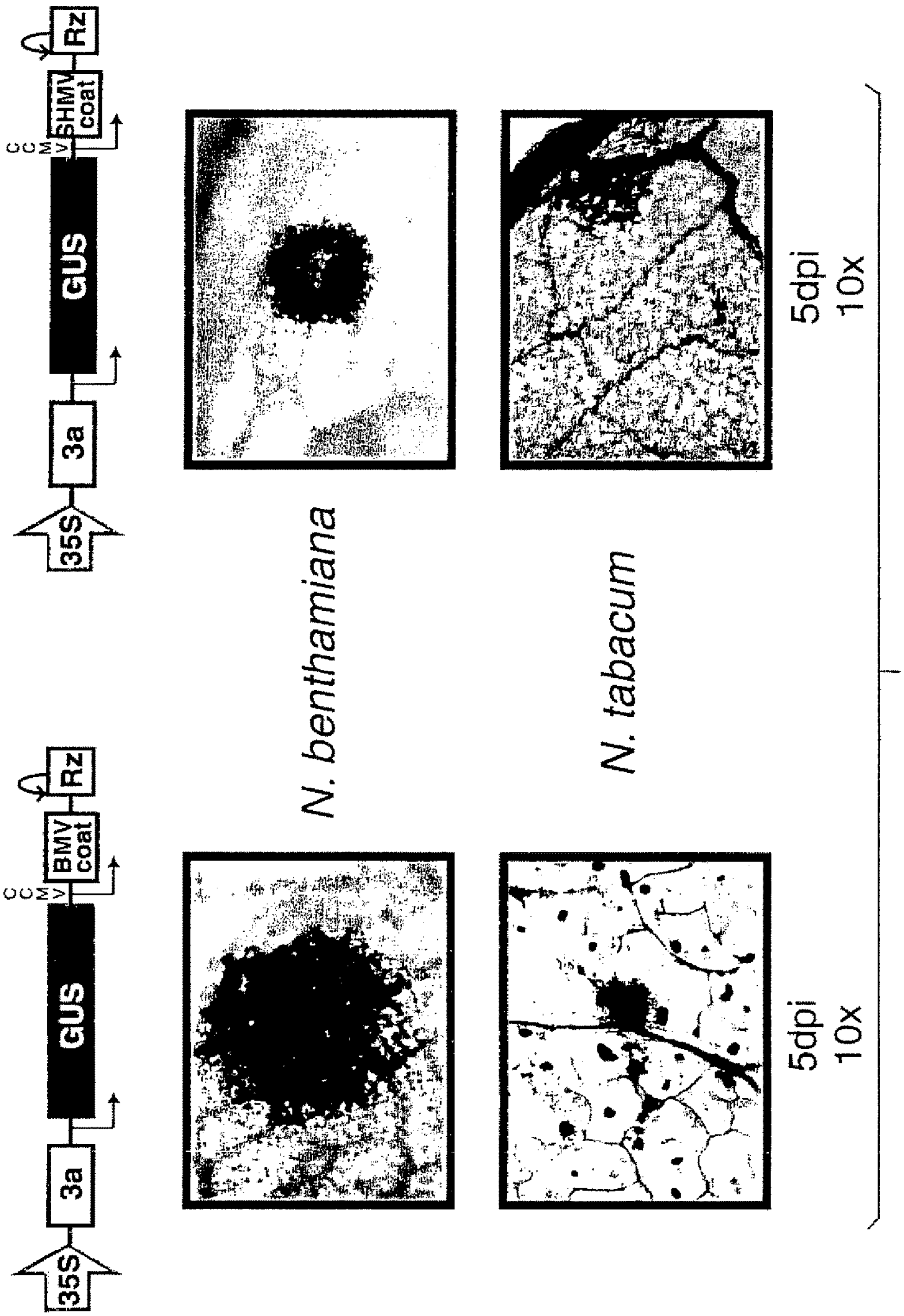

FIG. 20 shows the successful GUS expression from the launched BMV RNA3 having the SHMV coat protein in (1a+2a)-transgenic plants.

Figure 21:
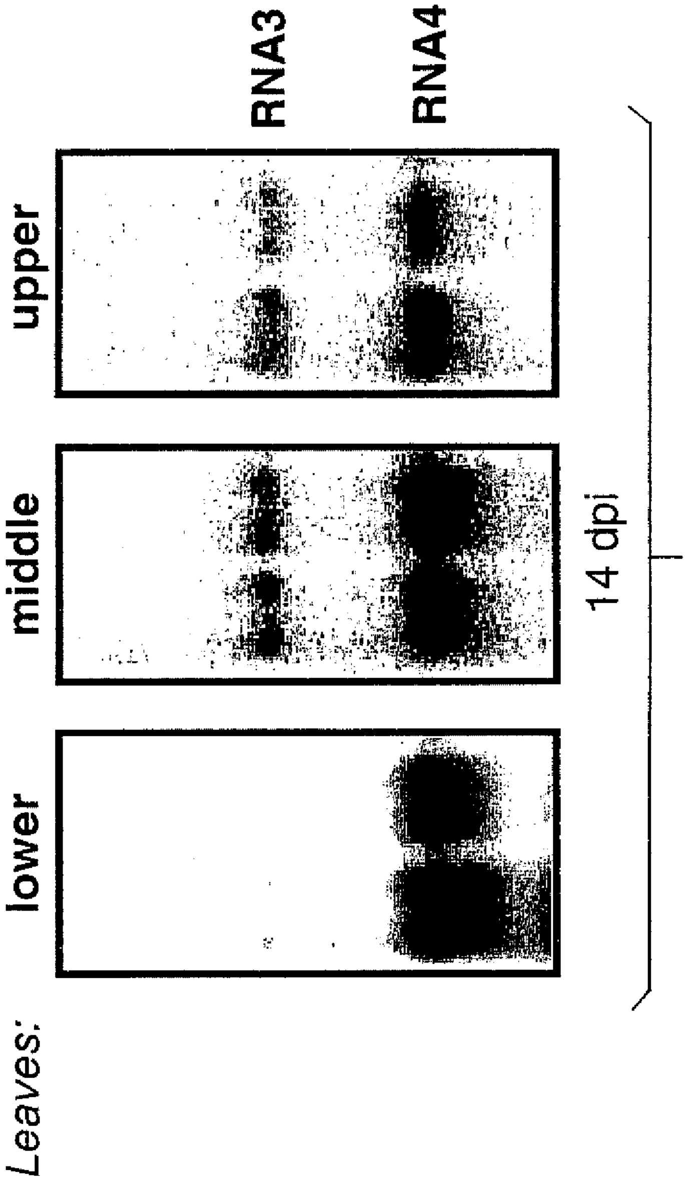

FIG. 21 shows that launched BMV replicates, moves cell-to-cell, and spreads long distances in (1a+2a)-transgenic plants.

Figure 22:
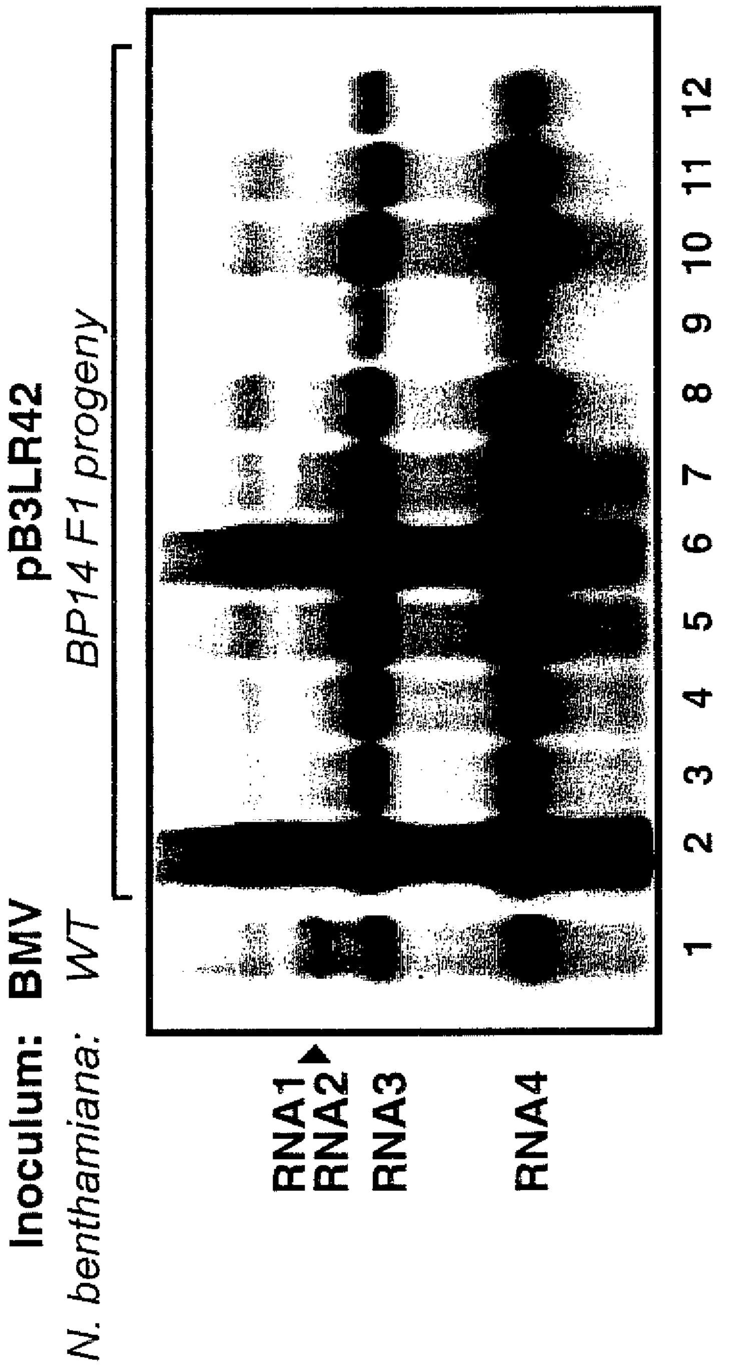

FIG. 22 shows transfection of progeny from (1a+2a)-transgenic *N. benthamiana* with BMV RNA3 DNA-launching platform and localization of the launched RNA3 to the roots.

BRIEF DESCRIPTION OF THE SEQUENCES

SEQ ID NO. 1: pB1LR2—partial nucleotide sequence includes BMV 1a expression cassette.

SEQ ID NO. 2: pB1LR3—partial nucleotide sequence includes BMV 1a expression cassette.

SEQ ID NO. 3: pB2LR4—partial nucleotide sequence includes BMV 2a expression cassette.

SEQ ID NO. 4: pB2LR5—partial nucleotide sequence includes BMV 2a expression cassette.

SEQ ID NO. 5: pB12LR6—partial nucleotide sequence includes BMV 1a and 2a expression cassettes.

SEQ ID NO. 6: pB12LR7—partial nucleotide sequence includes BMV 1a and 2a expression cassettes.

SEQ ID NO. 7: pB12LR8—partial nucleotide sequence includes BMV 1a and 2a expression cassettes.

SEQ ID NO. 8: pB12LR9—partial nucleotide sequence includes BMV 1a and 2a expression cassettes.

SEQ ID NO. 9: is a primer useful for PCR of the GFP fragment in pB3Tp10.

SEQ ID NO. 10: is a primer useful for PCR of the GFP fragment in pB3Tp10.

DETAILED DISCLOSURE OF THE INVENTION

To facilitate understanding of the invention, certain terms used throughout are herein defined. The term “RNA virus” as used herein means a virus whose genome is RNA in a double-stranded or single-stranded form, the single strand being a (+) strand or (−) strand.

The terms “transfection” or “transfected” as used herein means an introduction of a foreign DNA or RNA into a cell by mechanical inoculation, electroporation, agroinfection, particle bombardment, microinjection, or by other known methods.

The terms “transformation” or “tansformed” as used herein means a stable incorporation of a foreign DNA or RNA into the cell which results in a permanent, heritable alteration in the cell. Accordingly, the skilled artisan would understand that transfection of a cell may result in the transformation of that cell.

The term “launched” as used herein refers to a polynucleotide that has been transcribed from a DNA-launching platform, as described herein and, preferably, replicated.

The term “cis-acting element” as used herein denotes that portion of the RNA genome of an RNA virus which must be present in cis, that is, present as a part of each viral strand as a necessary condition for replication of that strand. Virus replication may depend upon the existence of one or more trans (diffusible) elements which interact with the cis-acting element to carry out RNA replication. If trans-acting elements are necessary for replication, they need not be present or coded for on the modified viral RNA provided, but may be made available within the infected cell by some other means. For example, the trans-acting replication functions may be provided by other, unmodified or modified, components of the viral genome transfected into the cells simultaneously with the modified RNA. The same approach can be used for other trans-acting functions including movement protein, coat protein, and other functions. The target cell may also be premodified, for example, cells may have been previously transformed to provide constitutive expression of the trans-acting functions from a chromosome. The cis-acting element is composed of one or more segments of viral RNA which must be present on any RNA molecule that is to be replicated within a host cell by RNA replication. The segment will most likely be the 5' and 3, terminal portions of the viral RNA molecule, and may include other portions and/or virus open reading frames as well. The cis-acting element is accordingly defined in functional terms: any modification which destroys the ability of the RNA to replicate in a cell known to contain the requisite trans-acting elements, is deemed to be a modification in the cis-acting element. Conversely, any modification, such as deletion or insertion in a sequence region which is able to tolerate such deletion or insertion without disrupting replication, is a modification outside the cis-acting element. As is demonstrated herein, using the example of BMV which is known and accepted by those skilled in the art to be a functional example from which substantial portions of an RNA virus molecule may be modified, by deletion, insertion, or by a combination of deletion and insertion, without disrupting replication.

“Exogenous RNA” is a term used to describe a segment or component of RNA to be inserted into the virus RNA to be modified, the source of the exogenous RNA segment being different from the RNA virus itself. The source may be another virus, an organism such as a plant, animal, bacteria, virus, or fungus. The exogenous RNA may be a chemically synthesized RNA, derived from a native RNA, or it may be a combination of the foregoing. The exogenous RNA may provide any function which is appropriate and known to be provided by an RNA segment. Such functions include, but are not limited to, a coding function in which the RNA acts as a messenger RNA encoding a sequence which, when translated by the host cell, results in synthesis of a peptide or protein having useful or desired properties; the RNA segment may also be structural, as for example in ribosomal RNA; it may be regulatory, as for example with small nuclear RNAs or anti-sense RNA; or it may be catalytic. One skilled in the art will understand that the exogenous RNA may encode, for example, a protein which is a key enzyme in a biochemical pathway, which upon expression effects a desirable phenotypic characteristic, such as altering cell metabolism. Further, the exogenous RNA may encode a protein involved in transcriptional regulation, such as zinc finger, winged-helix, and leucine-zipper proteins. A particularly interesting function is provided by anti-sense RNA, sometimes termed (−) strand RNA, which is in fact a sequence complementary to another RNA sequence present in the target cell which can, through complementary base pairing, bind to and inhibit the function of the RNA in the target cell.

The term “non-viral” is used herein in a special sense to include any RNA segment which is not normally contained within the virus whose modification is exploited for replication and expression, and is therefore used synonymously with “exogenous”. Accordingly, a gene derived from a different virus species than that which is modified is included within the meaning of the terms “non-viral” and “exogenous” for the purposes of describing the invention. For example, a non-viral gene as the term is used herein could include a gene derived from a bacterial virus, an animal virus, or a plant virus of a type distinguishable from the virus modified to effect transformation. In addition, a non-viral gene may be a structural gene derived from any prokaryotic or eukaryotic organism.

In one embodiment, the subject invention concerns a novel method of transfecting a host cell which uses a DNA-launching platform to introduce viral RNA into the cell. The subject invention is directed towards a method of transfection employing a DNA-launching platform which encodes a modified viral RNA molecule comprising an RNA viral component attached to an exogenous RNA component and a DNA-dependent RNA pol promoter. The DNA-dependent RNA pol promoter is preferably but not necessarily fused within up to 10 nucleotides of the 5' transcriptional start site of the modified viral RNA molecule, and more preferably within up to 5 nucleotides of the 5' transcriptional start site. Expression of the DNA-launching platform produces transcripts of the modified viral RNA molecule that are then capable of RNA replication in the presence of replication factors, which can be present in the modified viral RNA and/or may be supplied in trans by other means including expression from chromosome or supplied on different launching plasmids. When the modified viral RNA is replicated, the exogenous RNA can be replicated as well. Further, the exogenous RNA can be expressed in the cell, thereby providing a predetermined phenotypic characteristic. In a preferred embodiment, the DNA launching platform further comprises a nucleotide sequence encoding a self-cleavable ribozyme situated proximate to the 3' end of said RNA molecule. As would be readily apparent to those skilled in the art, known ribozymes may be used in accordance with the subject invention. In a preferred embodiment, the ribozyme cleaves the modified RNA viral molecule at the 3' region. The 3' region can consist of up to 30 nucleotides upstream or downstream of the 3' end; and preferably consists of up to 10 nucleotides upstream or downstream of the 3' end. In a more preferred embodiment, the ribozyme cleaves the modified RNA viral molecule precisely at the 3' end. Other known regulatory sequences, e.g., promoters and/or termination sequences, may also be substituted for and/or included on the DNA-launching platform. A suitable restriction site can be introduced proximate to the 3' end of the modified viral RNA molecule sequence and the DNA molecule can be cleaved by an appropriate restriction enzyme prior to transfection. The term “DNA-launching platform” as used herein is intended to mean a DNA molecule, circular or linear, which has a coding region comprising a segment encoding a modified viral RNA segment, and fiber, which is capable of being delivered into a cell and subsequently transcribed.

Possible regulatory sequences can include, but are not limited to, any promoter already shown to be constitutive for expression, such as those of viral origin (CaMV 19S and 35S) or so-called “housekeeping” genes (ubiquitin, actin, tubulin) with their corresponding termination/polyA+sequences. Also, seed- and/or developmentally-specific promoters, such as those from plant fatty acid/lipid biosynthesis genes (ACPs, acyltransferases, desaturases, lipid transfer protein genes) or from storage protein genes (zein, napin, cruciferin, conglycinin, phaseolin, or lectin genes, for example), with their corresponding termination/polyA+sequences can be used for targeted expression. In addition, the gene can be placed under the regulation of inducible promoters and their termination sequences so that gene expression is induced by light (rbcS-3A, cab-1), heat (hsp gene promoters) or wounding (mannopine, HGPGs). It is clear to one skilled in the art that a promoter may be used either in native or truncated form, and may be paired with its own or a heterologous termination/polyA+sequence.

In a particularly preferred embodiment, the subject invention is directed toward a method of genotypically or phenotypically modifying a cell comprising the following steps: a) forming a cDNA molecule of a virus RNA, or of at least one RNA component if the RNA virus is multipartite, the viral RNA having been modified to contain a DNA segment encoding a non-viral RNA component situated in a region able to tolerate such insertion without disrupting replication of the RNA product encoded thereby; b) cloning modified cDNA into a DNA-launching platform; and c) transfecting a suitable host cell with said DNA-launching platform. In a most preferred embodiment, the method further comprises pretransforming a plant with trans-acting viral replication factors and/or other trans-acting factors. Such trans-acting factors may include viral movement proteins(s), coat protein(s), viral protease(s), and other structural and non-structural genes. In addition to stable expression of trans-acting factors, trans-acting factors may be introduced on separate expression plasmids or may be expressed from RNA transcripts. In a preferred embodiment such trans-acting factors do not replicate. Suitable host cells may include protoplasts, cells in suspension, or cells in tissues or whole organisms.

In a specific embodiment intended as an example of the broader teachings herein, the RNA viral segment can be derived from brome mosaic virus (BMV), whereby the DNA-launching platform comprises DNA encoding the RNA3 segment of the virus. Brome mosaic virus (BMV) is a member of the α virus-like super family of positive-strand RNA viruses of animals and plants, and has a genome divided among three RNAs. RNA1 and RNA2 encode the 1a and 2a proteins, respectively, which are necessary for a genomic RNA replication and subgenomic mRNA synthesis (see, e.g., U.S. Pat. No. 5,500,360, which to the extent not inconsistent herewith, is incorporated herein by reference). These proteins contain three domains conserved in all other members of the α virus-like super family. 1a (109 kDa) contains a c-proximal helicase-like domain and an n-proximal domain implicated in RNA capping, and 2a (94 kDa) contains a central polymerase-like domain. See, e.g., French and Ahlquist, (1988). 1a and 2a interact with each other and with cell factors to form a membrane bound viral RNA replication complex associated with the endoplasmic reticulums of infected cells. BMV RNA3, a 2.1-kb RNA, encodes the 3a protein (32 kDa) and coat protein (20 kDa), which are involved in the spread of BMV infection in its natural plant hosts but are dispensable for RNA replication. See U.S. Pat. No. 5,500,360. The 3a or coat protein gene of the RNA3 viral segment can be replaced with exogenous RNA, whereby it does not interfere with the replication element. Further, the exogenous RNA segment can be inserted downstream of an additional subgenomic promoter. Still further, cells or tissues can be pretransformed to express 1a, 2a, 3a, and coat protein, or any combination thereof, wherein DNA-launching platforms containing a foreign gene(s) with the necessary cis-acting components is transfected, such that the foreign gene is replicated and/or expressed.

In one embodiment, the host cell is pretransformed with BMV1 or BMV2 such that it is transgenically engineered to express 1a and 2a proteins. Preferably, the 5' and 3' ends of BMV1 and BMV2 are removed such that they are incapable of replication, but can express 1a and 2a to form a viral RNA replication complex associated with the endoplasmic reticulum of the host cell. Subsequent transfection of a DNA-launching platform comprising the RNA3 viral replication segment, as well as the exogenous RNA of interest, can produce the expression of said exogenous RNA while also preventing the undesired and dangerous spread of viral RNA spillage into the environment. That is, because a plant must have all 3 segments to form infectious BMV particle(s), problems associated with the environmentally hazardous escape of foreign genes through mechanical or insect dispersal of RNA virus vectors are avoided. One skilled in the art will readily appreciate that in the example of BMV that DNA-launching platforms could be also derived from either RNA1 or RNA2. For example, the sequence encoding the 1a protein could be replaced with an exogenous RNA; replication would require the expression of 1a (e.g., separate expression plasmid). In a preferred embodiment, the DNA-launching platform also comprises a ribozyme situated proximate to the 3' end of the modified RNA3, wherein said ribozyme cleaves the RNA3 at the 3' end. As would be readily apparent to the skilled artisan with the teachings contained herein, viral segments from other known viruses, and/or subviral agents, can be used to formulate DNA-launching platforms of the subject invention. One skilled in the art will appreciate that BMV is merely one representative example of the many viruses suitable for practicing the subject invention. It is widely accepted that principles on which the subject invention is based are broadly applicable to a myriad of viruses. Examples of other such viruses include, but are not limited to, alfalfa mosaic virus (AMV), barley stripe mosaic virus, cowpea mosaic virus, cucumber mosaic virus, reoviruses, polio virus, sindbis virus, vesicular stomatitis virus, influenza virus, retroviruses, and cowpea chlorotic mottle virus (CCMV) and any other viruses that replicate through RNA intermediates and from which a cDNA copy can be obtained. Specifically, as the other viruses are further characterized, those of skill in the art will readily appreciate the applicability of the teachings herein to other suitable viruses as well.

The skilled artisan would easily appreciate that known methods of introducing foreign DNA into cells can be used in accordance with the teachings of the subject disclosure. Such methods include, but are not limited to, mechanical inoculation, particle bombardment, agroinfection, electroporation, and microinjection, as well as other known methods.

Various aspects of the invention can be modified as needed, depending upon specific characteristics of the virus selected as the transforming and transfecting agent and of the RNA segment to be inserted. For example, the inserted gene need not be a naturally occurring gene, but may be modified, a composite of more than one coding segment, or it may encode more than one protein. The RNA may also be modified by combining insertions and deletions in order to control the total length or other properties of the modified RNA molecule. The inserted non-viral gene may be either prokaryotic or eukaryotic in origin. The inserted gene may contain its own translation start signals, for example, a ribosomal binding site and start (AUG) codon, or it may be inserted in a manner which takes advantage of one or more of these components preexisting in the viral RNA to be modified. Certain structural constraints must be observed to preserve correct translation of the inserted sequence, according to principles well understood in the art. For example, if it is intended that the exogenous coding segment is to be combined with an endogenous coding segment, the coding sequence to be inserted must be inserted in reading frame phase therewith and in the same translational direction.

It will be understood by those ordinarily skilled in the art that there may exist certain genes whose transfer does not result in obvious phenotypic modification of the recipient cell. Such may occur, for example, if the translation product of the non-viral gene is toxic to the host cell, is degraded or processed in a manner which renders it non-functional or possesses structural features which render it impossible for the host cell to translate in sufficient quantities to confer a detectable phenotype on the transformed cells. However, the invention does not depend upon any specific property of an RNA segment or gene being transferred. Therefore, the possible existence of RNA segments or genes which fail to confer a readily observable phenotypic trait on recipient cells or plants is irrelevant to the invention, and in any case will be readily recognizable by those of ordinary skill in the art without undue experimentation.

An exogenous RNA segment may be inserted at any convenient insertion site in any of the cDNA sequences corresponding to a viral RNA, or component RNA of a multipartite RNA virus, provided the insertion does not disrupt a sequence essential for replication of the RNA within the host cell. For example, for a virus whose coat protein is not essential for replication, an exogenous RNA segment may be inserted within or substituted for the region which normally codes for coat protein. As desired, regions which contribute to undesirable host cell responses may be deleted or inactivated, provided such changes do not adversely affect the ability of the RNA to be replicated in the host cell. For many single component and multipartite RNA viruses, a reduction in the rate of normal RNA replication is tolerable and will in some instances be preferred, since the amount of RNA produced in a normal infection is more than enough to saturate the ribosomes of the transformed cell.

Plant cells which are inoculated in culture will normally remain transfected as the cells grow and divide since the RNA components expressed from the DNA-launching platform are able to replicate and thus become distributed to descendant cells upon cell division. Plants regenerated from phenotypically modified cells, tissues, or protoplasts remain phenotypically modified. Similarly, plants transfected as seedlings remain transfected during growth. Optimal timing of application of the transfecting components will be governed by the result which is intended and by variations in susceptibility to the transfecting components during various stages of plant growth.

Many plant RNA viruses are seed transmitted from one generation to the next. This property can be exploited to effect genotypic transformation of a plant. That is to say, the modified RNA remains transmissible from one generation to the next, just as seed-borne virus infections are transmitted from one generation to the next.

Following are examples which illustrate procedures for practicing the invention. These examples should not be construed as limiting. All percentages are by weight and all solvent mixture proportions are by volume unless otherwise noted.

Example 1—Construction of *Agrobacterium* Vectors

Binary vectors for expressing the BMV 1a and 2a proteins in plants were constructed. Starting with the pBI101.2 construct (Clontech, Palo Alto, Calif.), the GUS gene was removed by first cutting the construct with EcoRI and SnaBI. The overhanging restriction fragment ends were filled in by treatment with Klenow fragments and dNTPs. The restriction fragment ends were religated forming the pB101.2LR1.

Figure 1:
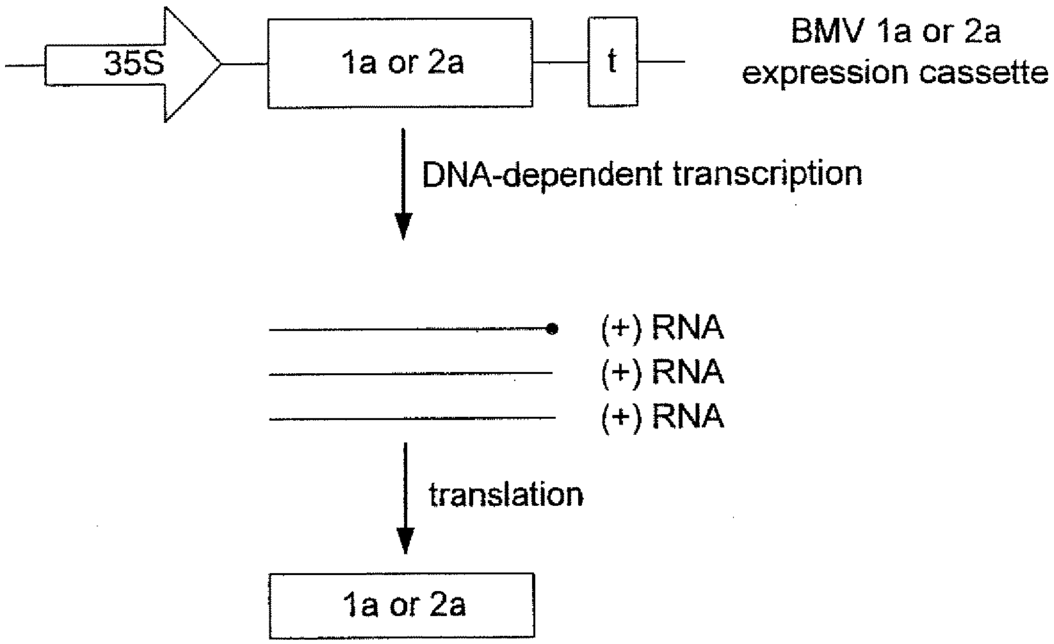
FIG. 1 represents the schematic for producing the 1a and 2a proteins in the host cell.
Figure 2:
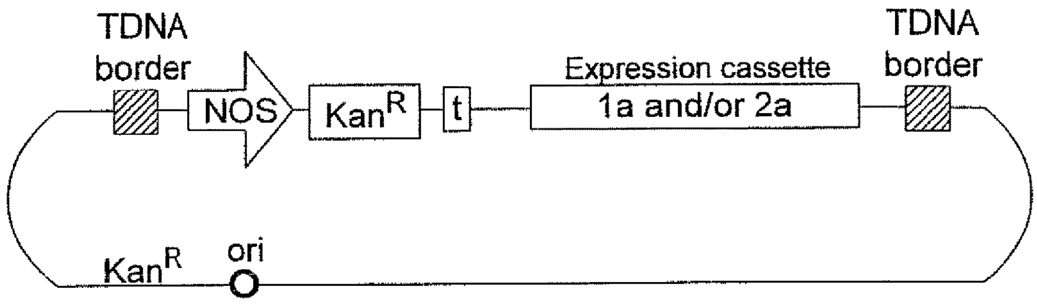
FIG. 2 illustrates an example of an *Agrobacterium* transformation vector containing an expression cassette capable of expressing 1a and/or 2a BMV proteins.
Figure 3A:
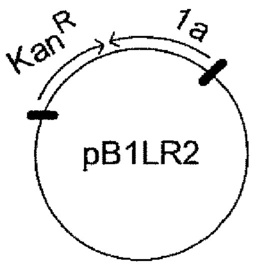
FIG. 3 illustrates several *Agrobacterium* vectors that were produced to transform host plant cells (black rectangles indicate T-DNA borders).
Figure 3B:
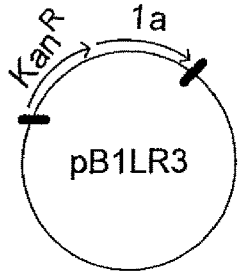
Figure 3C:
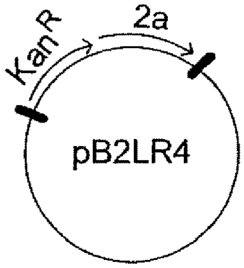
Figure 3D:
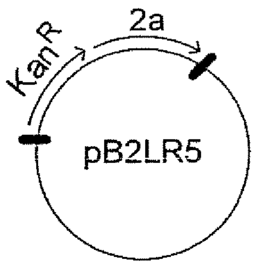
Figure 3E:
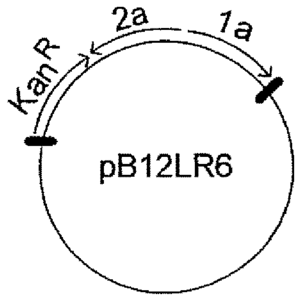
Figure 3F:
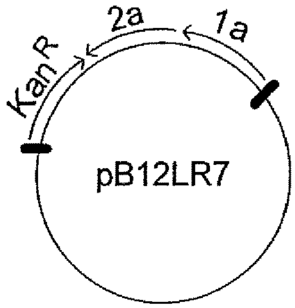
Figure 3G:
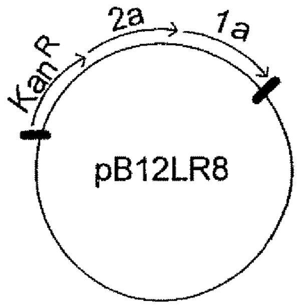
Figure 3H:
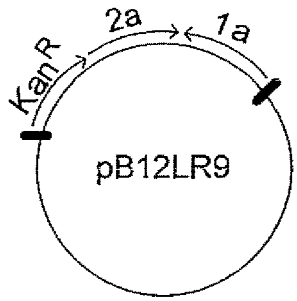

The 2a expression cassette was inserted into pBI101.2 LR1. First the pBI101.2LR1 was cut with Hind III and dephosphorylated. Next, pB2PA17 (Dinant et al., 1993) was cut with Hind III and the 2a insert was purified using a low melting agarose gel. The restriction fragment ends were ligated forming the pB2LR4 and pB2LR5 (FIGS. 3*c* and 3*d*).

The 1a expression cassette was inserted into pBI101.2LR1 by first cutting pBI101.2LR1 with SnaBI and dephosphorylated. pB1PA17 (Dinant et al., 1993) was cut with PstI and the extra nucleotides were removed with T4 DNA polymerase. The 1a insert was purified using a low melting agarose gel. The restriction fragment ends were ligated forming the pB1LR2 and pB1LR3 vectors (FIGS. 3*a* and 3*b*).

The 1a expression cassette was inserted into pB2LR4 and pB2LR5 by cutting pB2LR4 or pB2LR5 with SnaBI and dephosphorylated. PB1PA17 (Dinant et al., 1993) was cut with PstI, and the extra nucleotides were removed with T4 DNA polymerase. The 1a insert was purified using low melting agarose gel and ligated with the cut pB2LR4 or pB2LR5 vectors to form pB12LR6, pB12LR7, pB12LR8, and pB12LR9 vectors (FIGS. 3*e*-3*h*).

Figure 4:
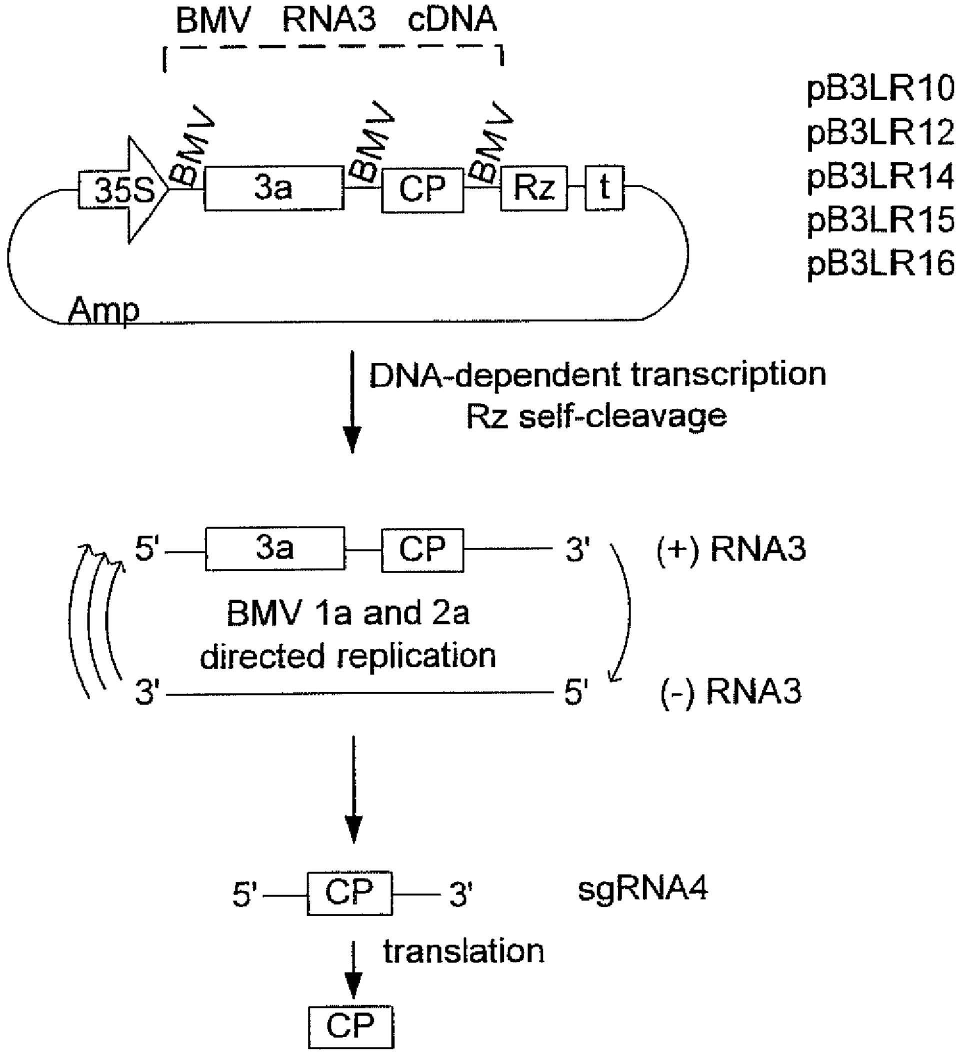
FIG. 4 represents the general mechanism of BMV RNA3 launching, and replication.

Example 2—Construction of DNA-Launching Platform for wtRNA3 of BMV and for RNA Derivatives Containing Foreign Sequences Vector pRT101 (Töpfer et al., 1987) was cut with PpuMI and the restriction fragment ends were filled in with Klenow fragment and dNTPs, and cut with BamHI and dephosphorylated. Vector pB3RQ39 (Ishikawa et al., 1997) was cut with SnaBI and BamHI; the B3 fragment was isolated from a low melting agarose gel. This fragment was ligated to the cut pRT101 thereby forming pB3LR10 (FIG. 4). The pB3LR15 (FIG. 4) that is a pB3LR10 derivative has the ClaI-KpnI fragment replaced with the corresponding fragment from pB3TP8 (Janda et al., 1987).

PCR was performed on pRT101 to amplify an EcoRV and EcoRI fragment. To create a StuI site instead of a PpuMI site, a one nucleotide deletion was performed during the PCR process. The resulting PCR product was cut with EcoRV and EcoRI and inserted into dephosphorylated pRT101 cut with EcoRV and EcoRI to form pRT101LR11. The pRT101LR11 was cut with StuI and BamHI and dephosphorylated. PB3RQ39 was cut with SnaBI and BamHI and a B3 fragment was isolated using a low melting agarose gel. The fragment was then ligated to pRT101LR11 to form pB3LR12 (FIG. 4).

Another DNA-launching platform was constructed with wtRNA3 of BMV having a partially doubled CaMV35S promoter; thereby forming pB3LR14 and pB3LR16 (FIG. 4).

A DNA-launching platform wherein the BMV RNA3 coat protein was replaced with GUS was also constructed. The pB3MI22 (Ishikawa et al., 1997) was cut with ClaI and StuI and a B3GUS insert was isolated. The pB3LR10 or pB3LR14 DNA-launching constructs were cut with ClaI and StuI and dephosphorylated. The B3GUS fragment was then ligated to the cut pB3LR10 or pB3LR14 thereby forming the pB3GUSLR17 and pB3GUSLR18 DNA-launching constructs (FIG. 5).

A DNA-launching platform having a BMV RNA3 with a GUS gene insertion wherein the GUS is downstream of an additional BMV subgenomic promoter was constructed. The pB3LR15 construct was cut with AvaI and the restriction fragment ends were filled in with Klenow fragment and dNTPs. Construct was then cut with ClaI and dephosphorylated. The pB3MI22 was cut with ClaI and StuI and a B3GUS fragment was isolated. The isolated B3GUS fragment was then ligated to the cut pB3LR15 construct to form a new construct of pB3GUSCPLR19 (FIG. 5).

A BMV RNA3 based DNA-launching platform with a CP gene inserted downstream of an additional cowpea chlorotic mottle virus (CCMV) subgenomic promoter was constructed. The pB3GUSLR17 construct was cut with StuI and KpnI and dephosphorylated. The pBC3AJ14 (Pacha and Ahlquist, 1991) was cut with NdeI, the ends were blunted by known methods in the art, and then cut with KpnI. A coat protein fragment was then isolated. The coat protein fragment was then ligated to the cut pB3GUSLR17 to form a new construct of pB3GUSCPLR22 (FIG. 5).

Figure 5A:
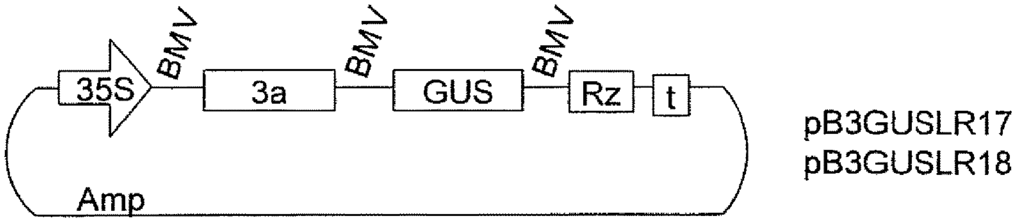
FIG. 5 depicts DNA-launching platforms which can be used in accord with the teachings contained herein. The BMV and CCMV designations denote cis-acting elements.
Figure 5B:
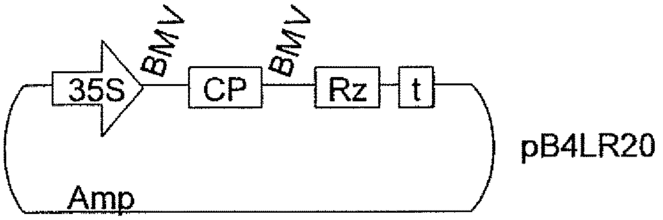
Figure 5C:
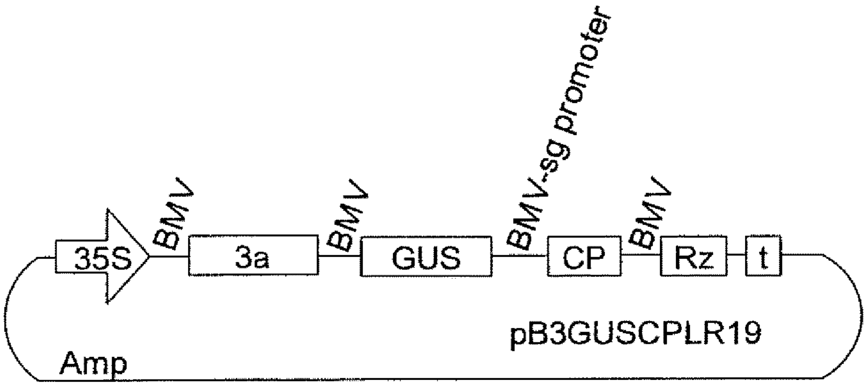
Figure 5D:
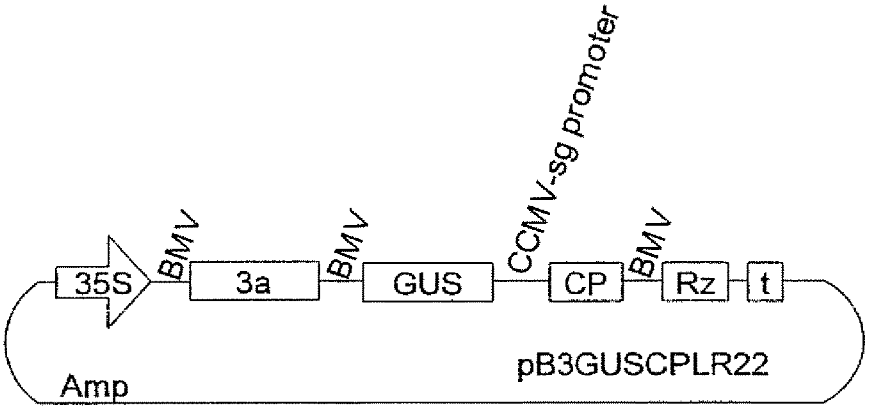

A DNA-launching platform was constructed having a subgenomic RNA4. The pB4MK2 (M. Kroll, personal communications) was cut with SnaBI and BamHI and a RNA4 fragment was then isolated. The pRT101LR11 construct was cut with StuI and BamHI and dephosphorylated. The fragment and the cut pRT101LR11 construct were then ligated forming pB4LR20 (FIG. 5*a*).

Figure 6A:
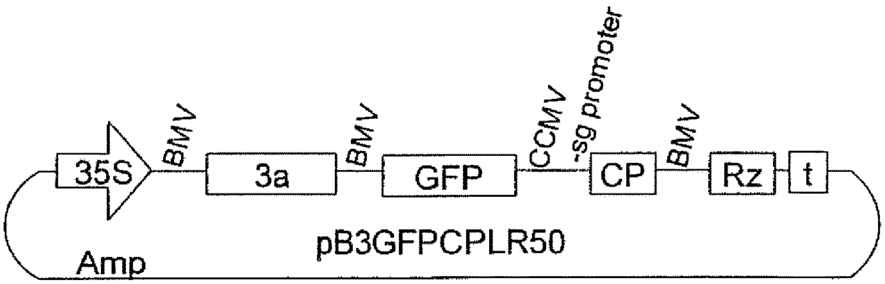
FIG. 6 depicts DNA-launching platforms which can be used in accord with the teachings contained herein.
Figure 6B:
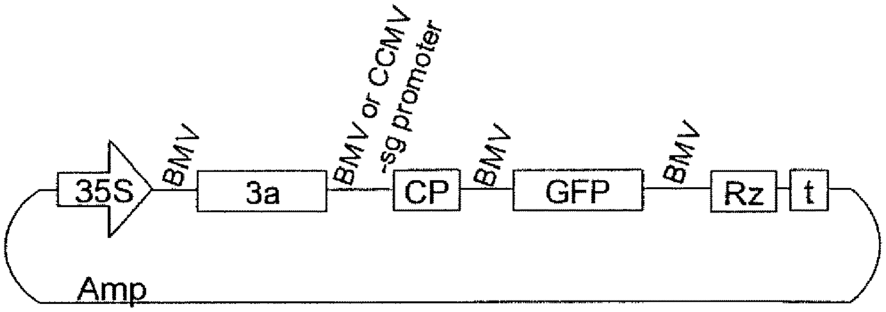
Figure 6C:
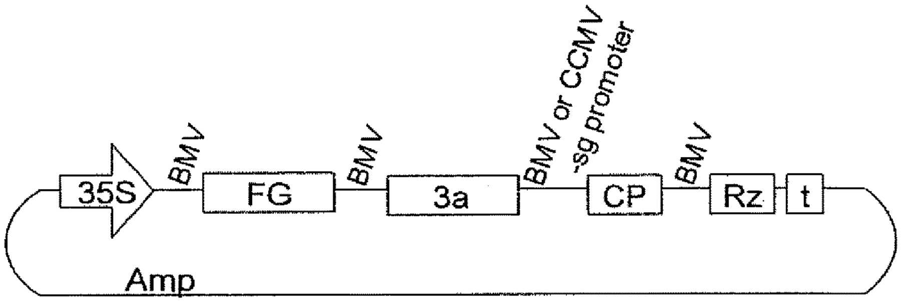
Figure 6D:
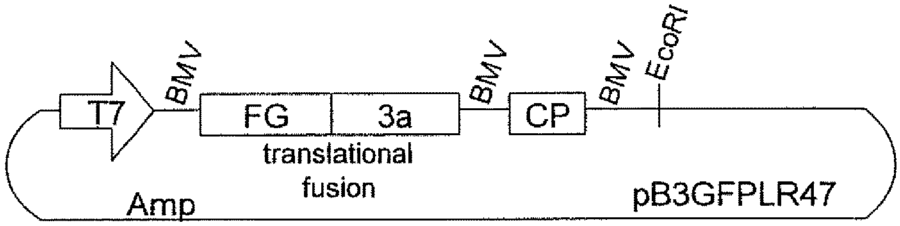
Figure 6E:
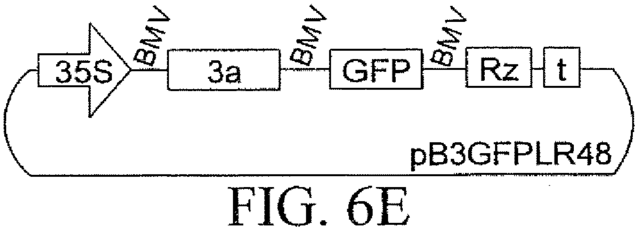

A DNA-launching platform wherein the BMV coat protein was replaced with GFP was constructed. pEGFP (Clontech, CA) was cut with NotI, filled in with Klenow fragment and dNTPs, cut with SalI, and GFP insert was isolated using low-melting agarose gel. The pB3LR15 was cut with SalI and StuI and dephosphorylated. The GFP fragment was then ligated to the cut pB3LR15 thereby forming the pB3GFPLR48 (FIG. 6*e*).

A DNA-launching platform having a BMV RNA3 with a GFP gene insertion wherein the CP is downstream of an additional CCMV subgenomic promoter was constructed. The pBC3AJ14 (Pacha and Ahlquist, 1991) was cut with NdeI and EcoRI and the ends were blunted by known methods in the art. The coat protein fragment was then isolated and ligated into dephosphorylated and blunted pEGFP cut with NotI and StuI forming pEGFPCPLR49. pEGFPCPLR49 was cut with KpnI and the EGFPCP fragment was isolated using low-melting agarose gel. PB3GFPLR48 was cut with KpnI and dephosphorylated. The EGFPCP fragment was then ligated to the cut pB3GFPLR48 thereby forming the pB3GFPCPLR50 (FIG. 6*a*).

An RNA transcription vector wherein the GFP gene is expressed as a translational fusion with BMV 3a was constructed. The pB3TP10 (Pacha and Ahlquist, 1991) was cut with BamHI and dephosphorylated. The GFP fragment was amplified from pEGFP (Clontech, CA) using PCR and the following primers:

```
(SEQ ID NO. 9:)
5'GCAGTCGACGGTACCGCGGGCC3'
and

(SEQ ID NO. 10:)
5'CGCGGCCGCGGATCCTGTACAGCTCG3'.
```

The amplified product was cut with BamHI and purified using low-melting agarose gel. The GFP fragment was ligated to the cut pB3TP10 forming pB3GFPLR47 (FIG. 6*d*). The pB3GFPLR47 was cut with EcoRI and transcribed using T7 RNA polymerase.

Figure 9:
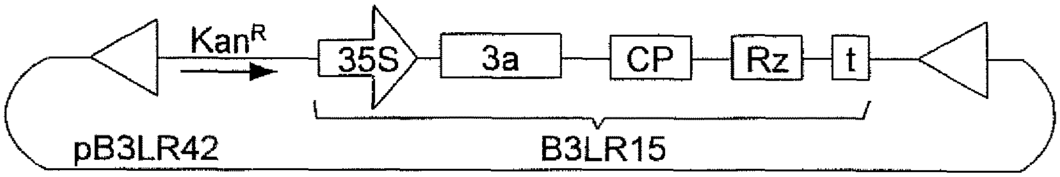
FIG. 9 depicts *Agrobacterium* vector for delivery of DNA-launching platforms to plant cells (open triangles represent T-DNA borders).

An *Agrobacterium* vector containing BMV RNA3 DNA-launching platform was constructed. The pBI101.2LR1 was cut with SmaI and dephosphorylated. The pB3LR15 was cut with PvuII and the B3 fragment was purified using a low-melting agarose gel. The B3 fragment was then ligated to the cut pBI101.2LR1 thereby forming pB3LR42 (FIG. 9).

Figure 7A:
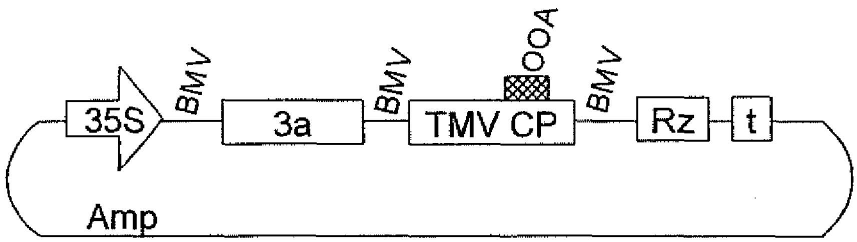
FIG. 7 depicts DNA-launching platforms which can be used in accord with the teachings contained herein.

A DNA-launching platform wherein the BMV RNA3 coat protein was replaced with the SHMV (Sunn hemp mosaic virus) coat protein and the GUS gene was inserted downstream of an additional BMV subgenomic promoter was constructed. The pB3RS4 (Sacher et al. 1988) was cut with AvaI, blunted with Klenow fragment and dNTPs, and cut with KpnI. The SHMV coat protein fragment was isolated using a low-melting agarose gel. The pB3GUSLR17 was cut with StuI and KpnI and dephosphorylated. The SHMV coat protein fragment was ligated to the cut pB3GUSLR17 thereby forming pB3GUSCPLR24 (FIG. 7).

Other permutations of DNA-launching platforms containing one or more foreign genes and the necessary cis-acting replication signals will be readily appreciated in view of the teachings herein. For examples, see FIGS. 5-10.

Example 3—Transfection of *N. tabacum* Protoplasts with DNA-Launching Platform Media:

NT1 Medium (1 liter) was made with Gibco-BRL (MS salt, catalog #11118-031), 3 ml of 6% KH2PO4, and 0.2 μg/ml 2,4D (final concentration). The pH was adjusted to 5.5-5.7 using KOH, and the resulting mixture was autoclaved.

NT1 Plating Medium (1 liter) was made with NT1 medium and 72.86 g mannitol, the pH was adjusted to 5.5-5.7, and the resulting mixture was autoclaved.

Wash Solution (1 liter) was made with 72.86 g mannitol, the pH was adjusted to 5.5, and the resulting mixture was autoclaved.

Electroporation Buffer was made with 0.8% NaCl, 0.02% KCl, 0.02% KH2PO4, 0.11% Na2HPO4, and 0.4M mannitol. The pH was adjusted to 6.5, and the resulting mixture was autoclaved.

Enzyme Solution was made with 0.4M mannitol, and 20 mM MES. The pH was adjusted to 5.5, and the resulting mixture was autoclaved.

Growth Conditions:

Cells (*Nicotiana tabacum*) were grown at room temperature in NT1 media with constant shaking (about 200 rpm).

Preparation of Cultures for Digestion:

About 2-3 ml of one-week old suspension culture was subcultured into 50 ml of fresh NT1 media 3 days before the enzyme digestion. The culture was maintained at 28° C. under constant shaking.

Enzyme Digestion:

The enzyme digestion solution was prepared containing the following: 1% cellulysin (Calbiochem) and 0.3% macerase (Calbiochem) in the enzyme solution. The pH was adjusted to 5.5 and filter sterilized.

The cells were centrifuged at 800 rpm for 5 min. The supernatant was discarded. About 40 ml of wash solution was added, cells were resuspended and were centrifuged at 800 rpm for 5 min. The supernatant was discarded. The cells were then resuspended in three volumes of enzyme digestion solution, and incubated for 60 min. at room temperature.

Washing:

The cells were transferred into 50 ml plastic tube and centrifuged at 800 rpm for 5 min. The supernatant was discarded. The cells were resuspended in 40 ml of wash solution and centrifuged at 800 rpm for 5 min. The supernatant was discarded. The cells were resuspended in 40 ml of electroporation buffer and centrifuged at 800 rpm for 5 min. The supernatant was discarded. The cells were resuspended in four volumes of electroporation buffer.

Electroporation:

One ml of cells containing the RNA or DNA inocula was transferred into electroporation cuvettes and placed on ice for 10 min. The cells were then mixed and electroporated at 500 microF, 250V. The cuvettes were placed on ice for 10 min. The cells were transferred into 10 ml of NT1 plating media.

Incubation and Collection of Samples:

The cells were incubated at room temperature in dark. Samples were collected 24-48 hrs post inoculation.

RNA Analysis.

RNA extraction, denaturing 1% agarose gel electrophoresis and Northern blot hybridization were performed by known methods, such as that performed in Rasochova and Miller (1996). Each lane was loaded with equal amounts (approx. 5 μg) of total RNA as determined by spectrophotometry and confirmed by ethidium bromide staining of ribosomal RNA before Northern blot hybridization. $1\times10^6$ cpm/ml of radioactive probe in hybridization buffer was used per hybridization experiment. Replication of RNA3 was confirmed by detection of sgRNA4, thus showing that BMV RNA replication factors 1a and 2a expressed from expression plasmid(s) support efficient replication of RNA3 supplied as in vitro transcript (FIG. 11) as well as launched from DNA-launching platform (FIG. 12).

Example 4—Production of Transgenic *N. tabacum* Plants

Once a desired molecule was constructed in *E. coli*, the molecule was transferred into *Agrobacterium tumefaciens* by the freeze-thaw method. Vectors pB1LR2, pB2LR4, pB12LR6, and pB12LR7 were all individually used. An *Agrobacterium* strain LBA 4404 containing an appropriate helper Ti plasmid was grown in 5 ml of YEP medium overnight at 28° C. Two ml of the overnight culture were added to 50 ml YEP medium in a 250-ml flask and shaken vigorously (250 rpm) at 28° C. until the culture grew to an $OD_{500}$ of 0.5 to 1.0. The culture was chilled on ice. The cell suspension was centrifuged at 3000 g for 5 min. at 4° C. The supernatant solution was discarded. The cells were resuspended in 1 ml of ice-cold 20 mM $CaCl_2$ solution. 0.1-ml aliquots were dispensed into prechilled eppendorf tubes. About 1 μg of plasmid DNA was added to the cells. The cells were frozen in liquid nitrogen. The cells were thawed by incubating the test tube in a 37° C. water bath for 5 min. 1 ml of YEP medium was added to the tube and incubated at 28° C. for 2-4 h with gentle shaking to allow the bacteria to express the antibiotic resistance genes. The tubes were centrifuged for 30 s and the supernatant solution was discarded. The cells were resuspended in 0.1 ml YEP medium, plated on a YEP agar plate containing selection antibiotic(s), and incubated at 28° C. Transformed colonies appeared in 2-3 days.

In vitro clonal copies of approximately three week old *Nicotina tabacum*, Wisconsin No. 38, were used as the source of explants. Leaf explants were prepared from the second and third fully expanded leaves of in vitro cultures. The leaf pieces were cut into 1 cm×1 cm squares and placed upon TB1 (plus 2.0 mg/l 6-benzyl-aminopurine, and 0.1 mg/1-naphthalene acetic acid) media for 24 hours at 25° C. with a 16 hour photo period.

*Agrobacterium tumefaciens* strain LBA 4404 containing the preselected binary vector was used for plant transformation. Explants were placed in ~10 ml of overnight grown *Agrobacterium* culture for 30 min. Leaf explants were then blotted on filter paper and placed on TB2 (plus 1.0 mg/l 6-benzyl-aminopurine and 0.1 mg/1-naphthalene acetic acid) media for 4 days, abaxial side down. Explants are then rinsed three times in sterile water, blotted on filter paper, and placed on TB2 media for regeneration with 100 mg/l kanamycin and 400 mg/l carbenicillin at 25° C., 16 hour photo period, abaxial side down. Explants were transferred to fresh TB2 media with 100 mg/l kanamycin and 400 mg/l carbenicillin every 10 to 14 days until plantlets developed. Plantlets typically developed at 10-14 days. Plantlets were cut from the callus and placed on MST media containing 100 mg/l kanamycin and 400 mg/l carbenicillin to induce rooting. Rooted plants were transferred to soil.

TB1 (1 liter) included 4.30 g MS salts, 100 mg myo-inositol, 1.0 ml Nitsch and Nitsch vitamins, 30 g sucrose, 2 mg BAP 0.10 mg of NAA, and 8 g Noble agar. The media was adjusted to a pH 5.7 and autoclaved.

TB2 (1 liter) included 4.30 g MS salts, 100 mg myo-inositol, 1.0 ml Nitsch and Nitsch vitamins, 30 g sucrose, 1.0 mg BAP, 0.10 mg NAA, and 8 g Noble agar. The media was adjusted to pH 5.7 and autoclaved.

MST (1 liter) included 4.30 g MS salts, 1.0 ml Nitsch and Nitsch vitamins, 30 g sucrose, 100 mg myo-inositol, and 8.5 g Difco agar. The media was adjusted to pH 5.7 and autoclaved.

YEP (100 ml) included 1.0 g Bacto-peptone, 1.0 g Bacto-yeast extract, and 0.5 g NaCl. The media was autoclaved.

Figures 13A, 13B, 13C:
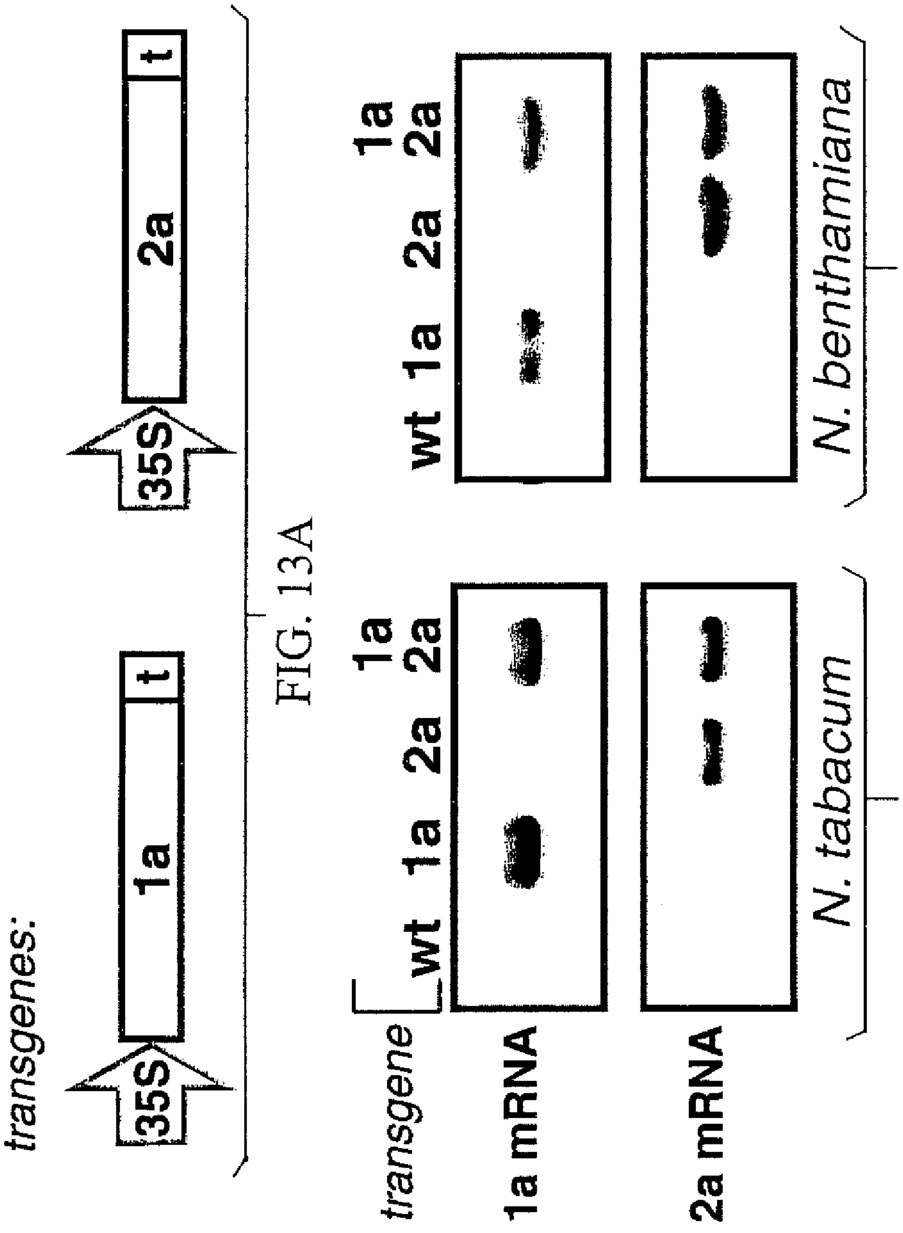

RNA Analysis:

Total RNA extraction, denaturing 1% agarose gel electrophoresis and Northern blot hybridization was performed by known methods, such as that performed in Rasochova and Miller (1996). Each lane was loaded with equal amounts (approx. 5 μg) of total RNA as determined by spectrophotometry and confirmed by ethidium bromide staining of ribosomal RNA before Northern blot hybridization. $1\times10^6$ cpm/ml of radioactive probe in hybridization buffer was used per hybridization experiment. FIG. 13*a* shows the successful expression of BMV 1a and 2a mRNA in transgenic *N. tabacum.*

Example 5—Transfection of Transgenic *N. tabacum* Plants with DNA-Launching Platform Precipitation of DNA onto Microcarriers for Particle Bombardment:

(Kikkert, 1993).

Sterilization of Microcarriers:

80 mg of gold microcarriers were resuspended in 1 ml of 70% ethanol, soaked for 15 min., and centrifuged at 13,000×g for 5 min. The supernatant was carefully removed and discarded. Particles were resuspended in 1 ml of sterile distilled, deionized water and centrifuged at 13,000×g for 5 min. The supernatant was carefully removed and discarded. Water washing of particles was repeated 2 more times. After final rinse, particles were resuspended in 1 ml of sterile 50% glycerol.

Coating Microcarriers with DNA:

The following was sequentially and quickly added: 5 μl DNA (1 μg/μl), 50 μl of 2.5M $CaCl_2$, and 20 μl of 0.1M Spermidine.

The mixture was incubated for 10 min. on a vortex shaker at room temperature. Particles were pelleted by centrifugation at 13,000×g for 5 sec. Supernatant was carefully removed and discarded. Particles were resuspended in 140 μl of 70% ethanol and centrifuged at 13,000×g for 5 sec. Supernatant was removed and discarded. Particles were resuspended in 140 μl of 100% ethanol and centrifuged at 13,000×g for 5 sec. Supernatant was removed and discard. Particles were resuspended in 50 μl of 100% ethanol.

Young leaves from tobacco plants grown in vitro on agar-solidified MS medium containing 30 g/liter sucrose, were bombarded with 5-μl aliquots of resuspended DNA-coated particles using a PDS1000He biolistic gun (DuPont) and 1100 psi rupture disks (Bio-Rad).

RNA Analysis:

Total RNA extraction, denaturing 1% agarose gel electrophoresis and Northern blot hybridization was performed by known methods, such as that performed in Rasochova and Miller (1996). Each lane was loaded with equal amounts (approx. 5 μg) of total RNA as determined by spectrophotometry and confirmed by ethidium bromide staining of ribosomal RNA before Northern blot hybridization. $1\times10^6$ cpm/ml of radioactive probe in hybridization buffer was used per hybridization experiment. FIG. 14*a* shows that the launched BMV RNA3 replicates efficiently in transgenic plants expressing BMV replication factors 1a and 2a and that the launched RNA3 is unable to replicate in the absence of BMV 1a and/or 2a.

Example 6—Production of Transgenic *N. benthamiana* Plants

Once a desired molecule was constructed in *E. coli*, the molecule was transferred into *Agrobacterium tumefaciens*. Vectors pB1LR2, pB2LR4, pB12LR6, and pB12LR7 were all individually used. An *Agrobacterium* strain LBA 4404 containing an appropriate helper Ti plasmid was grown in 5 ml of YEP medium overnight at 28° C. Two ml of the overnight culture were added to 50 ml YEP medium in a 250-ml flask and shaken vigorously (250 rpm) at 28° C. until the culture grew to an $OD_{500}$ of 0.5 to 1.0. The culture was chilled on ice. The cell suspension was centrifuged at 3000 g for 5 min. at 4° C. The supernatant solution was discarded. The cells were resuspended in 1 ml of ice-cold 20 mM $CaCl_2$ solution. 0.1-ml aliquots were dispensed into prechilled eppendorf tubes. About 1 μg of plasmid DNA was added to the cells. The cells were frozen in liquid nitrogen. The cells were thawed by incubating the test tube in a 37° C. water bath for 5 min. 1 ml of YEP medium was added to the tube and incubated at 28° C. for 2-4 h with gentle shaking to allow the bacteria to express the antibiotic resistance genes. The tubes were centrifuged for 30 s and the supernatant solution was discarded. The cells were resuspended in 0.1 ml YEP medium. The cells were plated on a YEP agar plate containing selection antibiotic(s) and incubated at 28° C. Transformed colonies appeared in 2-3 days.

In vitro clonal copies of approximately five-seven weeks old *N. benthamiana* were used as the source of explants. Leaf explants were prepared from the second and third fully expanded leaves of in vitro cultures. The leaf pieces were cut into 1 cm×1 cm squares and placed upon MS104 media in 100×15 mm plates for 24 hours at 23° C. with a 16 hour photo period.

*Agrobacterium tumefaciens* is strain LBA 4404 containing the preselected binary vector was used. Explants were placed in ~10 ml of overnight grown *Agrobacterium* culture for 30 min. Leaf explants were then blotted on filter paper and placed abaxial side down on MS104 media for 4 days. Explants were then rinsed three times in sterile water, blotted on filter paper, and placed on MS104 media for regeneration with 300 mg/L kanamycin and 400 mg/L carbenicillin. Explants were transferred to fresh MS104 media with 300 mg/L kanamycin and 400 mg/L carbenicillin every 10-14 days until plantlets developed. Plantlets typically developed at 31-50 days. Plantlets were cut from the callus and placed on MST media plus 300 mg/L kanamycin and 400 mg/L carbenicillin to induce rooting. Rooted plants were transferred to soil.

One liter of MS104 included 4.3 g MS salt mixture, 1.0 ml B5 vitamin solution, 30 g sucrose, 1.0 mg BA, 0.1 mg NAA, and 8.0 g Phytagar. The media was adjusted to pH 5.8 and autoclaved.

100 ml of YEP included 1.0 g Bacto-peptone, 1.0 g Bacto-yeast extract, 0.5 g NaCl. The media was autoclaved.

One liter of MST included 4.3 g MS salt mixture, 1.0 ml Nitsch & Nitsch vitamins, 30 g sucrose, 100 mg myo-inositol, and 8.5 g Phytagar. The media was adjusted to pH 5.7 and autoclaved.

RNA Analysis:

Total RNA extraction, denaturing 1% agarose gel electrophoresis and Northern blot hybridization was performed by known methods, such as that performed in Rasochova and Miller (1996). Each lane was loaded with equal amounts (approx. 5 μg) of total RNA as determined by spectrophotometry and confirmed by ethidium bromide staining of ribosomal RNA before Northern blot hybridization. $1\times10^6$ cpm/ml of radioactive probe in hybridization buffer was used per hybridization experiment. FIG. 13*b* shows the successful expression of BMV 1a and 2a mRNA in transgenic *N. benthamiana.*

Example 7—Transfection of Transgenic *N. benthamiana* Plants

Precipitation of DNA onto Microcarriers for Particle Bombardment:

(Kikkert, 1993).

Sterilization of Microcarriers:

80 mg of gold microcarriers were resuspended in 1 ml of 70% ethanol, soaked for 15 min., and centrifuged at 13,000×g for 5 min. The supernatant was carefully removed and discarded. Particles were resuspended in 1 ml of sterile distilled, deionized water and centrifuged at 13,000×g for 5 min. The supernatant was carefully removed and discarded. Water washing of particles was repeated 2 more times. After final rinse, particles were resuspended in 1 ml of sterile 50% glycerol.

Coating Microcarriers with DNA:

To the 50 μl of particles the following was sequentially and quickly added: 5 μl DNA (1 μg/μl), 50 μl of 2.5M $CaCl_2$, and 20 μl of 0.1M Spermidine.

The mixture was incubated for 10 min. on a vortex shaker at room temperature. Particles were pelleted by centrifugation at 13,000×g for 5 sec. Supernatant was carefully removed and discarded. Particles were resuspended in 140 μl of 70% ethanol and centrifuged at 13,000×g for 5 sec. Supernatant was removed and discarded. Particles were resuspended in 140 μl of 100% ethanol and centrifuged at 13,000×g for 5 sec. Supernatant was removed and discarded. Particles were resuspended in 50 μl of 100% ethanol.

Young leaves from *N. benthamiana* plants grown in vitro on agar-solidified MS medium containing 30 g/liter sucrose, were bombarded with 5-μl aliquots of resuspended DNA-coated particles using a PDS1000He biolistic gun. (DuPont) and 1100 psi rupture disks (Bio-Rad).

RNA Analysis:

Total RNA extraction, denaturing 1% agarose gel electrophoresis and Northern blot hybridization was performed by known methods, such as that performed in Rasochova and Miller (1996). Each lane was loaded with equal amounts (approx. 5 μg) of total RNA as determined by spectrophotometry and confirmed by ethidium bromide staining of ribosomal RNA before Northern blot hybridization. $1\times10^6$ cpm/ml of radioactive probe in hybridization buffer was used per hybridization experiment. The launched BMV and RNA 3 showed efficient replication (FIG. 14*b*) in transgenic *N. benthamiana* plants expressing BMV replication factors 1a and 2a and was unable to replicate in the absence of BMV 1a and/or 2a.

Example 8—Transfection of Transgenic Plants with GUS Containing DNA-Launching Platform Transgenic *N. tabacum* and *N. benthamiana* plants were produced according to the procedures discussed above. The plants were transfected with a DNA-launching platform containing a GUS gene (FIG. 5*a*) by particle bombardment as described in Examples 5 and 7. The plants were incubated for 3-5 days and then assayed for β-glucuronidase (GUS) activity using 1 mg/ml X-Gluc (5-bromo-4-chloro-3-indolyl glucucuronide) as substrate in 0.1M potassium phosphate buffer, pH 7.0, 50 μM potassium ferrocyanide, and 2% Triton□ X-100. Following an overnight incubation at 37° C., cells replicating launched RNA3 derivatives and expressing the GUS reporter gene from a subgenomic RNA4 gave rise to blue spots (FIG. 15). The launched RNA3 derivative did not replicate and express GUS reporter gene in the absence of BMV RNA replication factors 1a and 2a (e.g., in wt *N. benthamiana* and in wt *N. tabacum*).

Figure 10A:
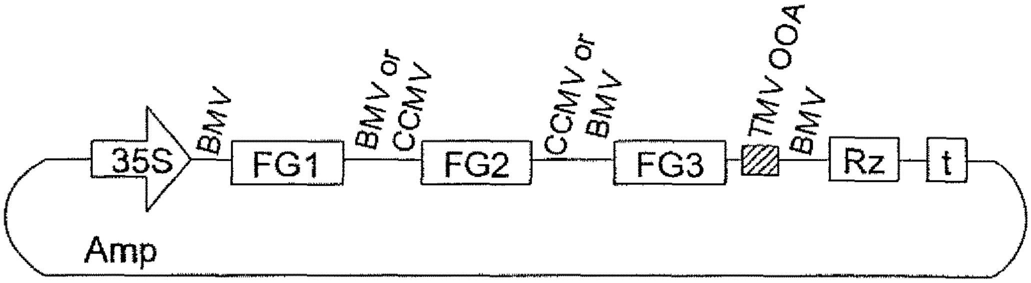
FIG. 10 depicts DNA-launching platforms which can be used in accord with the teachings contained herein.
Figure 10B:
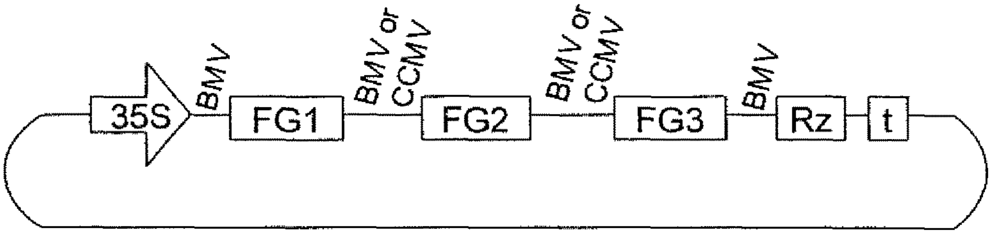
Figure 10C:
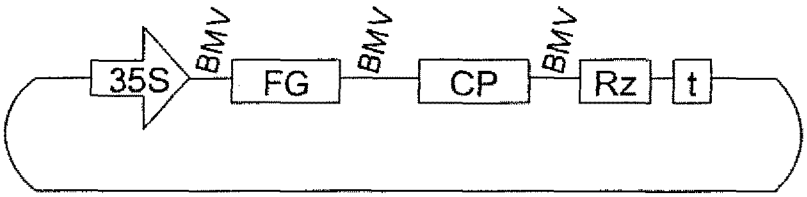

Example 9—Transfection of Transgenic Plants Expressing BMV 1a, 2a, 3a, and CP A plant is transformed with BMV 1a, 2a, 3a, and CP genes whereby those genes are stably expressed in said plant. This can be done with the procedures outlined above. Any modifications that would be needed would be readily apparent to those skilled in the art in light of the teachings contained herein. A DNA-launching platform encoding an RNA replicon which contains a foreign gene and necessary BMV or CCMV cis-acting replication signals to replicate said replicon is constructed (FIG. 10*b*). Foreign genes to be included in said replicon could include, for example, a *Bacillus thuringiensis* polynucleotide that codes for a B.t. protein. Other sequences would include, e.g., sequences that encode herbicide resistance, or any other known sequence that encodes peptides or proteins having desired qualities in plants.

Figure 7B:
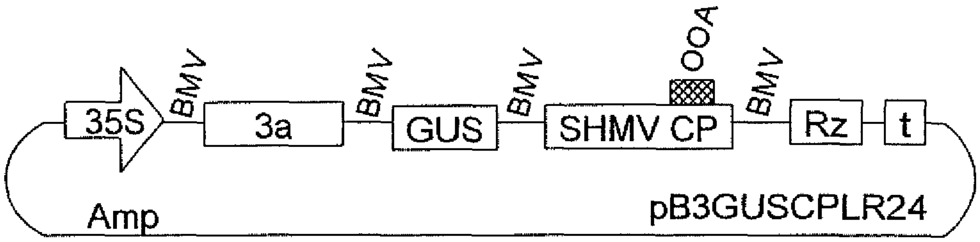
Figure 7C:
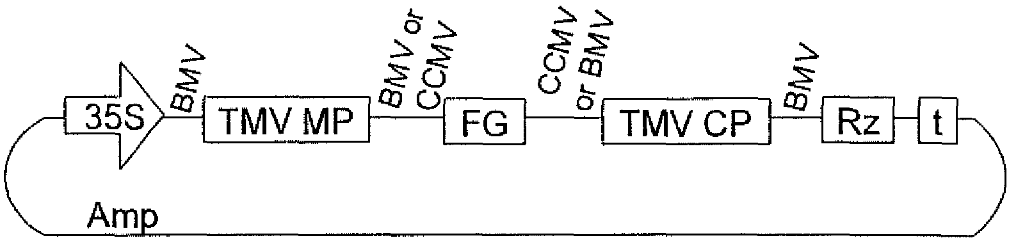
Figure 8A:
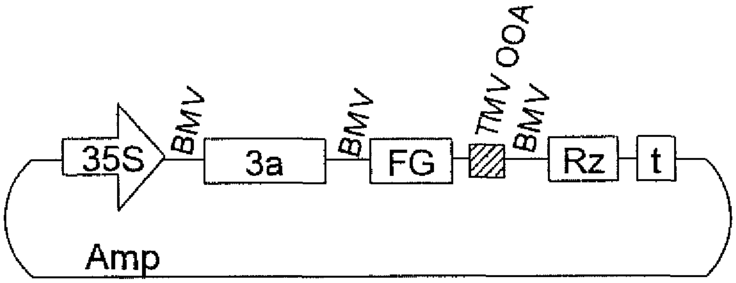
FIG. 8 depicts DNA-launching platforms which can be used in accord with the teachings contained herein.
Figure 8B:
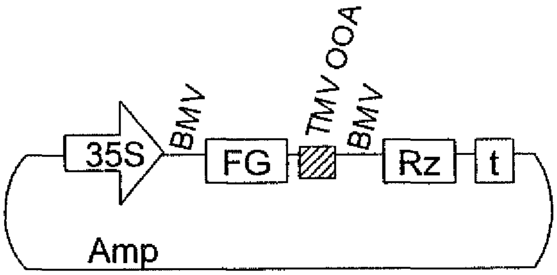
Figure 8C:
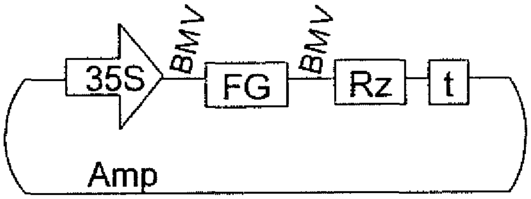

Alternatively, plants can be transformed to express BMV 1a, 2a, 3a, and a TMV coat protein in place of the BMV coat protein. A DNA-launching platform is then made containing one or more foreign genes and the necessary cis-acting replication signals, either BMV or CCMV, and a TMV origin of assembly (FIGS. 8*a*, 8*b*, and 10*a*). This launching platform provides a distinct advantage as TMV is a rod-shaped virus which has no strict limit on the size of RNA that can be encapsidated. Alternatively, TMV movement protein can be used in place of BMV3a (FIG. 7*c*). Hybrids between tobarmo and bromoviruses were shown to be viable (Sacher et al., 1988; De Jong and Ahlquist, 1992).

Other permutations and combinations of genes pretransformed and those included in the DNA-launching platform will readily be appreciated by the skilled artisan in light of the teachings herein. (See, e.g., FIGS. 8*c*, 10*b*, and 10*c*).

As indicated above, CCMV subgenomic promoter can be substituted for BMV sequences in a desired DNA-launching platform. Because the sequence of CCMV subgenomic promoter differs from the sequence of BMV subgenomic promoter, the probability of recombination that would result in loss of a foreign gene is much lower in a construct having a combination of these two different promoters.

In the above examples, trans-acting components may include, but are not limited to, replication factors, components responsible for cell to cell movement, or components such as the coat protein which may be required for long distance spread, viral proteases responsible for post translational processing, or other known trans-acting functions.

Example 10—Transfection of *N. tabacum* Protoplasts with GUS Containing DNA-Launching Platforms

Figure 16B:
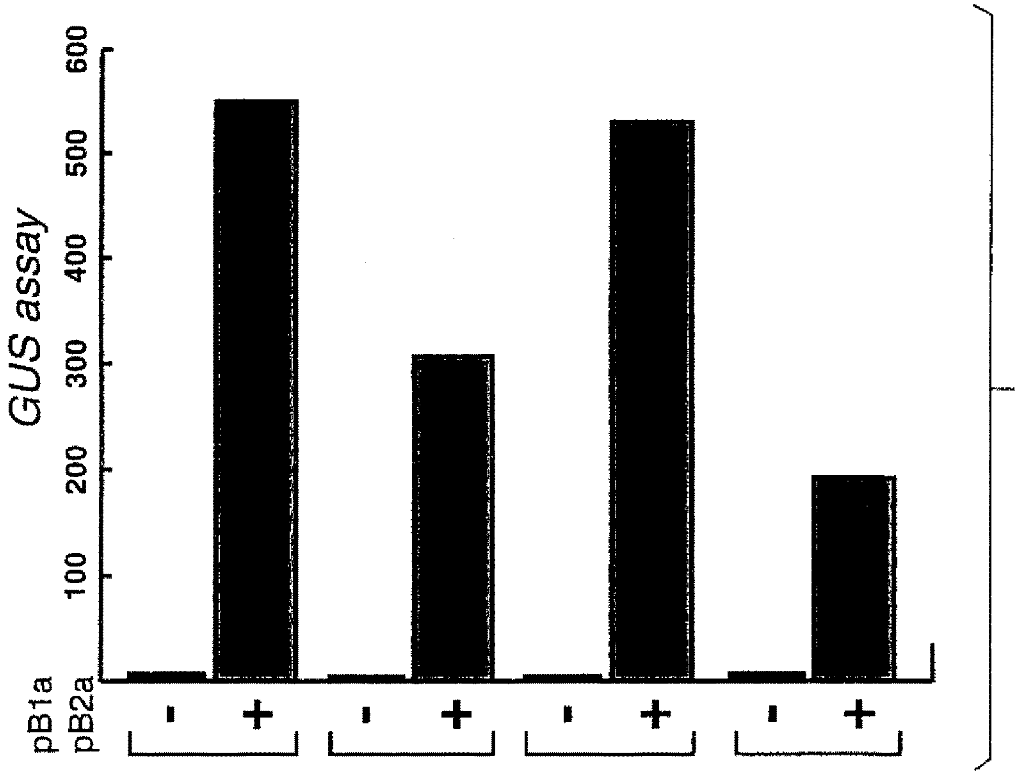
Figure 16A:
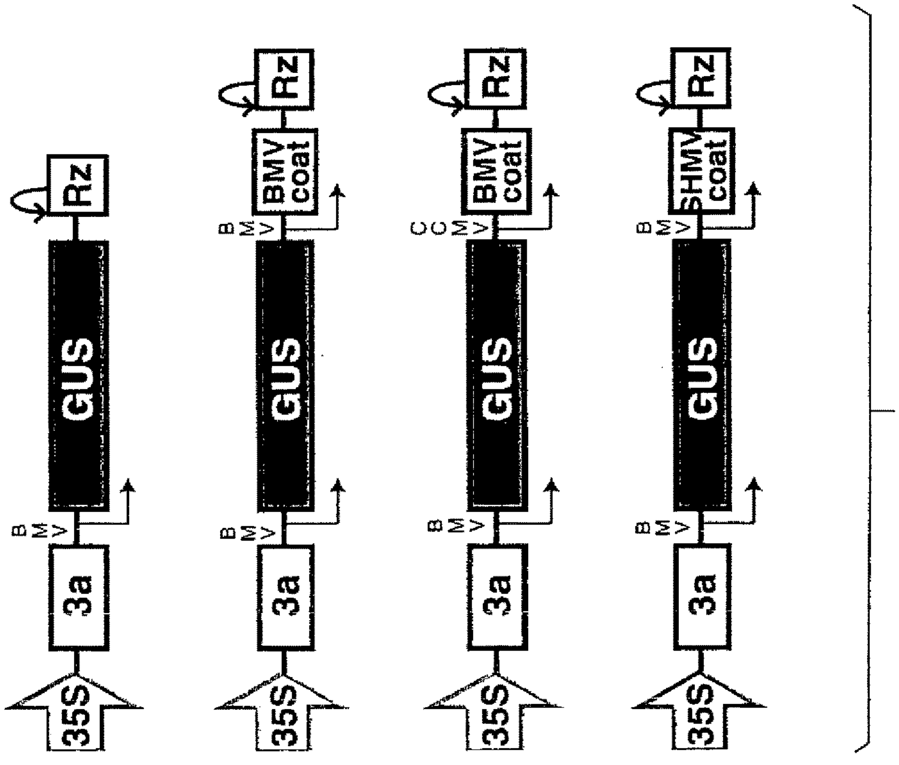

*N. tabacum* protoplasts isolated using the above described methods were inoculated by electroporation with DNA-launching platforms for BMV RNA3 derivatives in the presence or absence of 1a and 2a expression plasmids. BMV RNA3 derivatives contained the GUS gene in place of the coat protein ORF (FIG. 5*a*) (these were inoculated with or without coat protein expression plasmid, FIG. 5*b*), or had the BMVCP gene translated from an additional subgenomic RNA driven from BMV or CCMV subgenomic promoter (FIGS. 5*e* and 5*d*), or had the SHMV coat protein translated from an additional BMV subgenomic RNA (FIG. 7*b*). Protoplasts were collected by centrifugation (800 rpm, 5 min.) 24 hours post inoculation. The chemiluminescent GUS assay was performed using GUS-Light□ (Tropix, Mass.) according to manufacturerd□s instructions. Protein concentrations were determined using the Bio-Rad protein kit (Bio-Rad Laboratories, Hercules, Calif.). The GUS values, determined by luminometer, were adjusted to the same total protein concentration-FIGS. 16*a* and 16*b* show successful GUS expression in protoplasts in the presence of trans-acting BMV replication factors 1a and 2a.

Example 11—Transfection of *N. tabacum* Protoplasts with GFP Containing DNA-Launching Platform

*N. tabacum* protoplasts isolated by using the above described methods were transfected by electroporation with expression plasmids for trans-acting BMV replication factors 1a and 2a and with DNA-launching platforms for RNA3 derivatives having the GFP gene in place of BMV coat protein ORF (FIG. 6*e*), the CP gene translated from an additional subgenomic RNA (FIG. 6*a*) or with an RNA transcript having the GFP expressed as a fusion protein with BMV 3a ORF (FIG. 6*d*). Protoplasts were incubated for 24 hrs and examined for GFP expression using a fluorescent microscope. FIG. 18 shows the successful expression of GFP in protoplasts.

Example 12—Transfection of (1a+2a)-Transgenic Plants with BMV RNA3-Based DNA-Launching Platform Containing GFP

*N. benthamiana* plants were transfected using a particle bombardment as described above with a DNA-launching platform for BMV RNA3 having the GFP gene in place of BMV coat protein (FIG. 6*e*). The GFP expression was determined 24 hrs post inoculation using a fluorescent microscope. FIG. 17 shows the successful expression of GFP in (1a+2a)-transgenic *N. benthamiana.*

Example 13—Transfection of (1a+2a)-Transgenic *N. benthamiana* with BMV RNA3 DNA-Launching Platform Using *Agrobacterium*

*N. benthamiana* plants were inoculated with BMV RNA3 DNA-launching platform using *Agrobacterium tumefaciens*. Once the desired construct (pB3LR42) was obtained in *E. coli* it was transferred to *A. tumefaciens* strain LBA4404 using a thaw-freeze method as described above. The *Agrobacterium* was grown overnight in 28° C. under constant shaking. A single lower leaf of *N. benthamiana* were punctured with a needle multiple times and submerged in *Agrobacterium* culture. The plants were grown at 23° C. with a 16 hr photoperiod. The inoculated leaves were harvested 14 days post-inoculation. The total RNA extraction and northern blot hybridization were performed as described above. FIG. 19 shows replication of launched BMV RNA3 in inoculated (1a+2a)-transgenic *N. benthamiana.*

Example 14—Transfection of (1a+2a)-Transgenic Plants with BMV RNA3-Based DNA-Launching Platform Containing GUS and SHMV Coat Protein

*N. benthamiana* plants were transfected using a particle bombardment as described above with a DNA-launching platform for BMV RNA3 wherein the BMV coat protein was replaced with the SHMV coat protein (Sunn-hemp mosaic virus) and the GUS gene was inserted downstream of an additional BMV subgenomic promoter (FIG. 7*b*). The GUS expression was determined by histochemical GUS assay described above. FIG. 20 shows the successful expression of GUS in (1a+2a)-transgenic plants.

Example 15—Movement of Launched BMV RNA 3

F1 progeny plants from self-fertilized (1a+2a)-transgenic *N. benthamiana* BP14 were inoculated with BMV RNA3 DNA launching platform using *Agrobacterium tumefaciens*. Seedlings were germinated on Smurf media containing Kanamycin. Plants were grown at 23° C. with a 16 hr photoperiod. Once the desired construct (pB3LR42) was obtained in *E. coli* it was transferred to *A. tumefaciens* strain LBA4404 using a thaw-freeze method as described above. The *Agrobacterium* was grown overnight at 28° C. under constant shaking. A single lower leaf of *N. benthamiana* was punctured with a needle multiple times and submerged in *Agrobacterium* culture. The inoculated, middle, and upper leaves were harvested 14 days post-inoculation. Total RNA extraction and northern blot hybridization were performed as described above. RNA3 replication was detected in all leaves tested (FIG. 21). It shows that BMV RNA3 is able to replicate, move cell-to-cell and spread long distance in (1a+2a)-transgenic plants.

Example 16—Transfection of Progeny from (1a+2a)-Transgenic *N. benthamiana* with BMV RNA3 DNA-Launching Platform Progeny plants from self-fertilized (1a+2a)-transgenic *N. benthamiana* (designated BP14) were inoculated with BMV RNA3 DNA-launching platform using *Agrobacterium* as described in Example 13. Control plants (non-transgenic *N. benthamiana*) were inoculated with the sap from BMV infected barley using inoculation buffer composed of 50 mM $NaPO_4$, pH7.0, and 1% celite. Root samples were harvested 6 weeks post inoculation. RNA extraction and northern blot hybridization were performed as described above. FIG. 22 shows that BMV RNA3 replicated to very high levels in roots. In some (1a+2a)-transgenic plants (FIG. 22, lanes 2, 5, 6, 7, 8, 10) replication of launched RNA3 dramatically exceeded replication of wild-type BMV in non-transgenic *N. benthamiana* plants (FIG. 22, lane 1). This shows that this system can be used for delivery of RNA, proteins, peptides or other compounds to roots and enables testing of such compounds for various activities, for example, activities directed against root parasites. For example, proteins with anti-nematode activities can be inserted into RNA3 DNA-launching platform using the above described strategies and expressed in roots upon RNA3 replication. Such proteins can be engineered to be expressed in the cytoplasm or alternatively secreted into the surrounding soil.

Example 17—Barley Stripe Mosaic Virus

Barley stripe mosaic virus (BSMV) has a tripartite genome (RNA alpha, beta, and gamma). These genomic RNAs have an m7Gppp cap at the 5' end and a t-RNA like structure at the 3' end (Jackson and Hunter, 1989).

A DNA-launching plasmid for BSMV RNA alpha, RNA beta, and RNA gamma containing BSMV RNA cDNA is constructed by precisely fusing at its 5' end to a DNA-dependent RNA polymerase promoter and to a self-cleaving ribozyme at its 3' end. A polyadenylation signal may be also included. Alternatively, a convenient restriction site may be engineered at the 3' end of viral cDNAs. Foreign genes or sequences may be expressed in several ways. For example, DNA-launching plasmids based on BSMV RNA beta may contain a foreign gene or sequence expressed in place of ORF beta a.

Transgenic plants having one or more trans-acting factors fused to the DNA-dependent RNA polymerase promoter and terminator are obtained. Such trans-acting factors may include parts of the viral RNA replicase (ORFs alpha a and/or gamma a) or other trans-acting factors. The trans-acting factors are stably expressed in the plant cell or their expression may be induced if an inducible promoter is used. Cis-acting sequences necessary for BSMV RNA replication are removed from transgenes. Alternatively the full-length RNA alpha is expressed from the chromosome. Alternatively, ORF gamma a including the 5' untranslated region and ORF gamma b from a seed transmitted strain, such as ND18, are also expressed (Edwards, 1995).

A DNA-launching plasmid is constructed containing the DNA-dependent RNA polymerase promoter precisely fused to the 5' end of the BSMV RNA beta, cis-acting elements important for BSMV RNA beta life cycle, such as the 5' and 3' ends, the intercistronic region between the beta a and beta b ORFs (Zhou and Jackson, 1996) and a foreign gene or sequence in place of ORF beta a (coat protein) which is dispensable for BSMV replication and movement (Petty and Jackson, 1990). Such DNA-launching plasmids may lack the internal poly(A) region as this region is dispensable for replication and contain a ribozyme or a convenient restriction site at the 3' end of the modified viral RNA. Alternatively, a DNA-launching plasmid is constructed from RNA gamma in which ORFs gamma a and/or gamma b are replaced with foreign genes or sequences which may also include the triple gene block genes (ORFs beta b, beta c, and beta d) or a heterologous movement protein (TMV 30K, RCNMV 35K).

Example 18—Tobacco Mosaic Virus

Tobacco mosaic virus (TMV) has a single-stranded positive sense RNA genome. The 5' end has an m7Gppp cap and the 3' end contains a t-RNA like structure.

A DNA-launching plasmid is constructed based on TMV RNA containing TMV cDNA precisely fused at its 5' end to a DNA-dependent RNA polymerase promoter and at its 3' end to a self-cleaving ribozyme. A polyadenylation signal may be also included. Alternatively, a convenient restriction site may be engineered at the 3' end. Foreign gene may be expressed from an additional subgenomic RNA by including an additional subgenomic RNA promoter on the (−) strand.

Transgenic plants are obtained having one or more trans-acting factors fused to the DNA-dependent RNA polymerase promoter and terminator. Such factors may include the viral replicase (126K/183K), movement protein (30K), or coat protein (17.6K). At least one cis-acting sequence necessary for TMV RNA replication is removed from transgenes. The trans-acting factors are stably expressed in the plant cell or their expression may be induced if an inducible promoter is used.

A DNA-launching plasmid is constructed containing the DNA-dependent RNA polymerase promoter precisely fused to the 5' end of the TMV cDNA, cis-acting elements important for the TMV life cycle, such as the 5' and 3' ends, origin of assembly, etc., at least one foreign gene or sequence in place of the trans-acting factor that is expressed from the chromosome, and a ribozyme or a convenient restriction site at the 3' end. Alternatively, the foreign gene sequence can be expressed from an additional subgenomic RNA promoter and the sequence coding for the trans-acting factor that is expressed from the transgene can be deleted from the DNA-launching plasmid. Preferably, if the viral replicase proteins are expressed in transgenic plants, the DNA-launching plasmid will have a deletion of nucleotides 3420-4902, which appears to be a region that inhibits replication in trans. (Lewandowski et al., 1998).

Example 19—Potato Virus X

Potato virus X (PVX) has a single-stranded positive sense RNA genome. The 5' end has an m7Gppp cap and the 3' end is polyadenylated. A full-length cDNA clone of PVX has been constructed and infectious RNA transcripts obtained (Hemenway et al., 1990).

A DNA-launching plasmid is constructed based on PVX RNA containing PVX cDNA precisely fused at its 5' end to a DNA-dependent RNA polymerase promoter and having a polyadenylation site at its 3' end. A convenient restriction site may also be included at the 3' end. A foreign gene may be expressed from an additional subgenomic RNA.

Transgenic plants are obtained having one or more trans-acting factors fused to the DNA-dependent RNA polymerase promoter and terminator. Such factors may include the viral RNA polymerase gene (ORF1-147K), coat protein (ORF5-21K), or triple gene block (ORF2-25K, ORF3-12K, ORF4-8K). The triple gene block genes can be expressed individually. Alternatively, they can be expressed as negative sense transcripts from which plus sense subgenomic RNA for ORFs 2, 3, and 4 can be transcribed by the viral replicase. Such transgene will have a DNA-dependent RNA polymerase promoter fused to sequence of ORFs 2, 3, and 4 in the minus sense orientation and the transcribed sequence will include a subgenomic RNA promoter. At least one cis-acting sequence necessary for PVX RNA replication is removed from transgenes. The trans-acting factors are stably expressed in the plant cell or their expression may be induced if an inducible promoter is used.

A DNA-launching plasmid is constructed containing the DNA-dependent RNA polymerase promoter precisely fused to the 5' end of the PVX genome, cis-acting elements important for PVX life cycle, such as the 5' and 3' ends, origin of assembly, etc., at least one foreign gene or sequence in place of the trans-acting factor that is expressed from the chromosome and a polyadenylation signal. Alternatively, the foreign gene sequence can be expressed from an additional subgenomic RNA promoter and the sequence coding for the trans-acting factor that is expressed transgenically can be deleted from the DNA-launching plasmid.

Alternatively, a DNA-launching plasmid is constructed having a DNA-dependent RNA polymerase promoter, polyadenylation site, and the PVX cDNA sequence in which the ORF2 (25K) is replaced with a foreign gene or sequence. Alternatively, the ORF2 is deleted and the foreign gene is expressed from an additional subgenomic RNA promoter. Such a DNA-launching plasmid is inoculated to transgenic plants expressing movement protein from heterologous virus, such as tobacco mosaic virus (TMV 30K), tomato mosaic virus (ToMV 30K), or red clover necrotic mosaic virus (RCNMV 35K).

Example 20—Flock House Virus

Flock house virus (FHV) has a genome consisting of two single stranded RNAs. RNA1 encodes protein A, involved in RNA replication, and protein B that is translated from sg RNA3 and is dispensable for RNA replication. RNA2 encodes virion capsid precursor protein alpha. FHV is infectious to insect, plant, mammalian, and yeast cells (Selling et al., 1990; Price et al., 1996).

A DNA-launching plasmid is constructed for FHV RNA1 and RNA2 containing FHV RNA cDNA precisely fused at its 5' end to a DNA-dependent RNA polymerase promoter and at its 3' end to a self-cleaving ribozyme. A polyadenylation signal may be also included. Alternatively, a convenient restriction site may be engineered at the 3' end. Foreign genes or sequences may be expressed in several ways. For example, DNA-launching plasmids based on FHV RNA1 may contain a foreign gene or sequence expressed from subgenomic RNA3 as ORF B replacement or as a translational fusion with ORF B. Alternatively, a foreign gene may be expressed from an additional sg RNA. DNA-launching plasmids based on FHV RNA2 may contain a foreign gene(s) or sequence(s) expressed as a part of polyprotein alpha. Foreign gene(s) in such construct may include sequences necessary for polyprotein cleavage. DNA-launching plasmids will preferably also express a movement protein of a heterologous plant virus, such as 30K of TMV or 35K of RCNMV. Alternatively, DNA-launching plasmids will be inoculated onto transgenic plants expressing such movement protein.

Transgenic plants are obtained having one or more trans-acting factors fused to the DNA-dependent RNA polymerase promoter and terminator. Such factors may include protein A or capsid protein precursor alpha, and preferably will also include a movement protein from a plant virus, such as 30K of TMV or 35K of RCNMV. Trans-acting factors are stably expressed in the plant cell or their expression may be induced if an inducible promoter is used. Transgenically expressed trans-acting factors preferably lack at least one cis-acting factor which is necessary for their replication, such as the 5' and/or 3' end.

A DNA-launching plasmid is constructed based on FHV RNA1 or FHV RNA2 containing a DNA-dependent RNA polymerase promoter precisely fused to the 5' end of RNA1 (or RNA2), cis-acting elements important for FHV RNA1 (or RNA2) replication, such as the 5' and 3' ends, at least one foreign gene or sequence and a self-cleaving ribozyme at the 3' end. Polyadenylation signal may also be included. Alternatively, a convenient restriction site may be engineered at the 3' end of the modified viral RNA sequence of the DNA-launching plasmid. DNA-launching plasmids based on FHV RNA1 may contain a foreign gene or sequence in place of ORF A. Alternatively, the ORF A may be deleted and the foreign gene may be expressed from subgenomic RNA3, for example as an ORF B replacement or as a translational fusion with ORF B. Alternatively, DNA-launching plasmid may contain two exogenous RNA sequences, one in the place of ORF A and the other expressed from the subgenomic RNA3. DNA-launching plasmids based on FHV RNA2 may contain a foreign gene(s) or sequence(s) in place of ORF alpha or expressed as a part of polyprotein alpha. Foreign gene(s) in such a construct may include sequences necessary for polyprotein cleavage.

Example 21—Tomato Spotted Wild Virus

Tomato spotted wild virus (TSWV) is a tripartite (RNA L, M, S), negative sense and ambisense, single stranded RNA virus.

Transgenic plants are obtained having one or more trans-acting factors fused to the DNA-dependent RNA polymerase promoter and terminator. Such factors include the putative TSWV polymerase gene (ORF L), ORF N, and possibly other trans-acting factors (NSm or NSs). At least one cis-acting sequence, such as 5' and/or 3' ends, which are necessary for TSWV RNA replication are removed from the transgene. Trans-acting factors are stably expressed in the plant cell or their expression may be induced if an inducible promoter is used.

A DNA-launching plasmid is constructed based on TSWV RNA M in which the G1 and G2 coding sequences are replaced with at least one foreign gene or sequence. Such DNA-launching plasmid contains a DNA-dependent RNA polymerase promoter and TSWV RNA M cDNA fused to the self-cleaving ribozymes at the 5' and 3' ends. Alternatively, a DNA-launching plasmid is constructed based on TSWV RNA S in which the N coding region is replaced with a foreign gene or sequence.

Example 22—Barley Mild Mosaic Virus

Genome of barley mild mosaic virus (BaMMV) consists of two positive sense, single-stranded, 3'-polyadenylated RNAs. The RNA1 encodes proteins related to the potyviral P3, 6K1, CI, 61, NIa-VPg, NIa-Pro, NIb and capsid protein (Kashiwazaki et al., 1990). The RNA2 encodes P1 and P2 protein (Kashiwazaki et al., 1991). The P1 protein is related to the potyviral HC-Pro and the P2 protein is important for fungal transmission. An isolate was obtained containing a deletion in the P2 protein (Timpe and Kuhne, 1995) thus indicating that P2 is dispensable for viral RNA replication.

A DNA-launching plasmid is constructed for BaMMV RNA1 and RNA2 containing BaMMV RNA cDNA precisely fused at its 5' end to a DNA-dependent RNA polymerase promoter and a polyadenylation site at its 3' end. Foreign genes or sequences may be expressed in several ways. For example, DNA-launching plasmids based on BaMMV RNA2 may contain a foreign gene or sequence expressed as a part of polyprotein which can be cleaved and a foreign protein can be released.

Transgenic plants are obtained having the BaMMV RNA1 cDNA lacking the 5' and 3' ends fused to the DNA-dependent RNA polymerase promoter and terminator.

A DNA-launching plasmid is constructed based on BaMMV (isolate M) RNA2. Such plasmid contains a DNA-dependent RNA polymerase promoter precisely fused to the 5' end of RNA2, RNA2 cis-acting replication signals located in the 5' and 3' ends, P1 ORF and a foreign gene in place of P2 ORF or expressed as a part of P1/P2 polyprotein which can be cleaved and a foreign protein can be released.

The contents of all references cited throughout are incorporated herein by this reference to the extent they are not inconsistent with the disclosure, teachings, and principles of the subject invention.

It should be understood that the examples and embodiments described herein are for illustrative purposes only and that various modifications or changes in light thereof will be suggested to persons skilled in the art and are to be included within the spirit and purview of this application.

REFERENCES

De Jong and Ahlquist (1992) “A hybrid plant RNA virus made by transferring the noncapsid movement protein from a rod-shaped to an icosahedral virus is competent for systemic infection,” *PNAS* 89: 6808-6812.

Dinant, S., Janda, M., Kroner, P. A., Ahlquist, P. (1993) “Bromovirus RNA replication and transcription requires compatibility between the polymerase- and helicase-like viral RNA synthesis proteins,” *J. Virol.* 67: 7181-7189.

Edwards, M. C. (1995) “Mapping of the seed transmission determinants of barley stripe mosaic virus,” *MPMI* 8:906-915.

French, R. and Ahlquist, P. (1988) “Characterization and engineering of sequences controlling in vivo synthesis of brome mosaic virus RNA3,” *J. Virol.* 62(7):2411-2421.

Hemenway, C., Weiss, J., O'Connell, K., and Turner, N. E. (1990) “Characterization of infectious transcripts from a potato virus X cDNA clone,” *Virology* 175:365-371.

Ishikawa, M., Diez, J., Restrepo-Hartwig, M., Ahlquist, P. (1997) “Yeast mutations in multiple complementation groups inhibit brome mosaic virus RNA replication and transcription and perturb regulated expression of viral polymerase-like gene,” *PNAS* 94:13810-13815.

Jackson, A. O. and Hunter, B. G. (1989) “Hordeivirus relationships and genome organization,” *Annu. Rev. Phytopathol.* 27:95-121.

Janda, M., French, R., Ahlquist, P. (1987) “High efficiency T7 polymerase synthesis of infectious RNA from cloned brome mosaic virus cDNA and effect of 5' extensions on transcript infectivity,” *Virology* 158:259-262.

Kashiwazaki, S. Minobe, Y., Omura, T., Hibino, H. (1990) “Nucleotide sequence of barley yellow mosaic virus RNA1: a close evolutionary relationship with potyviruses,” *Journal of General Virology* 71:2781-2790.

Kashiwazaki, S., Minobe, Y., Hibino, H. (1991) “Nucleotide sequence of barley yellow mosaic virus RNA2,” *Journal of General Virology* 72:995-999.

Kikkert (1993) “The biolistic PDS 1000/He device,” *Plant Cell Tiss. and Org. Cult.* 33:221-226.

Lewandowski, Dennis J., Dawson, William O. (1998) “Deletion of internal sequences results in tobacco mosaic virus defective RNAs that accumulate to high levels without interfering with replication of the helper virus,” *Virology* 251(2):427-437.

Pacha, R. F. and Ahlquist, P. (1991) “Use of Bromovirus RNA3 hybrids to study template specificity in viral RNA amplification,” *Journal of Virology* 65:3693-3703.

Petty, I. T. D. and Jackson, A. O. (1990) “Mutational analysis of barley stripe mosaic virus RNA beta,” *Virology* 179:712-718.

Price, B. D., Rueckert, R. R., Ahlquist, P. (1996) “Complete replication of an animal virus and maintenance of expression vectors derived from it in *Saccharomyces cerevisiae*” *PNAS* 93:9465-9470.

Rasochova, L. and Miller, W. A. (1996) “Satellite RNA of barley yellow dwarf-RPV virus reduces accumulation of RPV helper virus RNA and attenuates RPV symptoms on oats,” *Molecular Plant-Microbe Interact* 9:646-650.

Sacher, R., French, R., Ahlquist, P. (1988) “Hybrid brome mosaic virus RNAs express and are packaged in tobacco mosaic virus coat protein in vivo,” *Virology* 167:15-24.

Selling, B. H., Allison, R. F., Kaesberg, P. (1990) “Genomic RNA of an insect virus directs synthesis of infectious virions in plants,” *PNAS* 87:434-438.

Timpe, U. and Kuhne, T. (1995) □In vitro transcript of a full-length cDNA of a naturally deleted RNA2 of barley mild mosaic virus (BaMMV) replicate in BaMMV-infected plants, □ *Journal of General Virology* 76:2619-2623.

Töpfer, R., Matzeit, V., Gronenborn, B., Schell, J., Steinbiss, H. H. (1987) “A set of plant expression vectors for transcriptional and translational fusions,” *Nucleic Acids Res.* 15:5890.

U.S. Pat. No. 5,500,360.

Zhou, H. and Jackson, A. O. (1996) “Analysis of cis-acting elements for replication of barley stripe mosaic virus RNA,” *Virology* 219:150-160.

The invention claimed is:

1. A method of genotypically or phenotypically modifying one or more plant cells, said plant cell or cells having been rendered transgenic by stably comprising heterologous DNA encoding a trans-acting viral replication element that is incapable of self replication, said method comprising the following steps:

a) obtaining a DNA transfection vector comprising:

1) a polynucleotide molecule encoding a viral RNA molecule that has been modified to be incapable of self replication, but which replicates when expressed in a plant cell in the presence of a viral trans-acting element necessary for replication of the RNA, said viral RNA molecule also having been modified to include an exogenous RNA segment, 2) a DNA-dependent RNA polymerase promoter located at the 5' end region of the polynucleotide molecule encoding the viral RNA molecule, and 3) a nucleotide sequence located at the 3' end region of the polynucleotide molecule encoding the viral RNA molecule, wherein the nucleotide sequence is selected from one of the following:

i) a nucleotide sequence encoding a ribozyme, wherein the ribozyme cleaves at the 3' end of the polynucleotide molecule encoding the viral RNA molecule, ii) a transcription termination sequence, and iii) a restriction site that directs cleavage at the 3' end of the polynucleotide molecule encoding the viral RNA molecule; and b) transfecting said one or more cells with said DNA transfection vector, wherein said polynucleotide molecule is transcribed thereby forming a replicatable RNA transcript that does not self replicate but is replicatable in the presence of said trans-acting viral replication element, wherein expression of said RNA-transcript confers a genotype or phenotype modification in said one or more plant cells, wherein said trans-acting viral replication element and said viral RNA molecule are derived from the same virus, and wherein said DNA transfection vector remains separate from the genome of the plant cell or cells.

2. The method of claim 1 wherein said trans-acting viral replication element is constitutively expressed.

3. The method of claim 1 wherein said DNA transfection vector comprises a ribozyme sequence, wherein the ribozyme cleaves at the 3' end of the polynucleotide molecule encoding the viral RNA molecule.

4. The method of claim 1 wherein said DNA transfection vector comprises a termination sequence located at the 3' end region of the polynucleotide molecule encoding the viral RNA molecule.

5. The method of claim 1 wherein said DNA transfection vector comprises a restriction site that directs cleavage at the 3' end of the polynucleotide molecule encoding the viral RNA molecule.

6. A method of producing a plant or plant tissue comprising at least one genotypically or phenotypically modified plant cell, said cell having been rendered transgenic by stably comprising heterologous DNA encoding a trans-acting viral replication element that is incapable of self replication, said method comprising:

a) transfecting cells of said plant or plant tissue with a DNA transfection vector, wherein said DNA transfection vector remains separate from the genome of the cells, and wherein said DNA transfection vector comprises:

1) a polynucleotide molecule encoding a viral RNA molecule that has been modified to be incapable of self replication, but which replicates when expressed in a plant cell in the presence of a viral trans-acting element necessary for replication of the RNA, said viral RNA molecule also having been modified to include an exogenous RNA segment, such that said polynucleotide is transcribed to form a replicatable RNA transcript that does not self replicate but is replicatable in the presence of said trans-acting viral replication element, 2) a DNA-dependent RNA polymerase promoter located at the 5' end region of the polynucleotide molecule encoding the viral RNA molecule, and 3) a nucleotide sequence located at the 3' end region of the polynucleotide molecule encoding the viral RNA molecule, wherein the nucleotide sequence is selected from one of the following:

i) a nucleotide sequence encoding a ribozyme, wherein the ribozyme cleaves at the 3' end of the polynucleotide molecule encoding the viral RNA molecule, ii) a transcription termination sequence, and iii) a restriction site that directs cleavage at the 3' end of the polynucleotide molecule encoding the viral RNA molecule;

wherein the polynucleotide molecule encoding the viral RNA molecule is not flanked by two inverted repeat nucleotide sequences;

wherein said trans-acting viral replication element and said viral RNA molecule are derived from the same virus, and whereby expression of said RNA transcript confers a genotypic or phenotypic modification in at least one of said transfected cells.

7. The method of claim 6 wherein said DNA transfection vector comprises a ribozyme sequence, wherein the ribozyme cleaves at the 3' end of the polynucleotide molecule encoding the viral RNA molecule.

8. The method of claim 6 wherein said DNA transfection vector comprises a termination sequence located at the 3' end region of the polynucleotide molecule encoding the viral RNA molecule.

9. The method of claim 6 wherein said DNA transfection vector comprises a restriction site that directs cleavage at the 3' end of the polynucleotide molecule encoding the viral RNA molecule.

10. A method of producing a genotypically or phenotypically modified plant comprising obtaining at least one modified cell produced by the method of claim 1; and subjecting said modified cell to conditions whereby a plant is regenerated therefrom.

11. The method of claim 6, wherein said plant or plant tissue comprises one or more cells transformed with a polynucleotide molecule encoding at least one trans-acting viral replication element and wherein said polynucleotide molecule is constitutively expressed.

12. The method of claim 1, wherein said trans-acting viral replication element and said viral RNA molecule are derived from brome mosaic virus.

13. The method of claim 1, wherein the DNA-dependent RNA polymerase promoter is fused to the 5' end of the polynucleotide molecule encoding the viral RNA molecule, and wherein the nucleotide sequence located at the 3' end region of the polynucleotide encoding, the viral RNA molecule is fused to the 3' end of the polynucleotide molecule encoding the viral RNA molecule, and the nucleotide sequence is selected from one of the following:

i) a nucleotide sequence encoding a ribozyme, wherein the ribozyme cleaves at the 3' end of the polynucleotide molecule encoding the viral RNA molecule, ii) a transcription termination sequence, and iii) a restriction site that directs cleavage at the 3'end of the polynucleotide molecule encoding the viral RNA molecule.

14. The method of claim 1, wherein said DNA transfection vector further comprises a nucleotide sequence encoding a viral coat protein.

15. The method of claim 1, wherein the trans-acting viral replication element comprises a viral replicase and/or viral RNA polymerase.

16. The method of claim 6, wherein said trans-acting viral replication element and said viral RNA molecule are derived from brome mosaic virus.

17. The method of claim 6, wherein the DNA-dependent RNA polymerase promoter is fused to the 5' end of the polynucleotide molecule encoding the viral RNA molecule, and wherein the nucleotide sequence located at the 3' end region of the polynucleotide encoding the viral RNA molecule is fused to the 3' end of the polynucleotide molecule encoding the viral RNA molecule, and the nucleotide sequence is selected from one of the following:

i) a nucleotide sequence encoding a ribozyme, wherein the ribozyme cleaves at the 3' end of the polynucleotide molecule encoding the viral RNA molecule, ii) a transcription termination sequence, and iii) a restriction site that directs cleavage at the 3'end of the polynucleotide molecule encoding the viral RNA molecule.

18. The method of claim 6, wherein said DNA transfection vector further comprises a nucleotide sequence encoding a viral coat protein.

19. The method of claim 6, wherein the trans-acting viral replication element comprises a viral replicase and/or viral RNA polymerase.

20. The method of claim 6, wherein said replicatable RNA transcript moves cell-to-cell throughout the plant tissue or within the plant tissue.

21. The method of claim 20, wherein said replicable RNA transcript is expressed to produce a protein of interest in cells without DNA encoding the protein of interest.

* * * * *

UNITED STATES PATENT AND TRADEMARK OFFICE

CERTIFICATE OF CORRECTION

PATENT NO. : 10,308,946 B2
APPLICATION NO. : 11/621850
DATED : June 4, 2019
INVENTOR(S) : Lada Rasochova et al.

It is certified that error appears in the above-identified patent and that said Letters Patent is hereby corrected as shown below:

In the Specification

Column 1, Lines 14-18:
Delete the phrase:
"This invention was made with United States government support awarded by the following agency: NIH Grant No: GM35072 The United States government has certain rights in this invention."

And replace with:
--REFERENCE TO GOVERNMENT RIGHTS
This invention was made with government support under GM035072 awarded by the National Institutes of Health. The government has certain rights in the invention.--.

Signed and Sealed this
Twenty-second Day of December, 2020

Andrei Iancu
*Director of the United States Patent and Trademark Office*